United States Patent
Narva et al.

(10) Patent No.: US 9,688,983 B2
(45) Date of Patent: Jun. 27, 2017

(54) NUCLEIC ACID MOLECULES THAT CONFER RESISTANCE TO COLEOPTERAN PESTS

(71) Applicant: Dow AgroSciences LLC, Indianapolis, IN (US)

(72) Inventors: Kenneth Narva, Zionsville, IN (US); Huarong Li, Zionsville, IN (US); Chaoxian Geng, Zionsville, IN (US); Ignacio M. Larrinua, Indianapolis, IN (US); Monica B. Olson, Lebanon, IN (US); Navin Elango, Indianapolis, IN (US); Matthew J. Henry, Indianapolis, IN (US); Aaron T. Woosley, Fishers, IN (US); Murugesan Rangasamy, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 265 days.

(21) Appl. No.: 14/105,231

(22) Filed: Dec. 13, 2013

(65) Prior Publication Data

US 2014/0298536 A1 Oct. 2, 2014

Related U.S. Application Data

(60) Provisional application No. 61/740,168, filed on Dec. 20, 2012.

(51) Int. Cl.
- *C12N 15/11* (2006.01)
- *C12N 15/82* (2006.01)
- *C12N 15/113* (2010.01)

(52) U.S. Cl.
CPC ........ *C12N 15/113* (2013.01); *C12N 15/8286* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 5,107,065 A | 4/1992 | Shewmaker et al. | |
| 5,231,020 A | 7/1993 | Jorgensen et al. | |
| 5,283,184 A | 2/1994 | Jorgensen et al. | |
| 5,759,829 A | 6/1998 | Shewmaker et al. | |
| 7,612,194 B2 | 11/2009 | Andersen et al. | |
| 7,943,819 B2 * | 5/2011 | Baum ................ | C07H 21/04 800/278 |
| 2002/0048814 A1 | 4/2002 | Oeller | |
| 2003/0018993 A1 | 1/2003 | Gutterson et al. | |
| 2007/0050860 A1 | 3/2007 | Andersen et al. | |
| 2007/0124836 A1 | 5/2007 | Baum et al. | |
| 2009/0306189 A1 | 12/2009 | Raemaekers et al. | |
| 2010/0192265 A1 | 7/2010 | Anderson et al. | |
| 2011/0154545 A1 | 6/2011 | Anderson et al. | |

FOREIGN PATENT DOCUMENTS

| | | | |
|---|---|---|---|
| WO | WO94/01550 | 1/1994 | |
| WO | WO98/05770 A3 | 3/1998 | |
| WO | WO2011025860 A1 | 3/2011 | |
| WO | PCT/US2011/068062 | 12/2011 | |
| WO | PCT/US2011/068144 | 12/2011 | |
| WO | PCT/US2011/068162 | 12/2011 | |
| WO | PCT/US2011/068188 | 12/2011 | |
| WO | WO 2012092580 A2 * | 7/2012 | ....... C07K 14/43563 |

OTHER PUBLICATIONS

Tribolium Genome Sequencing Consortium (The genome of the model beetle and pest Tribolium castaneum. Nature. 452:949-955, Apr. 24, 2008).*
Diop et al., (2008) EMBO J. 9: 260-266.
Qi et al., (2006) Genetics 174: 241-251.
Bauer et al., (2000) EMBO J. 19: 6121-6130.
Bellosta et al., (2005) Proc. Natl. Acad. Sci. U.S.A. 102: 11799-11804.

* cited by examiner

*Primary Examiner* — Medina A Ibrahim
*Assistant Examiner* — Wayne Zhong
(74) *Attorney, Agent, or Firm* — James Daly IV

(57) ABSTRACT

This disclosure concerns nucleic acid molecules and methods of use thereof for control of coleopteran pests through RNA interference-mediated inhibition of target coding and transcribed non-coding sequences in coleopteran pests. The disclosure also concerns methods for making transgenic plants that express nucleic acid molecules useful for the control of coleopteran pests, and the plant cells and plants obtained thereby.

17 Claims, 1 Drawing Sheet

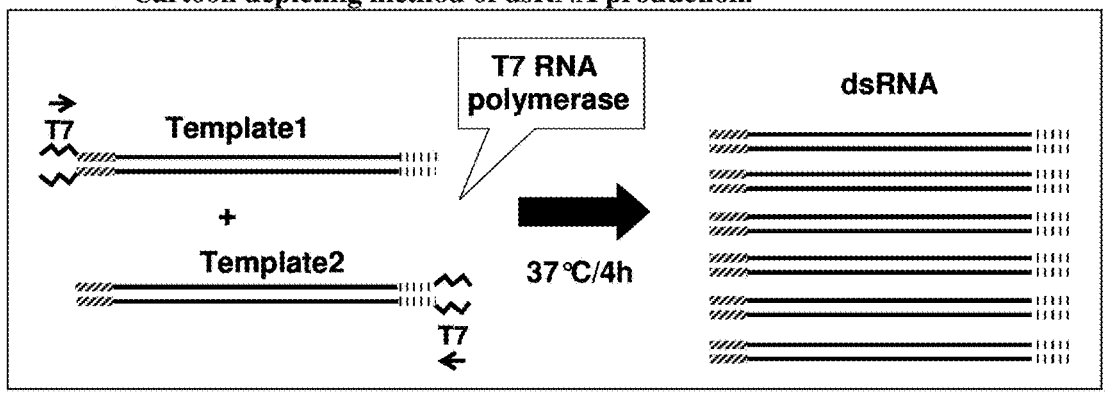
Cartoon depicting method of dsRNA production.

NUCLEIC ACID MOLECULES THAT CONFER RESISTANCE TO COLEOPTERAN PESTS

CROSS REFERENCE TO RELATED APPLICATION

This application claims priority to U.S. Provisional Patent Application Ser. No. 61/740,168, filed Dec. 20, 2012, the disclosure of which is hereby incorporated herein in its entirety by this reference.

TECHNICAL FIELD OF THE DISCLOSURE

The present invention relates generally to genetic control of plant damage caused by coleopteran pests. In particular embodiments, the present invention relates to identification of target coding and non-coding sequences, and the use of recombinant DNA technologies for post-transcriptionally repressing or inhibiting expression of target coding and non-coding sequences in the cells of a coleopteran pest to provide a plant protective effect.

BACKGROUND

The western corn rootworm (WCR), *Diabrotica virgifera virgifera* LeConte, is one of the most devastating corn rootworm species in North America and is a particular concern in corn-growing areas of the Midwestern United States. The northern corn rootworm (NCR), *Diabrotica barberi* Smith and Lawrence, is a closely-related species that co-inhabits much of the same range as WCR. There are several other related subspecies of *Diabrotica* that are significant pests in North America: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella*; and *D. u. undecimpunctata* Mannerheim. The United States Department of Agriculture currently estimates that corn rootworms cause $1 billion in lost revenue each year, including $800 million in yield loss and $200 million in treatment costs.

Both WCR and NCR are deposited in the soil as eggs during the summer. The insects remain in the egg stage throughout the winter. The eggs are oblong, white, and less than 0.004 inches (0.010 cm) in length. The larvae hatch in late May or early June, with the precise timing of egg hatching varying from year to year due to temperature differences and location. The newly hatched larvae are white worms that are less than 0.125 inches (0.3175 cm) in length. Once hatched, the larvae begin to feed on corn roots. Corn rootworms go through three larval instars. After feeding for several weeks, the larvae molt into the pupal stage. They pupate in the soil, and then they emerge from the soil as adults in July and August. Adult rootworms are about 0.25 inches (0.635 cm) in length.

Corn rootworm larvae complete development on corn and several other species of grasses. Larvae reared on yellow foxtail emerge later and have a smaller head capsule size as adults than larvae reared on corn. Ellsbury et al. (2005) Environ. Entomol. 34:627-34. WCR adults feed on corn silk, pollen, and kernels on exposed ear tips. If WCR adults emerge before corn reproductive tissues are present, they may feed on leaf tissue, thereby slowing plant growth and occasionally killing the host plant. However, the adults will quickly shift to preferred silks and pollen when they become available. NCR adults also feed on reproductive tissues of the corn plant, but in contrast rarely feed on corn leaves.

Most of the rootworm damage in corn is caused by larval feeding. Newly hatched rootworms initially feed on fine corn root hairs and burrow into root tips. As the larvae grow larger, they feed on and burrow into primary roots. When corn rootworms are abundant, larval feeding often results in the pruning of roots all the way to the base of the corn stalk. Severe root injury interferes with the roots' ability to transport water and nutrients into the plant, reduces plant growth, and results in reduced grain production, thereby often drastically reducing overall yield. Severe root injury also often results in lodging of corn plants, which makes harvest more difficult and further decreases yield. Furthermore, feeding by adults on the corn reproductive tissues can result in pruning of silks at the ear tip. If this "silk clipping" is severe enough during pollen shed, pollination may be disrupted.

Control of corn rootworms may be attempted by crop rotation, chemical insecticides, biopesticides (e.g., the spore-forming gram-positive bacterium, *Bacillus thuringiensis*), or a combination thereof. Crop rotation suffers from the significant disadvantage of placing unwanted restrictions upon the use of farmland. Moreover, oviposition of some rootworm species may occur in soybean fields, thereby mitigating the effectiveness of crop rotation practiced with corn and soybean.

Chemical insecticides are the most heavily relied upon strategy for achieving corn rootworm control. Chemical insecticide use, though, is an imperfect corn rootworm control strategy; over $1 billion may be lost in the United States each year due to corn rootworm when the costs of the chemical insecticides are added to the costs of the rootworm damage that may occur despite the use of the insecticides. High populations of larvae, heavy rains, and improper application of the insecticide(s) may all result in inadequate corn rootworm control. Furthermore, the continual use of insecticides may select for insecticide-resistant rootworm strains, as well as raise significant environmental concerns due to the toxicity of many of them to non-target species.

RNA interference (RNAi) is a process utilizing endogenous cellular pathways, whereby an interfering RNA (iRNA) molecule (e.g., a dsRNA molecule) that is specific for all, or any portion of adequate size, of a target gene sequence results in the degradation of the mRNA encoded thereby. In recent years, RNAi has been used to perform gene "knockdown" in a number of species and experimental systems; for example, *Caenorhabitis elegans*, plants, insect embryos, and cells in tissue culture. See, e.g., Fire et al. (1998) Nature 391:806-11; Martinez et al. (2002) Cell 110:563-74; McManus and Sharp (2002) Nature Rev. Genetics 3:737-47.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro inhibitory ribonucleic acid (miRNA) molecules may be similarly incorporated into RISC. Post-transcriptional gene silencing occurs when the guide strand binds specifically to a complementary sequence of an mRNA molecule and induces cleavage by Argonaute, the catalytic component of the RISC complex. This process is known to spread systemically throughout the organism despite initially limited concentrations of siRNA and/or miRNA in some eukaryotes such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein.

U.S. Pat. No. 7,612,194 and U.S. Patent Publication Nos. US 2007/0050860, US 2010/0192265, and US 2011/0154545 disclose a library of 9112 expressed sequence tag (EST) sequences isolated from *D. v. virgifera* LeConte pupae. It is suggested in U.S. Pat. No. 7,612,194 and U.S. Patent Publication No. US 2007/0050860 to operably link to a promoter a nucleic acid molecule that is complementary to one of several particular partial sequences of *D. v. virgifera* vacuolar-type H$^+$-ATPase (V-ATPase) disclosed therein for the expression of anti-sense RNA in plant cells. U.S. Patent Publication No. US 2010/0192265 suggests operably linking a promoter to a nucleic acid molecule that is complementary to a particular partial sequence of a *D. v. virgifera* gene of unknown and undisclosed function (the partial sequence is stated to be 58% identical to C56C10.3 gene product in *C. elegans*) for the expression of anti-sense RNA in plant cells. U.S. Patent Publication No. US 2011/0154545 suggests operably linking a promoter to a nucleic acid molecule that is complementary to two particular partial sequences of *D. v. virgifera* coatomer beta subunit genes for the expression of anti-sense RNA in plant cells. Further, U.S. Pat. No. 7,943,819 discloses a library of 906 expressed sequence tag (EST) sequences isolated from *D. v. virgifera* LeConte larvae, pupae, and dissected midgets, and suggests operably linking a promoter to a nucleic acid molecule that is complementary to a particular partial sequence of a *D. v. virgifera* charged multivesicular body protein 4b gene for the expression of double-stranded RNA in plant cells.

No further suggestion is provided in U.S. Pat. No. 7,612,194, and U.S. Patent Publication Nos. US 2007/0050860, US 2010/0192265 and US 2011/0154545 to use any particular sequence of the more than nine thousand sequences listed therein for RNA interference, other than the several particular partial sequences of V-ATPase and the particular partial sequences of genes of unknown function. Furthermore, none of U.S. Pat. No. 7,612,194, and U.S. Patent Publication Nos. US 2007/0050860 and US 2010/0192265, and US 2011/0154545 provides any guidance as to which other of the over nine thousand sequences provided would be lethal, or even otherwise useful, in species of corn rootworm when used as dsRNA or siRNA. U.S. Pat. No. 7,943,819 provides no suggestion to use any particular sequence of the more than nine hundred sequences listed therein for RNA interference, other than the particular partial sequence of a charged multivesicular body protein 4b gene. Furthermore, U.S. Pat. No. 7,943,819 provides no guidance as to which other of the over nine hundred sequences provided would be lethal, or even otherwise useful, in species of corn rootworm when used as dsRNA or siRNA.

The overwhelming majority of sequences complementary to corn rootworm DNAs (such as the foregoing) are not lethal in species of corn rootworm when used as dsRNA or siRNA. For example, Baum et al. (2007), describe the effects of inhibiting several WCR gene targets by RNAi. These authors reported that the 8 of 26 target genes they tested were not able to provide experimentally significant coleopteran pest mortality at a very high iRNA (e.g., dsRNA) concentration of more than 520 ng/cm$^2$.

SUMMARY OF THE DISCLOSURE

Disclosed herein are nucleic acid molecules (e.g., target genes, DNAs, dsRNAs, siRNAs, miRNAs, and hpRNAs), and methods of use thereof, for the control of coleopteran pests, including, for example, *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella*; and *D. u. undecimpunctata* Mannerheim. In particular examples, exemplary nucleic acid molecules are disclosed that may be homologous to at least a portion of one or more native nucleic acid sequences in a coleopteran pest.

In these and further examples, the native nucleic acid sequence may be a target gene, the product of which may be, for example and without limitation: involved in a metabolic process; involved in a reproductive process; or involved in larval development. In some examples, post-translation inhibition of the expression of a target gene by a nucleic acid molecule comprising a sequence homologous thereto may be lethal in coleopteran pests, or result in reduced growth and/or reproduction. In specific examples, a novel gene disclosed as reptin may be selected as a target gene for post-transcriptional silencing. In particular examples, a target gene useful for post-transcriptional inhibition is the novel gene referred to herein as reptin. An isolated nucleic acid molecule comprising a nucleotide sequence comprising reptin (SEQ ID NO:1), and fragments thereof, including but not limited to SEQ ID NOs: 21, 22, and 23, is therefore disclosed herein. Also disclosed herein are plant transformation vectors, plant cells, plants, plant parts (including seeds), and commodity products comprising the novel nucleic acid molecules, and methods of making same.

Also disclosed are nucleic acid molecules comprising a nucleotide sequence that encodes a polypeptide that is at least 85% identical to an amino acid sequence within a target gene product (for example, the product of a gene disclosed as reptin. For example, a nucleic acid molecule may comprise a nucleotide sequence encoding a polypeptide that is at least 85% identical to an amino acid sequence consisting of SEQ ID NO:2 (reptin protein), or fragments thereof. In particular examples, a nucleic acid molecule comprises a nucleotide sequence encoding a polypeptide that is at least 85% identical to an amino acid sequence within a product encoded by reptin. Further disclosed are nucleic acid molecules comprising a nucleotide sequence that is the reverse complement of a nucleotide sequence that encodes a polypeptide at least 85% identical to an amino acid sequence within a target gene product.

Also disclosed are cDNA sequences that may be used for the production of iRNA (e.g., dsRNA, siRNA, miRNA, and hpRNA) molecules that are complementary to all or part of a coleopteran pest target gene, for example, reptin. In particular embodiments, dsRNAs, siRNAs, miRNAs, and/or hpRNAs may be produced in vitro, or in vivo by a genetically-modified organism, such as a plant or bacterium. In particular examples, cDNA molecules are disclosed that may be used to produce iRNA molecules that are complementary to all or part of reptin (SEQ ID NO:1).

Further disclosed are means for inhibiting expression of an essential gene in a coleopteran pest, and means for providing coleopteran pest resistance to a plant. A means for inhibiting expression of an essential gene in a coleopteran pest is a single- or double-stranded RNA molecule consisting of at least one of SEQ ID NOs:1, 21, 22, 23, or 24, or the complement thereof. Functional equivalents of means for inhibiting expression of an essential gene in a coleopteran pest include single- or double-stranded RNA molecules that are substantially homologous to all or part of a WCR gene comprising SEQ ID NO:1. A means for providing coleopteran pest resistance to a plant is a DNA molecule comprising a nucleic acid sequence encoding a means for inhibiting expression of an essential gene in a coleopteran pest operably linked to a promoter, wherein the DNA molecule is capable of being integrated into the genome of a maize plant.

Disclosed are methods for controlling a population of a coleopteran pest, and concomitant methods for improving the yield of a crop infected by such coleopteran pest population, comprising providing to a coleopteran pest an iRNA (e.g., dsRNA, siRNA, miRNA, and hpRNA) molecule that functions upon being taken up by the coleopteran pest to inhibit a biological function within the coleopteran pest, wherein the iRNA molecule comprises a nucleotide sequence selected from the group consisting of: all or part of SEQ ID NO:1; the complement of all or part of SEQ ID NO:1; a native coding sequence of a *Diabrotica* organism (e.g., WCR) comprising all or part of SEQ ID NO:1; the complement of a native coding sequence of a *Diabrotica* organism comprising all or part of SEQ ID NO:1; a native non-coding sequence of a *Diabrotica* organism that is transcribed into a native RNA molecule comprising all or part of SEQ ID NO:1; and the complement of a native non-coding sequence of a *Diabrotica* organism that is transcribed into a native RNA molecule comprising all or part of SEQ ID NO:1.

In particular examples, methods are disclosed for controlling a population of a coleopteran pest, and comprising providing to a coleopteran pest an iRNA (e.g., dsRNA, siRNA, miRNA, and hpRNA) molecule that functions upon being taken up by the coleopteran pest to inhibit a biological function within the coleopteran pest, wherein the iRNA molecule comprises a nucleotide sequence selected from the group consisting of: all or part of SEQ ID NO:1; the complement of all or part of SEQ ID NO:1; all or part of a native coding sequence of a *Diabrotica* organism (e.g., WCR) comprising SEQ ID NO:1; all or part of the complement of a native coding sequence of a *Diabrotica* organism comprising SEQ ID NO:1; all or part of a native non-coding sequence of a *Diabrotica* organism that is transcribed into a native RNA molecule comprising SEQ ID NO:1; and all or part of the complement of a native non-coding sequence of a *Diabrotica* organism that is transcribed into a native RNA molecule comprising SEQ ID NO:1.

Also disclosed herein are methods wherein dsRNAs, siRNAs, miRNAs, and/or hpRNAs may be provided to a coleopteran pest in a diet-based assay, or in genetically-modified plant cells expressing the dsRNAs, siRNAs, miRNAs, and/or hpRNAs. In these and further examples, the dsRNAs, siRNAs, miRNAs, and/or hpRNAs may be ingested by coleopteran pest larvae. Ingestion of dsRNAs, siRNA, miRNAs, and/or hpRNAs of the invention may then result in RNAi in the larvae, which in turn may result in silencing of a gene essential for viability of the coleopteran pest and leading ultimately to larval mortality. Thus, methods are disclosed wherein nucleic acid molecules comprising exemplary nucleic acid sequence(s) useful for control of coleopteran pests are provided to a coleopteran pest. In particular examples, the coleopteran pest controlled by use of nucleic acid molecules of the invention may be WCR or NCR. The foregoing and other features will become more apparent from the following Detailed Description of several embodiments, which proceeds with reference to the accompanying Figures.

BRIEF DESCRIPTION OF THE FIGURES

FIG. 1 includes a depiction of the strategy used to provide specific templates for dsRNA production.

SEQUENCE LISTING

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand and reverse complementary strand are understood as included by any reference to the displayed strand. In the accompanying sequence listing:

SEQ ID NO:1 shows a DNA sequence encoding reptin.

SEQ ID NO:2 shows a derived polypeptide sequence of a reptin protein encoded by SEQ ID NO:1.

SEQ ID NO:3 shows a sequence of a T7 phage promoter.

SEQ ID NO:4 shows a YFP DNA sequence.

SEQ ID NOs:5 to 20 show PCR primers used to amplify portions of a reptin sequence and PCR primers used to amplify a portion of a YFP coding region.

SEQ ID NO:21 shows an exemplary amplified fragment of reptin Reg1 used for in vitro dsRNA synthesis, which was amplified using primer Pair 1 (T7 at 5' end) and primer Pair 2 (T7 at 3' end). T7 promoter sequences at the 5' and 3' ends are not shown.

SEQ ID NO:22 shows an exemplary amplified fragment of reptin Reg2 used for in vitro dsRNA synthesis, which was amplified using primer Pair 3 (T7 at 5' end) and primer Pair 4 (T7 at 3' end). T7 promoter sequences at the 5' and 3' ends are not shown.

SEQ ID NO:23 shows an exemplary amplified fragment of reptin Reg3 used for in vitro dsRNA synthesis, which was amplified using primer Pair 5 (T7 at 5' end) and primer Pair 6 (T7 at 3' end). T7 promoter sequences at the 5' and 3' ends are not shown.

SEQ ID NO:24 shows the sequence of a reptin hairpin RNA-forming sequence containing an ST-LS1 intron (underlined). The upper case bases correspond to bases 173 to 469 of SEQ ID NO:1 and represent reptin sense orientation DNA. The lower case letters not underlined represent the antisense orientation of the sense strand sequence:

AAATAGCCGAGGTGCGCGAAACAACTCGCGTTGAAAGAATTGGGGCCC

ATTCTCACATTCGAGGTCTAGGATTAGATGATAGTCTTGAAGCCAGAC

ATGTGTCTCAAGGTATGGTCGGCCAAGTAACAGCTAGAAGAGCTGTAG

GTATCGTTCTACAAATGGTTAGAGAAGGAAGAATTGCCGGCAGAGCGG

TCCTCTTGGCTGGACAACCTGGTACTGGTAAAACAGCAATAGCTACAG

CTTTGGCTCATGCACTTGGTCAAGATACCCCTTTCACAAGTATGGCAG

GTTCCGAAAgactagtaccggttgggaaaggtatgtttctgatctacc tttgatatatatataataattatcactaattagtagtaatatagtatt tcaagtatttattcaaaataaaagaatgtagtatatagctattgcttt tctgtagtttataagtgtgtatattttaatttataacttttctaatat -continued

```
atgaccaaaacatggtgatgtgcaggttgatccgcggttatttcggaa cctgccatacttgtgaaaggggtatcttgaccaagtgcatgagccaaa gctgtagctattgctgttttaccagtaccaggttgtccagccaagagg accgctctgccggcaattcttccttctctaaccatttgtagaacgata cctacagctcttctagctgttacttggccgaccataccttgagacaca tgtctggcttcaagactatcatctaatcctagacctcgaatgtgagaa tgggccccaattctttcaacgcgagttgtttcgcgcacctcggctattt
```

SEQ ID NO:25 shows a DNA sequence of annexin region 1.

SEQ ID NO:26 shows a DNA sequence of annexin region 2.

SEQ ID NO:27 shows a DNA sequence of beta spectrin 2 region 1.

SEQ ID NO:28 shows a DNA sequence of beta spectrin 2 region 2.

SEQ ID NO:29 shows a DNA sequence of mtRP-L4 region 1.

SEQ ID NO:30 shows a DNA sequence of mtRP-L4 region 2.

SEQ ID NOs:31-54 show primers used to amplify gene regions of annexin, beta spectrin 2, and mtRP-L4 for dsRNA synthesis.

SEQ ID NO:55 shows a DNA sequence of an ST-LS1 intron.

SEQ ID NOs:56-59 show sequences of primers used to amplify regions of a maize TIP41-like gene and primers used to amplify a maize Per5 3' UTR SEQ ID NOs:60-74 show sequences of primers and probes used in hydrolysis probe assays.

SEQ ID NO:75 shows a maize DNA sequence encoding a TIP41-like protein.

SEQ ID NO:76 shows a maize DNA sequence encoding an invertase protein.

SEQ ID NO:77 shows an *Escherichia coli* DNA sequence encoding an SpnR protein.

DETAILED DESCRIPTION

I. Overview of Several Embodiments

Disclosed herein are methods and compositions for genetic control of coleopteran pest infestations. Methods for identifying one or more gene(s) essential to the lifecycle of a coleopteran pest for use as a target gene for RNAi-mediated control of a coleopteran pest population are also provided. DNA plasmid vectors encoding one or more dsRNA molecules may be designed to suppress one or more target gene(s) essential for growth, survival, development, and/or reproduction. In some embodiments, methods are provided for post-transcriptional repression of expression or inhibition of a target gene via nucleic acid molecules that are complementary to a coding or non-coding sequence of the target gene in a coleopteran pest. In these and further embodiments, a coleopteran pest may ingest one or more dsRNA, siRNA, miRNA, and/or hpRNA molecules transcribed from all or a portion of a nucleic acid molecule that is complementary to a coding or non-coding sequence of a target gene, thereby providing a plant-protective effect.

Thus, some embodiments involve sequence-specific inhibition of expression of target gene products, using dsRNA, siRNA, miRNA and/or hpRNA that is complementary to coding and/or non-coding sequences of the target gene(s) to achieve at least partial control of a coleopteran pest. Disclosed is a set of isolated and purified nucleic acid molecules comprising a nucleotide sequence, for example, as set forth in SEQ ID NO:1, and fragments thereof. In some embodiments, a stabilized dsRNA molecule may be expressed from this sequence, fragments thereof, or a gene comprising this sequence, for the post-transcriptional silencing or inhibition of a target gene. In certain embodiments, isolated and purified nucleic acid molecules comprise all or part of SEQ ID NO:1.

Some embodiments involve a recombinant host cell (e.g., a plant cell) having in its genome at least one recombinant DNA sequence encoding at least one iRNA (e.g., dsRNA) molecule(s). In particular embodiments, the dsRNA molecule(s) may be produced when ingested by a coleopteran pest to post-transcriptionally silence or inhibit the expression of a target gene in the coleopteran pest. The recombinant DNA sequence may comprise, for example, SEQ ID NO:1, fragments of SEQ ID NO:1 (e.g., SEQ ID NOs: 21, 22, and 23), or a partial sequence of a gene comprising SEQ ID NO:1, or complements thereof.

Particular embodiments involve a recombinant host cell having in its genome a recombinant DNA sequence encoding at least one iRNA (e.g., dsRNA) molecule(s) comprising all or part of SEQ ID NO:1. When ingested by a coleopteran pest, the iRNA molecule(s) may silence or inhibit the expression of a target gene comprising all or part of SEQ ID NO:1 in the coleopteran pest, and thereby result in cessation of growth, development, reproduction, and/or feeding in the coleopteran pest.

In some embodiments, a recombinant host cell having in its genome at least one recombinant DNA sequence encoding at least one dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, including commodity products, are all provided, each of which comprises recombinant DNA sequence(s). In particular embodiments, a dsRNA molecule of the invention may be expressed in a transgenic plant cell. Therefore, in these and other embodiments, a dsRNA molecule of the invention may be isolated from a transgenic plant cell. In particular embodiments, the transgenic plant is a plant selected from the group comprising corn (*Zea mays*), soybean (*Glycine max*), and plants of the family Poaceae.

Some embodiments involve a method for modulating the expression of a target gene in a coleopteran pest cell. In these and other embodiments, a nucleic acid molecule may be provided, wherein the nucleic acid molecule comprises a nucleotide sequence encoding a dsRNA molecule. In particular embodiments, a nucleotide sequence encoding a dsRNA molecule may be operatively linked to a promoter, and may also be operatively linked to a transcription termination sequence. In particular embodiments, a method for modulating the expression of a target gene in a coleopteran pest cell may comprise: (a) transforming a plant cell with a vector comprising a nucleotide sequence encoding a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the dsRNA molecule encoded by the nucleotide sequence of the vector. A plant may be regenerated from a plant cell that has the vector integrated in its genome and comprises the dsRNA molecule encoded by the nucleotide sequence of the vector.

Thus, also disclosed is a transgenic plant comprising a vector having a nucleotide sequence encoding a dsRNA molecule integrated in its genome, wherein the transgenic plant comprises the dsRNA molecule encoded by the nucleotide sequence of the vector. In particular embodiments, expression of a dsRNA molecule in the plant is sufficient to modulate the expression of a target gene in a cell of a coleopteran pest that contacts the transformed plant or plant cell, for example, by feeding on the transformed plant, a part of the plant (e.g., root) or plant cell. Transgenic plants disclosed herein may display resistance and/or enhanced tolerance to coleopteran pest infestations. Particular transgenic plants may display resistance and/or enhanced tolerance to one or more coleopteran pests selected from the group consisting of: WCR; NCR; SCR; MCR; *D. balteata* LeConte; *D. u. tenella*; and *D. u. undecimpunctata* Mannerheim.

Also disclosed herein are methods for delivery of control agents, such as an iRNA molecule, to a coleopteran pest. Such control agents may cause, directly or indirectly, an impairment in the ability of the coleopteran pest to feed, grow or otherwise cause damage in a host. In some embodiments, a method is provided comprising delivery of a stabilized dsRNA molecule to a coleopteran pest to suppress at least one target gene in the coleopteran pest, thereby reducing or eliminating plant damage by a coleopteran pest. In some embodiments, a method of inhibiting expression of a target gene in a coleopteran pest may result in the cessation of growth, development, reproduction, and/or feeding in the coleopteran pest. In some embodiments, the method may eventually result in death of the coleopteran pest.

In some embodiments, compositions (e.g., a topical composition) are provided that comprise an iRNA (e.g., dsRNA) molecule of the invention for use in plants, animals, and/or the environment of a plant or animal to achieve the elimination or reduction of a coleopteran pest infestation. In particular embodiments, the composition may be a nutritional composition or food source to be fed to the coleopteran pest. Some embodiments comprise making the nutritional composition or food source available to the coleopteran pest. Ingestion of a composition comprising iRNA molecules may result in the uptake of the molecules by one or more cells of the coleopteran pest, which may in turn result in the inhibition of expression of at least one target gene in cell(s) of the coleopteran pest. Ingestion of or damage to a plant or plant cell by a coleopteran pest may be limited or eliminated in or on any host tissue or environment in which the coleopteran pest is present by providing one or more compositions comprising an iRNA molecule of the invention in the host of the coleopteran pest.

The compositions and methods disclosed herein may be used together in combinations with other methods and compositions for controlling damage by coleopteran pests. For example, an iRNA molecule as described herein for protecting plants from coleopteran pests may be used in a method comprising the additional use of one or more chemical agents effective against a coleopteran pest, biopesticides effective against a coleopteran pest, crop rotation, or recombinant genetic techniques that exhibit features different from the features of the RNAi-mediated methods and RNAi compositions of the invention (e.g., other RNAi compositions and/or recombinant production of proteins in plants that are harmful to a coleopteran pest (e.g., Bt toxins)).

II. Abbreviations dsRNA double-stranded ribonucleic acid
GI growth inhibition
NCBI National Center for Biotechnology Information
gDNA genomic DNA
iRNA inhibitory ribonucleic acid
ORF open reading frame
RNAi ribonucleic acid interference
miRNA micro inhibitory ribonucleic acid
siRNA small inhibitory ribonucleic acid
hpRNA hairpin ribonucleic acid
UTR untranslated region
WCR western corn rootworm (*Diabrotica virgifera virgifera* LeConte)
NCR northern corn rootworm (*Diabrotica barberi* Smith and Lawrence)
MCR Mexican corn rootworm (*Diabrotica virgifera zeae* Krysan and Smith)
PCR Polymerase chain reaction
RISC RNA-induced Silencing Complex
SCR southern corn rootworm (*Diabrotica undecimpunctata howardi* Barber)

III. Terms

In the description and tables which follow, a number of terms are used. In order to provide a clear and consistent understanding of the specification and claims, including the scope to be given such terms, the following definitions are provided:

Coleopteran pest: As used herein, the term "coleopteran pest" refers to insects of the genus *Diabrotica*, which feed upon corn and other true grasses. In particular examples, a coleopteran pest is selected from the list comprising *D. v. virgifera* LeConte (WCR); *D. barberi* Smith and Lawrence (NCR); *D. u. howardi* (SCR); *D. v. zeae* (MCR); *D. balteata* LeConte; *D. u. tenella*; and *D. u. undecimpunctata* Mannerheim.

Contact (with an organism): As used herein, the term "contact with" or "uptake by" an organism (e.g., a coleopteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; and soaking of organisms with a solution comprising the nucleic acid molecule.

Contig: As used herein the term "contig" refers to a DNA sequence that is reconstructed from a set of overlapping DNA segments derived from a single genetic source.

Corn plant: As used herein, the term "corn plant" refers to a plant of the species, *Zea mays* (maize).

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern blot, RT-PCR, western blot, or in vitro, in situ, or in vivo protein activity assay(s).

Encoding a dsRNA: As used herein, the term "encoding a dsRNA" includes a gene whose RNA transcription product is capable of forming an intramolecular dsRNA structure (e.g., a hairpin) or intermolecular dsRNA structure (e.g., by hybridizing to a target RNA molecule).

Genetic material: As used herein, the term "genetic material" includes all genes, and nucleic acid molecules, such as DNA and RNA.

Inhibition: As used herein, the term "inhibition", when used to describe an effect on a coding sequence (for example, a gene), refers to a measurable decrease in the cellular level of mRNA transcribed from the coding sequence and/or peptide, polypeptide, or protein product of the coding sequence. In some examples, expression of a coding sequence may be inhibited such that expression is approximately eliminated. "Specific inhibition" refers to the inhibition of a target coding sequence without consequently affecting expression of other coding sequences (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The nucleotide sequence of a nucleic acid molecule is read from the 5' to the 3' end of the molecule by convention. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

"Nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNAs, whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment", or more generally "segment", will be understood by those in the art as a functional term that includes both genomic sequences, ribosomal RNA sequences, transfer RNA sequences, messenger RNA sequences, operon sequences, and smaller engineered nucleotide sequences that encode or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of DNA and RNA (reverse transcribed into a cDNA) sequences. In PCR, the oligonucleotide is typically referred to as a "primer", which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence", "structural nucleotide sequence", or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome" as it applies to bacteria refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity", as used herein in the context of two nucleic acid or polypeptide sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an antiparallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization will determine the stringency of hybridization. The ionic strength of the wash buffer, the wash temperature, and wash duration also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 20% mismatch between the hybridization molecule and a homologous sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

Moderate Stringency condition (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology", with regard to a contiguous nucleic acid sequence, refers to contiguous nucleotide sequences that are borne by molecules that hybridize under stringent conditions to a molecule having the reference nucleic acid sequence. For example, nucleic acid molecules having sequences that are substantially homologous to a reference nucleic acid sequence of SEQ ID NO:1 are those nucleic acid sequences molecules that hybridize under stringent conditions (e.g., the Moderate Stringency conditions set forth, supra) to nucleic acid molecules having the reference nucleic acid sequence of SEQ ID NO:1. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

Operably linked: A first nucleotide sequence is operably linked with a second nucleic acid sequence when the first nucleic acid sequence is in a functional relationship with the second nucleic acid sequence. When recombinantly produced, operably linked nucleic acid sequences are generally contiguous, and, where necessary, two protein-coding regions may be joined in the same reading frame (e.g., in a translationally fused ORF). However, nucleic acids need not be contiguous to be operably linked.

The term, "operably linked", when used in reference to a regulatory sequence and a coding sequence, means that the regulatory sequence affects the expression of the linked coding sequence. "Regulatory sequences", or "control elements", refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most tissue or cell types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that respond to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: Promoters from plant viruses, such as the 35S promoter from Cauliflower Mosaic Virus (CaMV); promoters from rice actin genes; ubiquitin promoters; pEMU; MAS; maize H3 histone promoter; and the ALS promoter, XbaI/NcoI fragment 5' to the *Brassica napus* ALS3 structural gene (or a nucleotide sequence similar to said XbaI/NcoI fragment) (International PCT Publication No. WO96/30530).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: A seed-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Felgner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Transgene: An exogenous nucleic acid sequence. In some examples, a transgene may be a sequence that encodes one or both strand(s) of a dsRNA molecule that comprises a nucleotide sequence that is complementary to a nucleic acid molecule found in a coleopteran pest. In further examples, a transgene may be an antisense nucleic acid sequence, wherein expression of the antisense nucleic acid sequence inhibits expression of a target nucleic acid sequence. In still further examples, a transgene may be a gene sequence (e.g., a herbicide-resistance gene), a gene encoding an industrially or pharmaceutically useful compound, or a gene encoding a desirable agricultural trait. In these and other examples, a transgene may contain regulatory sequences operably linked to a coding sequence of the transgene (e.g., a promoter).

Vector: A nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also include one or more genes, antisense sequences, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% to 115% or greater relative to the yield of check varieties in the same growing location containing significant densities of coleopteran pests that are injurious to that crop growing at the same time and under the same conditions.

Unless specifically indicated or implied, the terms "a", "an", and "the" signify "at least one" as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a Coleopteran Pest Sequence

A. Overview

Described herein are nucleic acid molecules useful for the control of coleopteran pests. Described nucleic acid molecules include target sequences (e.g., native genes, and non-coding sequences), dsRNAs, siRNAs, hpRNAs, and miRNAs. For example, dsRNA, siRNA, miRNA and/or hpRNA molecules are described in some embodiments that may be specifically complementary to all or part of one or more native nucleic acid sequences in a coleopteran pest. In these and further embodiments, the native nucleic acid sequence(s) may be one or more target gene(s), the product of which may be, for example and without limitation: involved in a metabolic process; involved in a reproductive process; or involved in larval development. Nucleic acid molecules described herein, when introduced into a cell comprising at least one native nucleic acid sequence(s) to which the nucleic acid molecules are specifically complementary, may initiate RNAi in the cell, and consequently reduce or eliminate expression of the native nucleic acid sequence(s). In some examples, reduction or elimination of the expression of a target gene by a nucleic acid molecule comprising a sequence specifically complementary thereto may be lethal in coleopteran pests, or result in reduced growth and/or reproduction.

In some embodiments, at least one target gene in a coleopteran pest may be selected, wherein the target gene comprises nucleotide sequence reptin (SEQ ID NO:1), or a portion thereof, including but not limited to SEQ ID NOs: 21, 22, and 23. In particular examples, a target gene in a coleopteran pest is selected, wherein the target gene comprises novel nucleotide sequence reptin (SEQ ID NO:1), or a portion thereof, including but not limited to SEQ ID NOs: 21, 22, and 23.

In some embodiments, a target gene may be a nucleic acid molecule comprising a nucleotide sequence that encodes a polypeptide comprising a contiguous amino acid sequence that is at least 85% identical (e.g., about 90%, about 95%, about 96%, about 97%, about 98%, about 99%, about 100%, or 100% identical) to the amino acid sequence of a protein product of reptin (SEQ ID NO:1), such as, for example a protein product comprising SEQ ID NO:2. A target gene may be any nucleic acid sequence in a coleopteran pest, the post-transcriptional inhibition of which has a deleterious effect on the coleopteran pest, or provides a protective benefit against the coleopteran pest to a plant. In particular examples, a target gene is a nucleic acid molecule comprising a nucleotide sequence that encodes a polypeptide comprising a contiguous amino acid sequence that is at least 85% identical, about 90% identical, about 95% identical, about 96% identical, about 97% identical, about 98% identical, about 99% identical, about 100% identical, or 100% identical to the amino acid sequence of a protein product of novel nucleotide sequence SEQ ID NO:1.

Provided according to the invention are nucleotide sequences, the expression of which results in an RNA molecule comprising a nucleotide sequence that is specifically complementary to all or part of a native RNA molecule that is encoded by a coding sequence in a coleopteran pest. In some embodiments, after ingestion of the expressed RNA molecule by a coleopteran pest, down-regulation of the coding sequence in cells of the coleopteran pest may be obtained. In particular embodiments, down-regulation of the coding sequence in cells of the coleopteran pest may result in a deleterious effect on the growth, viability, proliferation, and/or reproduction of the coleopteran pest.

In some embodiments, target sequences include transcribed non-coding RNA sequences, such as 5'UTRs; 3'UTRs; spliced leader sequences; intron sequences; outron sequences (e.g., 5'UTR RNA subsequently modified in trans splicing); donatron sequences (e.g., non-coding RNA required to provide donor sequences for trans splicing); and other non-coding transcribed RNA of target coleopteran pest genes. Such sequences may be derived from both mono-cistronic and poly-cistronic genes.

Thus, also described herein in connection with some embodiments are iRNA molecules (e.g., dsRNAs, siRNAs, miRNAs and hpRNAs) that comprise at least one nucleotide sequence that is specifically complementary to all or part of a target sequence in a coleopteran pest. In some embodiments an iRNA molecule may comprise nucleotide sequence(s) that are complementary to all or part of a plurality of target sequences; for example, 2, 3, 4, 5, 6, 7, 8, 9, 10, or more target sequences. In particular embodiments, an iRNA molecule may be produced in vitro, or in vivo by a genetically-modified organism, such as a plant or bacterium. Also disclosed are cDNA sequences that may be used for the production of dsRNA molecules, siRNA molecules, miRNA and/or hpRNA molecules that are specifically complementary to all or part of a target sequence in a coleopteran pest. Further described are recombinant DNA constructs for use in achieving stable transformation of particular host targets. Transformed host targets may express effective levels of dsRNA, siRNA, miRNA and/or hpRNA molecules from the recombinant DNA constructs. Therefore, also described is a plant transformation vector comprising at least one nucleotide sequence operably linked to a heterologous promoter functional in a plant cell, wherein expression of the nucleotide sequence(s) results in an RNA molecule comprising a nucleotide sequence that is specifically complementary to all or part of a target sequence in a coleopteran pest.

In some embodiments, nucleic acid molecules useful for the control of coleopteran pests may include: all or part of a native nucleic acid sequence isolated from *Diabrotica* comprising reptin (SEQ ID NO:1); nucleotide sequences that when expressed result in an RNA molecule comprising a nucleotide sequence that is specifically complementary to all or part of a native RNA molecule comprising reptin (SEQ ID NO:1); iRNA molecules (e.g., dsRNAs, siRNAs, miRNAs and hpRNAs) that comprise at least one nucleotide sequence that is specifically complementary to all or part of nucleotide sequence reptin (SEQ ID NO:1); cDNA sequences that may be used for the production of dsRNA molecules, siRNA molecules, miRNA and/or hpRNA molecules that are specifically complementary to all or part of nucleotide sequence reptin (SEQ ID NO:1); and recombinant DNA constructs for use in achieving stable transformation of particular host targets, wherein a transformed host target comprises one or more of the foregoing nucleic acid molecules.

B. Nucleic Acid Molecules

The present invention provides, inter alia, iRNA (e.g., dsRNA, siRNA, miRNA and hpRNA) molecules that inhibit target gene expression in a cell, tissue, or organ of a coleopteran pest; and DNA molecules capable of being expressed as an iRNA molecule in a cell or microorganism to inhibit target gene expression in a cell, tissue, or organ of a coleopteran pest.

Some embodiments of the invention provide an isolated nucleic acid molecule comprising at least one (e.g., one, two, three, or more) nucleotide sequence(s) selected from the group consisting of: SEQ ID NOs:1, 21, 22, 23, or 24; the complement of SEQ ID NOs:1, 21, 22, 23, or 24; a fragment of at least 19 contiguous nucleotides of SEQ ID NOs:1, 21, 22, 23, or 24; the complement of a fragment of at least 19 contiguous nucleotides of SEQ ID NOs:1, 21, 22, 23, or 24; a native coding sequence of a *Diabrotica* organism (e.g., WCR) comprising SEQ ID NOs:1, 21, 22, 23, or 24; the complement of a native coding sequence of a *Diabrotica* organism comprising SEQ ID NOs:1, 21, 22, 23, or 24; a native non-coding sequence of a *Diabrotica* organism that is transcribed into a native RNA molecule comprising SEQ ID NOs:1, 21, 22, 23, or 24; the complement of a native non-coding sequence of a *Diabrotica* organism that is transcribed into a native RNA molecule comprising SEQ ID NOs:1, 21, 22, 23, or 24; a fragment of at least 19 contiguous nucleotides of a native coding sequence of a *Diabrotica* organism comprising SEQ ID NOs:1, 21, 22, 23, or 24; the complement of a fragment of at least 19 contiguous nucleotides of a native coding sequence of a *Diabrotica* organism comprising SEQ ID NOs:1, 21, 22, 23, or 24; a fragment of at least 19 contiguous nucleotides of a native non-coding sequence of a *Diabrotica* organism that is transcribed into a native RNA molecule comprising SEQ ID NOs:1, 21, 22, 23, or 24; and the complement of a fragment of at least 19 contiguous nucleotides of a native non-coding sequence of a *Diabrotica* organism that is transcribed into a native RNA molecule comprising SEQ ID NOs:1, 21, 22, 23, or 24. In particular embodiments, contact with or uptake by a coleopteran pest of the isolated nucleic acid sequence inhibits the growth, development, reproduction and/or feeding of the coleopteran pest.

In some embodiments, a nucleic acid molecule of the invention may comprise at least one (e.g., one, two, three, or more) DNA sequence(s) capable of being expressed as an iRNA molecule in a cell or microorganism to inhibit target gene expression in a cell, tissue, or organ of a coleopteran pest. Such DNA sequence(s) may be operably linked to a promoter sequence that functions in a cell comprising the DNA molecule to initiate or enhance the transcription of the encoded RNA capable of forming a dsRNA molecule(s). In one embodiment, the at least one (e.g., one, two, three, or more) DNA sequence(s) may be derived from nucleotide sequence SEQ ID NO:1. Derivatives of SEQ ID NO:1 include fragments of SEQ ID NO:1, including but not limited to SEQ ID NOs: 21, 22, and 23. In some embodiments, such a fragment may comprise, for example, at least about 19 contiguous nucleotides of SEQ ID NO:1, or a complement thereof. Thus, such a fragment may comprise, for example, 19, 20, 21, 22, 23, 24, 25, 26, 27, 28, 29, or 30 contiguous nucleotides of SEQ ID NO:1, or a complement thereof. In these and further embodiments, such a fragment may comprise, for example, more than about 19 contiguous nucleotides of SEQ ID NO:1, or a complement thereof. Thus, a fragment of SEQ ID NO:1 may comprise, for example, 19, 20, 21, about 25, (e.g., 22, 23, 24, 25, 26, 27, 28, and 29), about 30, about 40, (e.g., 35, 36, 37, 38, 39, 40, 41, 42, 43, 44, and 45), about 50, about 60, about 70, about 80, about 90, about 100, about 110, about 120, about 130, about 140, about 150, about 160, about 170, about 180, about 190, about 200 or more contiguous nucleotides of SEQ ID NO:1, or a complement thereof.

Some embodiments comprise introducing partial- or fully-stabilized dsRNA molecules into a coleopteran pest to inhibit expression of a target gene in a cell, tissue, or organ of the coleopteran pest. When expressed as an iRNA molecule (e.g., dsRNA, siRNA, miRNA, and hpRNA) and taken up by a coleopteran pest, nucleic acid sequences comprising one or more fragments of SEQ ID NO:1 may cause one or more of death, growth inhibition, change in sex ratio, reduction in brood size, cessation of infection, and/or cessation of feeding by a coleopteran pest. For example, in some embodiments, a dsRNA molecule comprising a nucleotide sequence including about 19 to about 300 nucleotides that are substantially homologous to a coleopteran pest target gene sequence and comprising one or more fragments of a nucleotide sequence comprising SEQ ID NO:1 is provided. Expression of such a dsRNA molecule may, for example, lead to mortality and/or growth inhibition in a coleopteran pest that takes up the dsRNA molecule.

In certain embodiments, dsRNA molecules provided by the invention comprise nucleotide sequences complementary to a target gene comprising SEQ ID NO:1 and/or nucleotide sequences complementary to a fragment of SEQ ID NO:1, the inhibition of which target gene in a coleopteran pest results in the reduction or removal of a protein or nucleotide sequence agent that is essential for the coleopteran pest's growth, development, or other biological function. A selected nucleotide sequence may exhibit from about 80% to about 100% sequence identity to SEQ ID NO:1, a contiguous fragment of the nucleotide sequence set forth in SEQ ID NO:1, or the complement of either of the foregoing. For example, a selected nucleotide sequence may exhibit about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to SEQ ID NO:1, a contiguous fragment of the nucleotide sequence set forth in SEQ ID NO:1, or the complement of either of the foregoing.

In some embodiments, a DNA molecule capable of being expressed as an iRNA molecule in a cell or microorganism to inhibit target gene expression may comprise a single nucleotide sequence that is specifically complementary to all or part of a native nucleic acid sequence found in one or more target coleopteran pest species, or the DNA molecule can be constructed as a chimera from a plurality of such specifically complementary sequences.

In some embodiments, a nucleic acid molecule may comprise a first and a second nucleotide sequence separated by a "spacer sequence". A spacer sequence may be a region comprising any sequence of nucleotides that facilitates secondary structure formation between the first and second nucleotide sequences, where this is desired. In one embodiment, the spacer sequence is part of a sense or antisense coding sequence for mRNA. The spacer sequence may alternatively comprise any combination of nucleotides or homologues thereof that are capable of being linked covalently to a nucleic acid molecule.

For example, in some embodiments, the DNA molecule may comprise a nucleotide sequence coding for one or more different RNA molecules, wherein each of the different RNA molecules comprises a first nucleotide sequence and a second nucleotide sequence, wherein the first and second nucleotide sequences are complementary to each other. The first and second nucleotide sequences may be connected within an RNA molecule by a spacer sequence. The spacer sequence may constitute part of the first nucleotide sequence or the second nucleotide sequence. Expression of an RNA molecule comprising the first and second nucleotide sequences may lead to the formation of a dsRNA molecule of the present invention, by specific base-pairing of the first and second nucleotide sequences. The first nucleotide sequence or the second nucleotide sequence may be substantially identical to a nucleic acid sequence native to a coleopteran pest (e.g., a target gene, or transcribed non-coding sequence), a derivative thereof, or a complementary sequence thereto.

dsRNA nucleic acid molecules comprise double strands of polymerized ribonucleotide sequences, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNAse III enzyme, such as DICER in eukaryotes, either in vitro or in vivo. See Elbashir et al. (2001) Nature 411:494-8; and Hamilton and Baulcombe (1999) Science 286(5441):950-2. DICER or functionally-equivalent RNAse III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNAse III enzymes are unwound and separated into single-stranded RNA in the cell. The siRNA molecules then specifically hybridize with RNA sequences transcribed from a target gene, and both RNA molecules are subsequently degraded by an inherent cellular RNA-degrading mechanism. This process may result in the effective degradation or removal of the RNA sequence encoded by the target gene in the target organism. The outcome is the post-transcriptional silencing of the targeted gene. In some embodiments, siRNA molecules produced by endogenous RNAse III enzymes from heterologous nucleic acid molecules may efficiently mediate the down-regulation of target genes in coleopteran pests.

In some embodiments, a nucleic acid molecule of the invention may include at least one non-naturally occurring nucleotide sequence that can be transcribed into a single-stranded RNA molecule capable of forming a dsRNA molecule in vivo through intermolecular hybridization. Such dsRNA sequences typically self-assemble, and can be provided in the nutrition source of a coleopteran pest to achieve the post-transcriptional inhibition of a target gene. In these and further embodiments, a nucleic acid molecule of the invention may comprise two different non-naturally occurring nucleotide sequences, each of which is specifically complementary to a different target gene in a coleopteran pest. When such a nucleic acid molecule is provided as a dsRNA molecule to a coleopteran pest, the dsRNA molecule inhibits the expression of at least two different target genes in the coleopteran pest.

C. Obtaining Nucleic Acid Molecules

A variety of native sequences in coleopteran pests may be used as target sequences for the design of nucleic acid molecules of the invention, such as iRNAs and DNA molecules encoding iRNAs. Selection of native sequences is not, however, a straight-forward process. Only a small number of native sequences in the coleopteran pest will be effective targets. For example, it cannot be predicted with certainty whether a particular native sequence can be effectively down-regulated by nucleic acid molecules of the invention, or whether down-regulation of a particular native sequence will have a detrimental effect on the growth, viability, proliferation, and/or reproduction of the coleopteran pest. The vast majority of native coleopteran pest sequences, such as ESTs isolated therefrom (for example, as listed in U.S. Pat. No. 7,612,194 and U.S. Pat. No. 7,943,819), do not have a detrimental effect on the growth, viability, proliferation, and/or reproduction of the coleopteran pest, such as WCR or NCR. Neither is it predictable which of the native sequences which may have a detrimental effect on a coleopteran pest are able to be used in recombinant techniques for expressing nucleic acid molecules complementary to such native sequences in a host plant and providing the detrimental effect on the coleopteran pest upon feeding without causing harm to the host plant.

In some embodiments, nucleic acid molecules of the invention (e.g., dsRNA molecules to be provided in the host plant of a coleopteran pest) are selected to target cDNA sequences that encode proteins or parts of proteins essential for coleopteran pest survival, such as amino acid sequences involved in metabolic or catabolic biochemical pathways, cell division, reproduction, energy metabolism, digestion, host plant recognition, and the like. As described herein, ingestion of compositions by a target organism containing one or more dsRNAs, at least one segment of which is specifically complementary to at least a substantially identical segment of RNA produced in the cells of the target pest organism, can result in the death or other inhibition of the target. A nucleotide sequence, either DNA or RNA, derived from a coleopteran pest can be used to construct plant cells resistant to infestation by the coleopteran pests. The host plant of the coleopteran pest (e.g., Z. mays or G. max), for example, can be transformed to contain one or more of the nucleotide sequences derived from the coleopteran pest as provided herein. The nucleotide sequence transformed into the host may encode one or more RNAs that form into a dsRNA sequence in the cells or biological fluids within the transformed host, thus making the dsRNA available if/when the coleopteran pest forms a nutritional relationship with the transgenic host. This may result in the suppression of expression of one or more genes in the cells of the coleopteran pest, and ultimately death or inhibition of its growth or development.

Thus, in some embodiments, a gene is targeted that is essentially involved in the growth, development and reproduction of a coleopteran pest. Other target genes for use in the present invention may include, for example, those that play important roles in coleopteran pest viability, movement, migration, growth, development, infectivity, establishment of feeding sites and reproduction. A target gene may therefore be a housekeeping gene or a transcription factor. Additionally, a native coleopteran pest nucleotide sequence for use in the present invention may also be derived from a homolog (e.g., an ortholog), of a plant, viral, bacterial or insect gene, the function of which is known to those of skill in the art, and the nucleotide sequence of which is specifically hybridizable with a target gene in the genome of the target coleopteran pest. Methods of identifying a homolog of a gene with a known nucleotide sequence by hybridization are known to those of skill in the art.

In some embodiments, the invention provides methods for obtaining a nucleic acid molecule comprising a nucleotide sequence for producing an iRNA (e.g., dsRNA, siRNA, miRNA, and hpRNA) molecule. One such embodiment comprises: (a) analyzing one or more target gene(s) for their expression, function, and phenotype upon dsRNA-mediated gene suppression in a coleopteran pest; (b) probing a cDNA or gDNA library with a probe comprising all or a portion of a nucleotide sequence or a homolog thereof from a targeted coleopteran pest that displays an altered (e.g., reduced) growth or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA sequence or a homolog thereof; and (f) chemically synthesizing all or a substantial portion of a gene sequence, or a siRNA or miRNA or hpRNA or mRNA or dsRNA.

In further embodiments, a method for obtaining a nucleic acid fragment comprising a nucleotide sequence for producing a substantial portion of an iRNA (e.g., dsRNA, siRNA, miRNA, and hpRNA) molecule includes: (a) synthesizing first and second oligonucleotide primers specifically complementary to a portion of a native nucleotide sequence from a targeted coleopteran pest; and (b) amplifying a cDNA or gDNA insert present in a cloning vector using the first and second oligonucleotide primers of step (a), wherein the amplified nucleic acid molecule comprises a substantial portion of a siRNA or miRNA or hpRNA or mRNA or dsRNA molecule.

Nucleic acids of the invention can be isolated, amplified, or produced by a number of approaches. For example, an iRNA (e.g., dsRNA, siRNA, miRNA, and hpRNA) molecule may be obtained by PCR amplification of a target nucleic acid sequence (e.g., a target gene or a target transcribed non-coding sequence) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P. E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,980,460, 4,725,677, 4,415,732, 4,458,066, and 4,973,679. Alternative chemistries resulting in non-natural backbone groups, such as phosphorothioate, phosphoramidate, and the like, can also be employed.

An RNA, dsRNA, siRNA, miRNA, or hpRNA molecule of the present invention may be produced chemically or enzymatically by one skilled in the art through manual or automated reactions, or in vivo in a cell comprising a nucleic acid molecule comprising a sequence encoding the RNA, dsRNA, siRNA, miRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of nucleotide sequences are known in the art. See, e.g., International PCT Publication No. WO97/32016; and U.S. Pat. Nos. 5,593,874, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in a coleopteran pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a nucleotide sequence that, upon expression to RNA and ingestion by a coleopteran pest, achieves suppression of a target gene in a cell, tissue, or organ of the coleopteran pest. Thus, some embodiments provide a recombinant nucleic acid molecule comprising a nucleic acid sequence capable of being expressed as an iRNA (e.g., dsRNA, siRNA, miRNA, and hpRNA) molecule in a plant cell to inhibit target gene expression in a coleopteran pest. In order to initiate or enhance expression, such recombinant nucleic acid molecules may comprise one or more regulatory sequences, which regulatory sequences may be operably linked to the nucleic acid sequence capable of being expressed as an iRNA. Methods to express a gene suppression molecule in plants are known, and may be used to express a nucleotide sequence of the present invention. See, e.g., International PCT Publication No. WO06/073727; and U.S. Patent Publication No. 2006/0200878 A1).

In specific embodiments, a recombinant DNA molecule of the invention may comprise a nucleic acid sequence encoding a dsRNA molecule. Such recombinant DNA molecules may encode dsRNA molecules capable of inhibiting the expression of endogenous target gene(s) in a coleopteran pest cell upon ingestion. In many embodiments, a transcribed RNA may form a dsRNA molecule that may be provided in a stabilized form; e.g., as a hairpin and stem and loop structure.

In these and further embodiments, one strand of a dsRNA molecule may be formed by transcription from a nucleotide sequence which is substantially homologous to nucleotide sequence SEQ ID NO:1; the complement of SEQ ID NO:1; a fragment of at least 19 contiguous nucleotides of SEQ ID NO:1 (e.g., SEQ ID NOs: 21, 22, 23 or a portion thereof); the complement of a fragment of at least 19 contiguous nucleotides of SEQ ID NO:1; a native coding sequence of a Diabrotica organism (e.g., WCR) comprising SEQ ID NO:1; the complement of a native coding sequence of a Diabrotica organism comprising SEQ ID NO:1; a native non-coding sequence of a Diabrotica organism that is transcribed into a native RNA molecule comprising SEQ ID NO:1; the complement of a native non-coding sequence of a Diabrotica organism that is transcribed into a native RNA molecule comprising SEQ ID NO:1; a fragment of at least 19 contiguous nucleotides of a native coding sequence of a Diabrotica organism (e.g., WCR) comprising SEQ ID NO:1; the complement of a fragment of at least 19 contiguous nucleotides of a native coding sequence of a Diabrotica organism comprising SEQ ID NO:1; a fragment of at least 19 contiguous nucleotides of a native non-coding sequence of a Diabrotica organism that is transcribed into a native RNA molecule comprising SEQ ID NO:1; and the complement of a fragment of at least 19 contiguous nucleotides of a native non-coding sequence of a Diabrotica organism that is transcribed into a native RNA molecule comprising SEQ ID NO:1.

In particular embodiments, a recombinant DNA molecule encoding a dsRNA molecule may comprise at least two nucleotide sequence segments within a transcribed sequence, such sequences arranged such that the transcribed sequence comprises a first nucleotide sequence segment in a sense orientation, and a second nucleotide sequence segment (comprising the complement of the first nucleotide sequence segment) is in an antisense orientation, relative to at least one promoter, wherein the sense nucleotide sequence segment and the antisense nucleotide sequence segment are linked or connected by a spacer sequence segment of from about five (~5) to about one thousand (~1000) nucleotides. The spacer sequence segment may form a loop between the sense and antisense sequence segments. The sense nucleotide sequence segment or the antisense nucleotide sequence segment may be substantially homologous to the nucleotide sequence of a target gene (e.g., a gene comprising SEQ ID NO:1) or fragment thereof. Exemplary dsRNA molecules of the present invention comprise SEQ ID NO:24. In some embodiments, however, a recombinant DNA molecule may encode a dsRNA molecule without a spacer sequence. In embodiments, a sense coding sequence and an antisense coding sequence may be of different lengths.

Sequences identified as having a deleterious effect on coleopteran pests or a plant-protective effect with regard to coleopteran pests may be readily incorporated into expressed dsRNA molecules through the creation of appropriate expression cassettes in a recombinant nucleic acid molecule of the invention. For example, such sequences may be expressed as a hairpin with stem and loop structure by taking a first segment corresponding to a target gene sequence (e.g., SEQ ID NO:1, and fragments thereof); linking this sequence to a second segment spacer region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms and comprises the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native coleopteran pest sequence is enhanced by co-expression of a fragment of the targeted gene, for instance on an additional plant expressible cassette, that leads to enhanced siRNA production, or reduces methylation to prevent transcriptional gene silencing of the dsRNA hairpin promoter. Exemplary of such dsRNA molecules of the present invention include hairpin molecules comprising SEQ ID NO:24.

Embodiments of the invention include introduction of a recombinant nucleic acid molecule of the present invention into a plant (i.e., transformation) to achieve coleopteran pest-inhibitory levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acid sequences of the invention can, for example, be suitably inserted into a vector under the control of a suitable promoter that functions in one or more hosts to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart coleopteran pest resistance to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a nucleotide sequence that is substantially homologous and specifically hybridizable to a corresponding transcribed nucleotide sequence within a coleopteran pest that may cause damage to the host plant species. The coleopteran pest may contact the iRNA molecule that is transcribed in cells of the transgenic host plant, for example, by ingesting cells or fluids of the transgenic host plant that comprise the iRNA molecule. Thus, expression of a target gene is suppressed by the iRNA molecule within coleopteran pests that infest the transgenic host plant. In some embodiments, suppression of expression of the target gene in the target coleopteran pest may result in the plant being resistant to attack by the pest.

In order to enable delivery of iRNA molecules to a coleopteran pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a nucleotide sequence of the invention operably linked to one or more regulatory sequences, such as a heterologous promoter sequence that functions in a host cell, such as a bacterial cell wherein the nucleic acid molecule is to be amplified, and a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (CaMV 35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140, 078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. Patent Publication No. 2009/757,089 (maize chloroplast aldolase promoter). Additional promoters include the nopaline synthase (NOS) promoter (Ebert et al. (1987) Proc. Natl. Acad. Sci. USA 84(16):5745-9) and the octopine synthase (OCS) promoters (which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus $^{35}$S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV 35S (U.S. Pat. Nos. 5,322,938, 5,352,605, 5,359,142, and 5,530,196); FMV 35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank™ Accession No. V00087; Depicker et al. (1982) J. Mol. Appl. Genet. 1:561-73; Bevan et al. (1983) Nature 304:184-7).

In particular embodiments, nucleic acid molecules of the invention comprise a tissue-specific promoter, such as a root-specific promoter. Root-specific promoters drive expression of operably-linked coding sequences exclusively or preferentially in root tissue. Examples of root-specific promoters are known in the art. See, e.g., U.S. Pat. Nos. 5,110,732; 5,459,252 and 5,837,848; and Opperman et al. (1994) Science 263:221-3; and Hirel et al. (1992) Plant Mol. Biol. 20:207-18. In some embodiments, a nucleotide sequence or fragment for coleopteran pest control according to the invention may be cloned between two root-specific promoters oriented in opposite transcriptional directions relative to the nucleotide sequence or fragment, and which are operable in a transgenic plant cell and expressed therein to produce RNA molecules in the transgenic plant cell that subsequently may form dsRNA molecules, as described, supra. The iRNA molecules expressed in plant tissues may be ingested by a coleopteran pest so that suppression of target gene expression is achieved.

Additional regulatory sequences that may optionally be operably linked to a nucleic acid molecule of interest include 5'UTRs that function as a translation leader sequence located between a promoter sequence and a coding sequence. The translation leader sequence is present in the fully-processed mRNA, and it may affect processing of the primary transcript, and/or RNA stability. Examples of translation leader sequences include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5'UTRs include GmHsp (U.S. Pat. No. 5,659,122); PhDnaK (U.S. Pat. No. 5,362,865); AtAnt1; TEV (Carrington and Freed (1990) J. Virol. 64:1590-7); and AGRtunos (GenBank™ Accession No. V00087; and Bevan et al. (1983) Nature 304:184-7).

Additional regulatory sequences that may optionally be operably linked to a nucleic acid molecule of interest also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank™ Accession No. E01312).

Some embodiments may include a plant transformation vector that comprises an isolated and purified DNA molecule comprising at least one of the above-described regulatory sequences operatively linked to one or more nucleotide sequences of the present invention. When expressed, the one or more nucleotide sequences result in one or more RNA molecule(s) comprising a nucleotide sequence that is specifically complementary to all or part of a native RNA molecule in a coleopteran pest. Thus, the nucleotide sequence(s) may comprise a segment encoding all or part of a ribonucleotide sequence present within a targeted coleopteran pest RNA transcript, and may comprise inverted repeats of all or a part of a targeted coleopteran pest transcript. A plant transformation vector may contain sequences specifically complementary to more than one target sequence, thus allowing production of more than one dsRNA for inhibiting expression of two or more genes in cells of one or more populations or species of target coleopteran pests. Segments of nucleotide sequence specifically complementary to nucleotide sequences present in different genes can be combined into a single composite nucleic acid molecule for expression in a transgenic plant. Such segments may be contiguous or separated by a spacer sequence.

In some embodiments, a plasmid of the present invention already containing at least one nucleotide sequence(s) of the invention can be modified by the sequential insertion of additional nucleotide sequence(s) in the same plasmid, wherein the additional nucleotide sequence(s) are operably linked to the same regulatory elements as the original at least one nucleotide sequence(s). In some embodiments, a nucleic acid molecule may be designed for the inhibition of multiple target genes. In some embodiments, the multiple genes to be inhibited can be obtained from the same coleopteran pest species, which may enhance the effectiveness of the nucleic acid molecule. In other embodiments, the genes can be derived from different coleopteran pests, which may broaden the range of coleopteran pests against which the agent(s) is/are effective. When multiple genes are targeted for suppression or a combination of expression and suppression, a polycistronic DNA element can be fabricated.

A recombinant nucleic acid molecule or vector of the present invention may comprise a selectable marker that confers a selectable phenotype on a transformed cell, such as a plant cell. Selectable markers may also be used to select for plants or plant cells that comprise a recombinant nucleic acid molecule of the invention. The marker may encode biocide resistance, antibiotic resistance (e.g., kanamycin, Geneticin (G418), bleomycin, hygromycin, etc.), or herbicide resistance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate resistance; a nitrilase gene which confers resistance to bromoxynil; a mutant acetolactate synthase (ALS) gene which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18$^{th}$ *Stadler Genetics Symposium*, P. Gustafson and R. Appels, eds. (New York: Plenum), pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); an xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to coleopteran pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by *Agrobacterium*-mediated transformation (See, e.g., U.S. Pat. Nos. 5,563,055; 5,591,616; 5,693,512; 5,824,877; 5,981,840; and 6,384,301) and by acceleration of DNA-coated particles (See, e.g., U.S. Pat. Nos. 5,015,580; 5,550,318; 5,538,880; 6,160,208; 6,399,861; and 6,403,865), etc. Techniques that are particularly useful for transforming corn are described, for example, in U.S. Pat. Nos. 7,060,876 and 5,591,616; and International PCT Publication WO95/06722. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences encoding one or more iRNA molecules in the genome of the transgenic plant.

The most widely utilized method for introducing an expression vector into plants is based on the natural transformation system of various *Agrobacterium* species. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. The Ti (tumor-inducing)-plasmids contain a large segment, known as T-DNA, which is transferred to transformed plants. Another segment of the Ti plasmid, the Vir region, is responsible for T-DNA transfer. The T-DNA region is bordered by terminal repeats. In modified binary vectors, the tumor-inducing genes have been deleted, and the functions of the Vir region are utilized to transfer foreign DNA bordered by the T-DNA border sequences. The T-region may also contain a selectable marker for efficient recovery of transgenic cells and plants, and a multiple cloning site for inserting sequences for transfer such as a dsRNA encoding nucleic acid.

Thus, in some embodiments, a plant transformation vector is derived from a Ti plasmid of *A. tumefaciens* (See, e.g., U.S. Pat. Nos. 4,536,475, 4,693,977, 4,886,937, and 5,501,967; and European Patent No. EP 0 122 791) or a Ri plasmid of *A. rhizogenes*. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent No. EP 0 120 516, and those derived from any of the foregoing. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA sequence encoding one or more iRNA molecules that inhibit target gene expression in a coleopteran pest) in the regenerating plants, a variety of assays may be performed. Such assays include, for example: molecular biological assays, such as Southern and northern blotting, PCR, and nucleic acid sequencing; biochemical assays, such as detecting the presence of a protein product, e.g., by immunological means (ELISA and/or immuno blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species (e.g., *Z. mays* or *G. max*) or tissue type, including cell cultures.

A transgenic plant formed using *Agrobacterium*-dependent transformation methods typically contains a single recombinant DNA sequence inserted into one chromosome. The single recombinant DNA sequence is referred to as a "transgenic event" or "integration event". Such transgenic plants are hemizygous for the inserted exogenous sequence. In some embodiments, a transgenic plant homozygous with respect to a transgene may be obtained by sexually mating (selfing) an independent segregant transgenic plant that contains a single exogenous gene sequence to itself, for example a $T_0$ plant, to produce $T_1$ seed. One fourth of the $T_1$ seed produced will be homozygous with respect to the transgene. Germinating $T_1$ seed results in plants that can be tested for heterozygosity, typically using an SNP assay or a thermal amplification assay that allows for the distinction between heterozygotes and homozygotes (i.e., a zygosity assay).

In particular embodiments, at least 2, 3, 4, 5, 6, 7, 8, 9 or 10 or more different iRNA molecules that have a coleopteran pest-inhibitory effect are produced in a plant cell. The iRNA molecules (e.g., dsRNA molecules) may be expressed from multiple nucleic acid sequences introduced in different transformation events, or from a single nucleic acid sequence introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple nucleic acid sequences that are each homologous to different loci within one or more coleopteran pests (for example, the locus defined by SEQ ID NO:1), both in different populations of the same species of coleopteran pest, or in different species of coleopteran pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a nucleotide sequence that encodes an iRNA molecule may be introduced into a first plant line that is amenable to transformation to produce a transgenic plant, which transgenic plant may be crossed with a second plant line to introgress the nucleotide sequence that encodes the iRNA molecule into the second plant line.

The invention also includes commodity products containing one or more of the sequences of the present invention. Particular embodiments include commodity products produced from a recombinant plant or seed containing one or more of the nucleotide sequences of the present invention. A commodity product containing one or more of the sequences of the present invention is intended to include, but not be limited to, meals, oils, crushed or whole grains or seeds of a plant, or any food or animal feed product comprising any meal, oil, or crushed or whole grain of a recombinant plant or seed containing one or more of the sequences of the present invention. The detection of one or more of the sequences of the present invention in one or more commodity or commodity products contemplated herein is de facto evidence that the commodity or commodity product is produced from a transgenic plant designed to express one or more of the nucleotides sequences of the present invention for the purpose of controlling coleopteran plant pests using dsRNA-mediated gene suppression methods.

In some aspects, seeds and commodity products produced by transgenic plants derived from transformed plant cells are included, wherein the seeds or commodity products comprise a detectable amount of a nucleic acid sequence of the invention. In some embodiments, such commodity products may be produced, for example, by obtaining transgenic plants and preparing food or feed from them. Commodity products comprising one or more of the nucleic acid sequences of the invention includes, for example and without limitation: meals, oils, crushed or whole grains or seeds of a plant, and any food product comprising any meal, oil, or crushed or whole grain of a recombinant plant or seed comprising one or more of the nucleic acid sequences of the invention. The detection of one or more of the sequences of the invention in one or more commodity or commodity products is de facto evidence that the commodity or commodity product is produced from a transgenic plant designed to express one or more of the iRNA molecules of the invention for the purpose of controlling coleopteran pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a coleopteran pest other than the one defined by SEQ ID NO:1, such as, for example, Cafl-180 (PCT International Application No. PCT/US2011/068062 (filed Dec. 30, 2011)), VatpaseC (PCT International Application No. PCT/US2011/068144 (filed Dec. 30, 2011)), VatpaseH (PCT International Application No. PCT/US2011/068162 (filed Dec. 30, 2011)) or Rho1 (PCT International Application No. PCT/US2011/068188 (filed Dec. 30, 2011)); a transgenic event from which is transcribed an iRNA molecule targeting a gene in an organism other than a coleopteran pest (e.g., a plant-parasitic nematode); a gene encoding an insecticidal protein (e.g., a *Bacillus thuringiensis* insecticidal protein, such as, for example, Cry34Ab1 (U.S. Pat. Nos. 6,127,180, 6,624,145 and 6,340,593), Cry35Ab1 (U.S. Pat. Nos. 6,083, 499, 6,548,291 and 6,340,593), a "Cry34/35Ab1" combination in a single event (e.g., maize event DAS-59122-7; U.S. Pat. No. 7,323,556), Cry3A (e.g., U.S. Pat. No. 7,230,167), Cry3B (e.g., PCT International Application No. PCT/ US1999/018883), Cry6A (e.g., U.S. Pat. No. 6,831,062), and combinations thereof (e.g., PCT International Application Nos. PCT/US11/033,618 (filed Apr. 15, 2011), PCT/US11/033,618 (filed Apr. 22, 2011) and PCT/US11/033,617 (filed Apr. 22, 2011)); an herbicide tolerance gene (e.g., a gene providing tolerance to glyphosate, glufosinate, dicamba or 2,4-D (e.g., U.S. Pat. No. 7,838,733)); and a gene contributing to a desirable phenotype in the transgenic plant, such as increased yield, altered fatty acid metabolism, or restoration of cytoplasmic male sterility). In particular embodiments, sequences encoding iRNA molecules of the invention may be combined with other insect control or with disease resistance traits in a plant to achieve desired traits for enhanced control of insect damage and plant disease. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in a Coleopteran Pest

A. Overview

In some embodiments of the invention, at least one nucleic acid molecule useful for the control of coleopteran pests may be provided to a coleopteran pest, wherein the nucleic acid molecule leads to RNAi-mediated gene silencing in the coleopteran pest. In particular embodiments, an iRNA molecule (e.g., dsRNA, siRNA, miRNA, and hpRNA) may be provided to the coleopteran pest. In some embodiments, a nucleic acid molecule useful for the control of coleopteran pests may be provided to a coleopteran pest by contacting the nucleic acid molecule with the coleopteran pest. In these and further embodiments, a nucleic acid molecule useful for the control of coleopteran pests may be provided in a feeding substrate of the coleopteran pest, for example, a nutritional composition. In these and further embodiments, a nucleic acid molecule useful for the control of coleopteran pests may be provided through ingestion of plant material comprising the nucleic acid molecule that is ingested by the coleopteran pest. In certain embodiments, the nucleic acid molecule is present in plant material through expression of a recombinant nucleic acid sequence introduced into the plant material, for example, by transformation of a plant cell with a vector comprising the recombinant nucleic acid sequence and regeneration of a plant material or whole plant from the transformed plant cell.

B. RNAi-Mediated Target Gene Suppression

In embodiments, the invention provides iRNA molecules (e.g., dsRNA, siRNA, miRNA, and hpRNA) that may be designed to target essential native nucleotide sequences (e.g., essential genes) in the transcriptome of a coleopteran pest (e.g., WCR or NCR), for example by designing an iRNA molecule that comprises at least one strand comprising a nucleotide sequence that is specifically complementary to the target sequence. The sequence of an iRNA molecule so designed may be identical to the target sequence, or may incorporate mismatches that do not prevent specific hybridization between the iRNA molecule and its target sequence.

iRNA molecules of the invention may be used in methods for gene suppression in a coleopteran pest, thereby reducing the level or incidence of damage caused by the pest on a plant (for example, a protected transformed plant comprising an iRNA molecule). As used herein the term "gene suppression" refers to any of the well-known methods for reducing the levels of protein produced as a result of gene transcription to mRNA and subsequent translation of the mRNA, including the reduction of protein expression from a gene or a coding sequence including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand". The passenger strand may be degraded, and the guide strand may be incorporated into RISC. Post-transcriptional inhibition occurs by specific hybridization of the guide strand with a specifically complementary sequence of an mRNA molecule, and subsequent cleavage by the enzyme, Argonaute (catalytic component of the RISC complex).

In embodiments of the invention, any form of iRNA molecule may be used. Those of skill in the art will understand that dsRNA molecules typically are more stable during preparation and during the step of providing the iRNA molecule to a cell than are single-stranded RNA molecules, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a nucleotide sequence, which nucleotide sequence may be expressed in vitro to produce an iRNA molecule that is substantially homologous to a nucleic acid molecule encoded by a nucleotide sequence within the genome of a coleopteran pest. In certain embodiments, the in vitro transcribed iRNA molecule may be a stabilized dsRNA molecule that comprises a stem-loop structure. After a coleopteran pest contacts the in vitro transcribed iRNA molecule, post-transcriptional inhibition of a target gene in the coleopteran pest (for example, an essential gene) may occur.

In some embodiments of the invention, expression of a nucleic acid molecule comprising at least 19 contiguous nucleotides of a nucleotide sequence is used in a method for post-transcriptional inhibition of a target gene in a coleopteran pest, wherein the nucleotide sequence is selected from the group consisting of: SEQ ID NO:1; the complement of SEQ ID NO:1; a fragment of at least 19 contiguous nucleotides of SEQ ID NO:1 (e.g., SEQ ID NOs: 21,22, or 23); the complement of a fragment of at least 19 contiguous nucleotides of SEQ ID NO:1; a native coding sequence of a *Diabrotica* organism (e.g., WCR) comprising SEQ ID NO:1; the complement of a native coding sequence of a *Diabrotica* organism comprising SEQ ID NO:1; a native non-coding sequence of a *Diabrotica* organism that is transcribed into a native RNA molecule comprising SEQ ID NO:1; the complement of a native non-coding sequence of a *Diabrotica* organism that is transcribed into a native RNA molecule comprising SEQ ID NO:1; a fragment of at least 19 contiguous nucleotides of a native coding sequence of a *Diabrotica* organism (e.g., WCR) comprising SEQ ID NO:1; the complement of a fragment of at least 19 contiguous nucleotides of a native coding sequence of a *Diabrotica* organism comprising SEQ ID NO:1; a fragment of at least 19 contiguous nucleotides of a native non-coding sequence of a *Diabrotica* organism that is transcribed into a native RNA molecule comprising SEQ ID NO:1; and the complement of a fragment of at least 19 contiguous nucleotides of a native non-coding sequence of a *Diabrotica* organism that is transcribed into a native RNA molecule comprising SEQ ID NO:1. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest.

In some embodiments, expression of at least one nucleic acid molecule comprising at least 19 contiguous nucleotides of a nucleotide sequence may be used in a method for post-transcriptional inhibition of a target gene in a coleopteran pest, wherein the nucleotide sequence is selected from the group consisting of: SEQ ID NO:1; the complement of SEQ ID NO:1; a fragment of at least 19 contiguous nucleotides of SEQ ID NO:1 (e.g., SEQ ID NOs: 21, 22, or 23); the complement of a fragment of at least 19 contiguous nucleotides of SEQ ID NO:1; a native coding sequence of a *Diabrotica* organism (e.g., WCR) comprising SEQ ID NO:1; the complement of a native coding sequence of a *Diabrotica* organism (e.g., WCR) comprising SEQ ID NO:1; a native non-coding sequence of a *Diabrotica* organism that is transcribed into a native RNA molecule comprising SEQ ID NO:1; the complement of a native non-coding sequence of a *Diabrotica* organism that is transcribed into a native RNA molecule comprising SEQ ID NO:1; a fragment of at least 19 contiguous nucleotides of a native coding sequence of a *Diabrotica* organism (e.g., WCR) comprising SEQ ID NO:1; the complement of a fragment of at least 19 contiguous nucleotides of a native coding sequence of a *Diabrotica* organism comprising any of SEQ ID NO:1; a fragment of at least 19 contiguous nucleotides of a native non-coding sequence of a *Diabrotica* organism that is transcribed into a native RNA molecule comprising SEQ ID NO:1; and the complement of a fragment of at least 19 contiguous nucleotides of a native non-coding sequence of a *Diabrotica* organism that is transcribed into a native RNA molecule comprising SEQ ID NO: 1. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest. In particular examples, such a nucleic acid molecule may comprise the nucleotide sequence of SEQ ID NO:1.

It is an important feature of some embodiments of the invention that the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present invention is sequence-specific; i.e., nucleotide sequences substantially homologous to the iRNA molecule(s) are targeted for genetic inhibition. In some embodiments, an RNA molecule comprising a nucleotide sequence identical to a portion of a target gene sequence may be used for inhibition. In these and further embodiments, an RNA molecule comprising a nucleotide sequence with one or more insertion, deletion, and/or point mutations relative to a target gene sequence may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length sequence exhibiting a greater homology compensates for a longer, less homologous sequence. The length of the nucleotide sequence of a duplex region of a dsRNA molecule that is identical to a portion of a target gene transcript may be at least about 25, 50, 100, 200, 300, 400, 500, or at least about 1000 bases. In some embodiments, a sequence of greater than 20 to 100 nucleotides may be used. In particular embodiments, a sequence of greater than about 200 to 300 nucleotides may be used. In particular embodiments, a sequence of greater than about 500 to 1000 nucleotides may be used, depending on the size of the target gene.

In certain embodiments, expression of a target gene in a coleopteran pest may be inhibited by at least 10%; at least 33%; at least 50%; or at least 80% within a cell of the coleopteran pest, such that a significant inhibition takes place. Significant inhibition refers to inhibition over a threshold that results in a detectable phenotype (e.g., cessation of growth, cessation of feeding, cessation of development, induced mortality, etc.), or a detectable decrease in RNA and/or gene product corresponding to the target gene being inhibited. Although in certain embodiments of the invention inhibition occurs in substantially all cells of the coleopteran pest, in other embodiments inhibition occurs only in a subset of cells expressing the target gene.

In some embodiments, transcriptional suppression in a cell is mediated by the presence of a dsRNA molecule exhibiting substantial sequence identity to a promoter DNA sequence or the complement thereof, to effect what is referred to as "promoter trans suppression". Gene suppression may be effective against target genes in a coleopteran pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary sequences in the cells of the coleopteran pest. Post-transcriptional gene suppression by antisense or sense oriented RNA to regulate gene expression in plant cells is disclosed in U.S. Pat. Nos. 5,107,065; 5,759,829; 5,283,184; and 5,231,020.

C. Expression of iRNA Molecules Provided to a Coleopteran Pest

Expression of iRNA molecules for RNAi-mediated gene inhibition in a coleopteran pest may be carried out in any one of many in vitro or in vivo formats. The iRNA molecules may then be provided to a coleopteran pest, for example, by contacting the iRNA molecules with the pest, or by causing the pest to ingest or otherwise internalize the iRNA molecules. Some embodiments of the invention include transformed host plants of a coleopteran pest, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by a coleopteran pest during feeding, the pest may ingest iRNA molecules expressed in the transgenic plants or cells. The nucleotide sequences of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a coleopteran pest comprises providing in the tissue of the host of the pest a gene-suppressive amount of at least one dsRNA molecule formed following transcription of a nucleotide sequence as described herein, at least one segment of which is complementary to an mRNA sequence within the cells of the coleopteran pest. A dsRNA molecule, including its modified form such as an siRNA, miRNA, or hpRNA molecule, ingested by a coleopteran pest in accordance with the invention, may be at least from about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or 100% identical to an RNA molecule transcribed from a nucleic acid molecule comprising nucleotide sequence SEQ ID NO:1. Isolated and substantially purified nucleic acid molecules including, but not limited to, non-naturally occurring nucleotide sequences and recombinant DNA constructs for providing dsRNA molecules of the present invention are therefore provided, which suppress or inhibit the expression of an endogenous coding sequence or a target coding sequence in the coleopteran pest when introduced thereto.

Particular embodiments provide a delivery system for the delivery of iRNA molecules for the post-transcriptional inhibition of one or more target gene(s) in a coleopteran plant pest and control of a population of the coleopteran plant pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the invention. Transgenic plant cells and transgenic plants comprising nucleic acid sequences encoding a particular iRNA molecule may be produced by employing recombinant DNA technologies (which basic technologies are well-known in the art) to construct a plant transformation vector comprising a nucleotide sequence encoding an iRNA molecule of the invention (e.g., a stabilized dsRNA molecule); to transform a plant cell or plant; and to generate the transgenic plant cell or the transgenic plant that contains the transcribed iRNA molecule.

To impart coleopteran pest resistance to a transgenic plant, a recombinant DNA molecule may, for example, be transcribed into an iRNA molecule, such as a dsRNA molecule, an siRNA molecule, an miRNA molecule, or an hpRNA molecule. In some embodiments, an RNA molecule transcribed from a recombinant DNA molecule may form a dsRNA molecule within the tissues or fluids of the recombinant plant. Such a dsRNA molecule may be comprised in part of a nucleotide sequence that is identical to a corresponding nucleotide sequence transcribed from a DNA sequence within a coleopteran pest of a type that may infest the host plant. Expression of a target gene within the coleopteran pest may be suppressed by the ingested or otherwise contacted dsRNA molecule, and the suppression of expression of the target gene in the coleopteran pest may result in, for example, cessation of feeding by the coleopteran pest, with an ultimate result being, for example, that the transgenic plant is protected from further damage by the coleopteran pest. The modulatory effects of dsRNA molecules have been shown to be applicable to a variety of genes expressed in pests, including, for example, endogenous genes responsible for cellular metabolism or cellular transformation, including house-keeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a nucleotide sequence for use in producing iRNA molecules may be operably linked to one or more promoter sequences functional in a plant host cell. The promoter may be an endogenous promoter, normally resident in the host genome. The nucleotide sequence of the present invention, under the control of an operably linked promoter sequence, may further be flanked by additional sequences that advantageously affect its transcription and/or the stability of a resulting transcript. Such sequences may be located upstream of the operably linked promoter, downstream of the 3' end of the expression construct, and may occur both upstream of the promoter and downstream of the 3' end of the expression construct.

Some embodiments provide methods for reducing the damage to a host plant (e.g., a corn plant) caused by a coleopteran pest that feeds on the plant, wherein the method comprises providing in the host plant a transformed plant cell expressing at least one nucleic acid molecule of the invention, wherein the nucleic acid molecule(s) functions upon being taken up by the coleopteran pest to inhibit the expression of a target sequence within the coleopteran pest, which inhibition of expression results in mortality, reduced growth, and/or reduced reproduction of the coleopteran pest, thereby reducing the damage to the host plant caused by the coleopteran pest. In some embodiments, the nucleic acid molecule(s) comprise dsRNA molecules. In these and further embodiments, the nucleic acid molecule(s) comprise dsRNA molecules that each comprise more than one nucleotide sequence that is specifically hybridizable to a nucleic acid molecule expressed in a coleopteran pest cell. In some embodiments, the nucleic acid molecule(s) consist of one nucleotide sequence that is specifically hybridizable to a nucleic acid molecule expressed in a coleopteran pest cell.

In some embodiments, a method for increasing the yield of a corn crop is provided, wherein the method comprises introducing into a corn plant at least one nucleic acid molecule of the invention; cultivating the corn plant to allow the expression of an iRNA molecule comprising the nucleic acid sequence, wherein expression of an iRNA molecule comprising the nucleic acid sequence inhibits coleopteran pest growth and/or coleopteran pest damage, thereby reducing or eliminating a loss of yield due to coleopteran pest infestation. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran pest cell. In some embodiments, the nucleic acid molecule(s) consists of one nucleotide sequence that is specifically hybridizable to a nucleic acid molecule expressed in a coleopteran pest cell.

In some embodiments, a method for modulating the expression of a target gene in a coleopteran pest is provided, the method comprising: transforming a plant cell with a vector comprising a nucleic acid sequence encoding at least one nucleic acid molecule of the invention, wherein the nucleotide sequence is operatively-linked to a promoter and a transcription termination sequence; culturing the transformed plant cell under conditions sufficient to allow for development of a plant cell culture including a plurality of transformed plant cells; selecting for transformed plant cells that have integrated the nucleic acid molecule into their genomes; screening the transformed plant cells for expression of an iRNA molecule encoded by the integrated nucleic acid molecule; selecting a transgenic plant cell that expresses the iRNA molecule; and feeding the selected transgenic plant cell to the coleopteran pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran pest cell. In some embodiments, the nucleic acid molecule(s) consists of one nucleotide sequence that is specifically hybridizable to a nucleic acid molecule expressed in a coleopteran pest cell.

iRNA molecules of the invention can be incorporated within the seeds of a plant species (e.g., corn), either as a product of expression from a recombinant gene incorporated into a genome of the plant cells, or as incorporated into a coating or seed treatment that is applied to the seed before planting. A plant cell comprising a recombinant gene is considered to be a transgenic event. Also included in embodiments of the invention are delivery systems for the delivery of iRNA molecules to coleopteran pests. For example, the iRNA molecules of the invention may be directly introduced into the cells of a coleopteran pest. Methods for introduction may include direct mixing of iRNA with plant tissue from a host for the coleopteran pest, as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the coleopteran pests known to infest the plant. iRNA molecules produced by chemical or enzymatic synthesis may also be formulated in a manner consistent with common agricultural practices, and used as spray-on products for controlling plant damage by a coleopteran pest. The formulations may include the appropriate stickers and wetters required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from coleopteran pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following Examples are provided to illustrate certain particular features and/or aspects. These Examples should not be construed to limit the disclosure to the particular features or aspects described.

EXAMPLES

Example 1

Insect Diet Bioassays

Sample Preparation and Bioassays.

A number of dsRNA molecules (including those corresponding to reptin Reg1 (SEQ ID NO:21), reptin Reg2 (SEQ ID NO:22), and reptin Reg3 (SEQ ID NO:23) were synthesized and purified using a MEGASCRIPT® RNAi kit. The purified dsRNA molecules were prepared in TE buffer, and all bioassays contained a control treatment consisting of this buffer, which served as a background check for mortality or growth inhibition of WCR (*Diabrotica virgifera virgifera* LeConte). The concentrations of dsRNA molecules in the bioassay buffer were measured using a NANODROP™ 8000 spectrophotometer (Thermo Scientific, Wilmington, Del.).

Samples were tested for insect activity in bioassays conducted with neonate insect larvae on artificial insect diet. WCR eggs were obtained from Crop Characteristics, Inc. (Farmington, Minn.).

The bioassays were conducted in 128-well plastic trays specifically designed for insect bioassays (C-D International, Pitman, N.J.). Each well contained approximately 1.0 mL of a diet designed for growth of coleopteran insects. A 60 µL aliquot of dsRNA sample was delivered by pipette onto the 1.5 cm$^2$ diet surface of each well (40 µL/cm$^2$). dsRNA sample concentrations were calculated as the amount of dsRNA per square centimeter (ng/cm$^2$) of surface area in the well. The treated trays were held in a fume hood until the liquid on the diet surface evaporated or was absorbed into the diet.

Within a few hours of eclosion, individual larvae were picked up with a moistened camel hair brush and deposited on the treated diet (one or two larvae per well). The infested wells of the 128-well plastic trays were then sealed with adhesive sheets of clear plastic, and vented to allow gas exchange. Bioassay trays were held under controlled environmental conditions (28° C., ~40% Relative Humidity, 16:8 (Light:Dark)) for 9 days, after which time the total number of insects exposed to each sample, the number of dead insects, and the weight of surviving insects were recorded. Average percent mortality and average growth inhibition were calculated for each treatment. Growth inhibition (GI) was calculated as follows:

$$GI = [1 - (TWIT/TNIT)/(TWIBC/TNIBC)]$$

where TWIT is the Total Weight of live Insects in the Treatment;

TNIT is the Total Number of Insects in the Treatment;

TWIBC is the Total Weight of live Insects in the Background Check (Buffer control); and TNIBC is the Total Number of Insects in the Background Check (Buffer control).

Statistical analysis was done using JMP™ software (SAS, Cary, N.C.).

Replicated bioassays demonstrated that ingestion of particular samples resulted in a surprising and unexpected mortality and growth inhibition of corn rootworm larvae.

Example 2

Identification of Candidate Target Genes

Multiple stages of WCR (*Diabrotica virgifera virgifera* LeConte) development were selected for pooled transcriptome analysis to provide candidate target gene sequences for control by RNAi transgenic plant insect resistance technology.

In one exemplification, total RNA was isolated from about 0.9 g whole first-instar WCR larvae; (4 to 5 days post-hatch; held at 16° C.), and purified using the following phenol/TRI REAGENT®-based method (Molecular Research Center, Cincinnati, Ohio; Cat. No. TR 118):

Larvae were homogenized at room temperature in a 15 mL homogenizer with 10 mL of TRI REAGENT® until a homogenous suspension was obtained. Following 5 min. incubation at room temperature, the homogenate was dispensed into 1.5 mL microfuge tubes (1 mL per tube), 200 µL of chloroform was added, and the mixture was vigorously shaken for 15 seconds. After allowing the extraction to sit at room temperature for 10 min, the phases were separated by centrifugation at 12,000×g at 4° C. The upper phase (comprising about 0.6 mL) was carefully transferred into another sterile 1.5 mL tube, and an equal volume (0.6 mL) of room temperature isopropanol was added. After incubation at room temperature for 5 to 10 min, the mixture was centrifuged 8 min at 12,000×g (4° C. or 25° C.).

The supernatant was carefully removed and discarded, and the RNA pellet was washed twice by vortexing with 75% ethanol, with recovery by centrifugation for 5 min at 7,500×g (4° C. or 25° C.) after each wash. The ethanol was carefully removed, the pellet was allowed to air-dry for 3 to 5 min, and then was dissolved in nuclease-free sterile water. RNA concentration was determined by measuring the absorbance (A) at 260 nm and 280 nm. A typical extraction from about 0.9 g of larvae yielded over 1 mg of total RNA, with an $A_{260}/A_{280}$ ratio of 1.9. The RNA thus extracted was stored at −80° C. until further processed.

RNA quality was determined by running an aliquot through a 1% agarose gel. The agarose gel solution was made using autoclaved 10×TAE buffer (Tris-acetate EDTA; 1× concentration is 0.04 M Tris-acetate, 1 mM EDTA (ethylenediamine tetra-acetic acid sodium salt), pH 8.0) diluted with DEPC (diethyl pyrocarbonate)-treated water in an autoclaved container. 1×TAE was used as the running buffer. Before use, the electrophoresis tank and the well-forming comb were cleaned with RNASEAWAY™ (INVITROGEN Inc., Carlsbad, Calif.). Two μL of RNA sample were mixed with 8 μL of TE buffer (10 mM Tris HCl pH 7.0; 1 mM EDTA) and 10 μL of RNA sample buffer (Novagen® Catalog No 70606; EMD4 Bioscience, Gibbstown, N.J.). The sample was heated at 70° C. for 3 min, cooled to room temperature, and 5 μL (containing 1 μg to 2 μg RNA) were loaded per well. Commercially available RNA molecular weight markers were simultaneously run in separate wells for molecular size comparison. The gel was run at 60 v for 2 hr.

A normalized cDNA library was prepared from the larval total RNA by a commercial service provider (Eurofins MWG Operon, Huntsville, Ala.), using random priming.

The normalized larval cDNA library was sequenced at ½ plate scale by GS FLX 454 Titanium™ series chemistry at Eurofins MWG Operon, which resulted in over 600,000 reads with an average read length of 348 bp. 350,000 reads were assembled into over 50,000 contigs. Both the unassembled reads and the contigs were converted into BLASTable databases using the publicly available program, FORMATDB (available from NCBI).

Total RNA and normalized cDNA libraries were similarly prepared from materials harvested at other WCR developmental stages. A pooled transcriptome library for target gene screening was constructed by combining cDNA library members representing the various developmental stages.

Candidate genes for RNAi targeting were selected using information regarding lethal RNAi effects of particular genes in other insects such as *Drosophila* and *Tribolium*. These genes were hypothesized to be essential for survival and growth in coleopteran insects. Selected target gene homologs were identified in the transcriptome sequence database as described below. Full-length or partial sequences of the target genes were amplified by PCR to prepare templates for double-stranded RNA (dsRNA) production.

TBLASTN searches using candidate protein coding sequences were run against BLASTable databases containing the unassembled *Diabrotica* sequence reads or the assembled contigs. Significant hits to a *Diabrotica* sequence (defined as better than $e^{-20}$ for contigs homologies and better than $e^{-10}$ for unassembled sequence reads homologies) were confirmed using BLASTX against the NCBI non-redundant database. The results of this BLASTX search confirmed that the *Diabrotica* homolog candidate gene sequences identified in the TBLASTN search indeed comprised *Diabrotica* genes, or were the best hit to the non-Diabrotica candidate gene sequence present in the *Diabrotica* sequences. In most cases, *Tribolium* candidate genes which were annotated as encoding a protein gave an unambiguous sequence homology to a sequence or sequences in the *Diabrotica* transcriptome sequences. In a few cases, it was clear that some of the *Diabrotica* contigs or unassembled sequence reads selected by homology to a non-Diabrotica candidate gene overlapped, and that the assembly of the contigs had failed to join these overlaps. In those cases, Sequencher™ v4.9 (Gene Codes Corporation, Ann Arbor, Mich.) was used to assemble the sequences into longer contigs.

A candidate target gene encoding reptin (SEQ ID NO:1) was identified as a gene that may lead to coleopteran pest mortality, inhibition of growth, inhibition of development, or inhibition of reproduction in WCR. The sequence of SEQ ID NO:1 is believed to be novel.

The *Drosophila* reptin gene encodes a protein with DNA helicase activity, and is associated with negative gene regulation and chromatin silencing (Diop et al., (2008) EMBO J. 9: 260-266; Qi et al., (2006) Genetics 174: 241-251). Loss-of-function mutations in a *Drosophila* reptin gene cause lethality (Bauer et al., (2000) EMBO J. 19: 6121-6130; Bellosta et al., (2005) Proc. Natl. Acad. Sci. U.S.A. 102: 11799-11804).

Full-length or partial clones of sequences of *Diabrotica* candidate gene homologs, herein referred to as reptin, were used to generate PCR amplicons for dsRNA synthesis.

SEQ ID NO:1 presents a 1639 bp DNA sequence encoding reptin.

SEQ ID NO:21 shows an exemplary amplified fragment of reptin Reg1 used for in vitro dsRNA synthesis, which was amplified using primer Pair 1 (T7 at 5' end) and primer Pair 2 (T7 at 3' end) (Table 1). T7 promoter sequences at the 5' and 3' ends are not shown.

SEQ ID NO:22 shows an exemplary amplified fragment of reptin Reg2 used for in vitro dsRNA synthesis, which was amplified using primer Pair 3 (T7 at 5' end) and primer Pair 4 (T7 at 3' end) (Table 1). T7 promoter sequences at the 5' and 3' ends are not shown.

SEQ ID NO:23 shows an exemplary amplified fragment of reptin Reg3 used for in vitro dsRNA synthesis, which was amplified using primer Pair 5 (T7 at 5' end) and primer Pair 6 (T7 at 3' end) (Table 1). T7 promoter sequences at the 5' and 3' ends are not shown.

Example 3

Amplification of Target Genes

Primers were designed to amplify portions of coding regions of each target gene by PCR. See Table 1. Where appropriate, a T7 phage promoter sequence (TTAATACGACTCACTATAGGGAGA; SEQ ID NO:3) was incorporated into the 5' ends of the amplified sense or antisense strands. See Table 1. Total RNA was extracted from WCR, and first-strand cDNA was used as template for PCR reactions using opposing primers positioned to amplify all or part of the native target gene sequence. dsRNA was also amplified from the coding region for a yellow fluorescent protein (YFP) (SEQ ID NO:4).

TABLE 1

Primers and Primer Pairs used to amplify portions of reptin coding region and YFP negative control gene.

| | Gene | Primer ID | SEQ ID NO: | Sequence |
|---|---|---|---|---|
| Pair 1 | Reptin Reg1 | Reptin-F1T7 | 5 | TTAATACGACTCACTA TAGGGAGACTAATAAA TAATGGCTGCAGCTGC TG |
| | Reptin Reg1 | Reptin-R1 | 6 | TTTTCTAATAGCTTGA GTTATAGC |
| Pair 2 | Reptin Reg1 | Reptin-F1 | 7 | CTAATAAATAATGGCT GCAGCTGCTG |
| | Reptin Reg1 | Reptin-R1T7 | 8 | TTAATACGACTCACTA TAGGGAGATTTTCTAA TAGCTTGAGTTATAGC |

TABLE 1-continued

Primers and Primer Pairs used to amplify portions of reptin coding region and YFP negative control gene.

| Gene | Primer ID | SEQ ID NO: | Sequence |
|---|---|---|---|
| Pair 3 | Reptin Reg2 | Reptin-F2T7 | 9 | TTAATACGACTCACTA TAGGGAGAAGCAAACT AGATTTGTACAGTGTC C |
| | Reptin Reg2 | Reptin-R2 | 10 | CTCTAATTTTGGTGAT CCCTCTGTTA |
| Pair 4 | Reptin Reg2 | Reptin-F2 | 11 | AGCAAACTAGATTTGT ACAGTGTCC |
| | Reptin Reg2 | Reptin-R2T7 | 12 | TTAATACGACTCACTA TAGGGAGACTCTAATT TTGGTGATCCCTCTGT TA |
| Pair 5 | Reptin Reg3 | Reptin-F3T7 | 13 | TTAATACGACTCACTA TAGGGAGACACCAAAA TTAGAGGAACAACATA CAA |
| | Reptin Reg3 | Reptin-R3 | 14 | TTACATGGTTTCAATT TCCATATCATC |
| Pair 6 | Reptin Reg3 | Reptin-F3 | 15 | CACCAAAATTAGAGGA ACAACATACAA |
| | Reptin Reg3 | Reptin-R3T7 | 16 | TTAATACGACTCACTA TAGGGAGATTACATGG TTTCAATTTCCATATC ATC |
| Pair 7 | YFP | YFP-F_T7 | 17 | TTAATACGACTCACTA TAGGGAGACACCATGG GCTCCAGCGGCGCCC |
| | YFP | YFP-R | 18 | AGATCTTGAAGGCGCT CTTCAGG |
| Pair 8 | YFP | YFP-F | 19 | CACCATGGGCTCCAGC GGCGCCC |
| | YFP | YFP-R_T7 | 20 | TTAATACGACTCACTA TAGGGAGAAGATCTTG AAGGCGCTCTTCAGG |

Example 4

RNAi Constructs

Template Preparation by PCR and dsRNA Synthesis

The strategy used to provide specific templates for dsRNA production is shown in FIG. 1. Template DNAs intended for use in dsRNA synthesis were prepared by PCR using the primer pairs in Table 1 and (as PCR template) first-strand cDNA prepared from total RNA isolated from WCR first-instar larvae. For each selected target gene region, two separate PCR amplifications were performed. The first PCR amplification introduced a T7 promoter sequence at the 5' end of the amplified sense strands. The second reaction incorporated the T7 promoter sequence at the 5' ends of the antisense strands. The two PCR amplified fragments for each region of the target genes were then mixed in approximately equal amounts, and the mixture was used as transcription template for dsRNA production. See FIG. 1. The sequences of the dsRNA templates amplified with the particular primer pairs were: reptin Reg1 (SEQ ID NO:21), reptin Reg2 (SEQ ID NO:22), and reptin Reg3 (SEQ ID NO:23). Double-stranded RNA was synthesized and purified using an AMBION® MEGAscript® RNAi kit following the manufacturer's instructions (INVITROGEN). The concentrations of dsRNAs were measured using a NanoDrop™ 8000 spectrophotometer (Thermo Scientific, Wilmington, Del.).

Construction of Plant Transformation Vectors

A hairpin RNA expression vector, pDAB109820, for Agrobacterium-mediated transformation, was assembled using standard GATEWAY® (INVITROGEN) cloning methods. The target gene construct for hairpin formation comprising segments of a nucleotide sequence encoding reptin (SEQ ID NO:1) was assembled using a combination of chemically synthesized fragments (DNA2.0, Menlo Park, Calif.) and standard molecular cloning methods. Intramolecular hairpin formation by RNA primary transcripts was facilitated by arranging (within a single transcription unit) two copies of the target gene fragments in opposite orientation to one another, the two fragments being separated by an ST-LS1 intron sequence (SEQ ID NO:55) (Vancanneyt et al. (1990) Mol. Gen. Genet. 220:245-50). Entry vectors containing expression cassettes of a hairpin construct of SEQ ID NO:1 were assembled using GATEWAY® cloning methods and standard cloning methods. Production of the primary mRNA transcript was driven by a copy of the maize ubiquitin 1 promoter (U.S. Pat. No. 5,510,474). Thus, the primary mRNA transcript contained the two reptin gene fragment sequences as large inverted repeats of one another, separated by the intron sequence. A fragment comprising a 3' untranslated region from a maize peroxidase 5 gene (ZmPer5 3'UTR v2; U.S. Pat. No. 6,699,984) was used to terminate transcription of the hairpin-RNA-expressing gene.

A hairpin RNA expression transformation vector for Agrobacterium-mediated maize embryo transformation (pDAB109820) was constructed using a typical binary destination vector (pDAB101847) and an entry vector described above through use of a standard GATEWAY® recombination reaction. In addition to the target gene construct for hairpin formation, the binary destination vector comprised a herbicide resistance gene (aryloxyalknoate dioxygenase; aad-1 v3) (U.S. Pat. No. 7,838,733(B2), and Wright et al. (2010) Proc. Natl. Acad. Sci. U.S.A. 107:20240-5) under the transcriptional regulation of a sugarcane bacilliform badnavirus (ScBV) promoter (Schenk et al. (1999) Plant Molec. Biol. 39:1221-1230) and a 3' untranslated region from a maize lipase gene (ZmLip 3'UTR; U.S. Pat. No. 7,179,902).

The same set of entry vectors used for GATEWAY® cloning into destination vectors to construct a hairpin RNA expression vector for Agrobacterium-mediated transformation was used to construct (pDAB109833), which is a hairpin RNA expression vector for WHISKERS™-mediated maize cell transformation. pDAB 109833 was constructed using a starting destination vector and a constructed entry vector by means of a standard GATEWAY® recombination reaction. The destination vector comprises two marker genes: a yellow fluorescent protein gene (YFP; Shagin et al. (2004) Mol. Biol. Evol. 21:841-850) and an herbicide tolerance gene (phosphinothricin acetyl transferase (PAT); Wehrmann et al. (1996) Nat. Biotechnol. 14:1274-1278). The transcription of the YFP and PAT coding regions was driven by separate copies of the ScBV promoter. A fragment comprising a 3' untranslated region from a maize lipase gene (ZmLip 3'UTR; U.S. Pat. No. 7,179,902) was used to terminate transcription of the YFP gene, while transcription termination of the PAT gene was controlled by a fragment containing a potato pinII gene 3'UTR (StPinII 3'UTR; essentially GenBank™ Accession No. X04118.1).

SEQ ID NO:24 presents a reptin hairpin-RNA-forming sequence.

A binary transformation vector used to provide transgenic, negative control maize tissues and plants was also constructed by similar methods. Plasmid pDAB101556 binary vector harbors a YFP coding region under expression control of a maize-derived ubiquitin1 promoter and Per5 3' UTR, and an AAD1 coding region under the expression control of a maize-derived ubiquitin1 promoter and Lip 3' UTR (all as described herein).

Example 5

Screening of Candidate Target Genes

Synthetic dsRNA designed to inhibit target gene sequences identified in EXAMPLE 2 caused mortality and growth inhibition when administered to WCR in diet-based assays. Reptin Reg1, reptin Reg2, and reptin Reg3 were observed to exhibit increased efficacy in this assay over other dsRNAs screened.

Replicated bioassays demonstrated that ingestion of dsRNA preparations derived from reptin Reg1, reptin Reg2, and reptin Reg3 each resulted in mortality and/or growth inhibition of western corn rootworm larvae. Table 2 shows the results of diet-based feeding bioassays of WCR larvae following 9-day exposure to these dsRNAs, as well as the results obtained with a negative control sample of dsRNA prepared from a yellow fluorescent protein coding region (SEQ ID NO:4).

TABLE 2

Results of independent dsRNA diet feeding assays obtained with western corn rootworm larvae after 9 days of feeding. ANOVA analysis found significant differences in Mean % Mortality and Mean Growth Inhibition. Means were separated using the Tukey-Kramer test.

| Gene Name | Dose (ng/cm$^2$) | No. Rep. Rows | Mean % Mortality (±SEM)* | Mean Growth Inhibition (±SEM) |
| --- | --- | --- | --- | --- |
| Reptin Reg1 | 1000 | 4 | 61.86 ± 7.75 (A)** | 0.78 ± 0.05 (A) |
| TE buffer | 0 | 12 | 8.04 ± 2.32 (B) | 0.00 ± 0.0 (B) |
| WATER | 0 | 12 | 9.25 ± 2.19 (B) | 0.00 ± 0.0 (B) |
| YFP | 1000 | 12 | 8.15 ± 2.15 (B) | −0.12 ± 0.16 (B) |
| Reptin Reg2 | 1000 | 6 | 44.49 ± 9.46 (A) | 0.70 ± 0.08 (A) |
| TE buffer | 0 | 12 | 8.04 ± 2.32 (B) | 0.00 ± 0.0 (B) |
| WATER | 0 | 12 | 9.25 ± 2.19 (B) | 0.00 ± 0.0 (B) |
| YFP | 1000 | 12 | 8.15 ± 2.15 (B) | −0.12 ± 0.16 (B) |
| Reptin Reg3 | 1000 | 4 | 39.51 ± 19.41 (A) | 0.54 ± 0.16A |
| TE buffer | 0 | 12 | 8.04 ± 2.32 (B) | 0.00 ± 0.0 (B) |
| WATER | 0 | 12 | 9.25 ± 2.19 (B) | 0.00 ± 0.0 (B) |
| YFP | 1000 | 12 | 8.15 ± 2.15 (B) | −0.12 ± 0.16 (B) |

*SEM = Standard Error of the Mean
**Letters in parentheses designate statistical levels. Levels not connected by the same letter are significantly different (P < 0.05). Reg1 and Reg2 data were obtained in independent experiments and analyzed separately.
**TE = Tris HCl (10 mM) plus EDTA (1 mM) buffer, pH8.

In separate experiments, bioassays were conducted as above with increasing concentrations of reptin Reg1, reptin Reg2, and reptin Reg3 dsRNA preparations incorporated into the diet. Results are tabulated in Table 3. The LC$_{50}$ of dRNA for reptin Reg1 was calculated to be 174 ng/cm$^2$, and the GI$_{50}$ was calculated to be 1.54 ng/cm$^2$.

TABLE 3

Results of independent dsRNA diet feeding assays obtained with western corn rootworm larvae after 9 days of feeding. ANOVA analysis found significant differences in Mean % Mortality and Mean Growth Inhibition. Means were separated using the Tukey-Kramer test.

| Gene Name Reptin Reg1 | Dose (ng/cm$^2$) | No. Rep. Rows | Mean % Mortality | Mean Growth Inhibition |
| --- | --- | --- | --- | --- |
| | 1 | 2 | 17.65 | 0.46 |
| | 4 | 2 | 30.88 | 0.57 |
| | 16 | 2 | 46.85 | 0.67 |
| | 64 | 2 | 35.85 | 0.63 |
| | 250 | 2 | 50.00 | 0.80 |
| | 1000 | 4 | 61.86 | 0.78 |

| Reptin Reg1 | LC$_{50}$ (ng/cm$^2$) | LC$_{50}$ Range | GI$_{50}$ (ng/cm$^2$) | GI$_{50}$ Range |
| --- | --- | --- | --- | --- |
| | 174 | 59-826 | 1.54 | 0.38-6.19 |

| Reptin Reg2 | Dose (ng/cm$^2$) | No. Rep. Rows | Mean % Mortality | Mean Growth Inhibition |
| --- | --- | --- | --- | --- |
| | 1 | 6 | 16.34 | 0.40 |
| | 4 | 6 | 16.42 | 0.57 |
| | 16 | 6 | 27.54 | 0.68 |
| | 64 | 6 | 33.97 | 0.70 |
| | 250 | 6 | 26.20 | 0.68 |
| | 1000 | 6 | 44.49 | 0.70 |

| Reptin Reg2 | LC$_{50}$ (ng/cm$^2$) | LC$_{50}$ Range | GI$_{50}$ (ng/cm$^2$) | GI$_{50}$ Range |
| --- | --- | --- | --- | --- |
| | 3859 | 861-98570 | 1.96 | 1.02-3.79 |

| Reptin Reg3 | Dose (ng/cm$^2$) | No. Rep. Rows | Mean % Mortality | Mean Growth Inhibition |
| --- | --- | --- | --- | --- |
| | 1 | 1 | 37.50 | 0.89 |
| | 4 | 2 | 11.76 | 0.64 |
| | 6.25 | 2 | 44.80 | 0.77 |
| | 16 | 1 | 50.00 | 0.92 |
| | 25 | 2 | 29.17 | 0.55 |
| | 64 | 2 | 22.92 | 0.72 |
| | 100 | 2 | 24.43 | 0.67 |
| | 250 | 2 | 34.31 | 0.82 |
| | 400 | 2 | 53.57 | 0.83 |
| | 1000 | 4 | 39.51 | 0.54 |

| Reptin Reg3 | LC$_{50}$ (ng/cm$^2$) | LC$_{50}$ Range | GI$_{50}$ (ng/cm$^2$) | GI$_{50}$ Range |
| --- | --- | --- | --- | --- |
| | >2000 | Not Done | Not Done | Not Done |

It has previously been suggested that certain genes of *Diabrotica* spp. may be exploited for RNAi-mediated insect control. See U.S. Patent Publication No. 2007/0124836, which discloses 906 sequences, and U.S. Pat. No. 7,612,194, which discloses 9,112 sequences. However, it was determined herein that many genes suggested to have utility for RNAi-mediated insect control are not efficacious in controlling *Diabrotica*. It was also determined herein that sequences reptin Reg, reptin Reg2, and reptin Reg3 each provide surprising and unexpected control of *Diabrotica*, compared to other genes suggested to have utility for RNAi-mediated insect control.

For example, annexin, beta spectrin 2, and mtRP-L4 were each suggested in U.S. Pat. No. 7,612,194 to be efficacious in RNAi-mediated insect control. SEQ ID NO:25 is a DNA sequence of annexin region 1, and SEQ ID NO:26 is a DNA sequence of annexin region 2. SEQ ID NO:27 is a DNA sequence of beta spectrin 2 region 1, and SEQ ID NO:28 is a DNA sequence of beta spectrin 2 region 2. SEQ ID NO:29 is a DNA sequence of mtRP-L4 region 1, and SEQ ID NO:30 is a DNA sequence of mtRP-L4 region 2. A YFP sequence (SEQ ID NO:4) was also used to produce dsRNA as a negative control.

Each of the aforementioned sequences was used to produce dsRNA by the methods of EXAMPLE 4, and the dsRNAs were each tested by the same diet-based bioassay methods described above. Table 4 lists the sequences of the primers used to produce the annexin, beta spectrin 2, and mtRP-L4 dsRNA molecules. YFP primer sequences are listed in Table 1. Table 5 presents the results of diet-based feeding bioassays of WCR larvae following 9-day exposure to these dsRNA molecules. Replicated bioassays demonstrated that ingestion of these dsRNAs resulted in no mortality or growth inhibition of western corn rootworm larvae above that seen with control samples of TE buffer, YFP, or water.

TABLE 4

Primers and Primer Pairs used to amplify portions of coding regions of genes.

| | Gene (Region) | Primer_ID | SEQ ID NO: | Sequence |
|---|---|---|---|---|
| Pair 9 | annexin (1) | Ann-F1_T7 | 31 | TTAATACGACTCACTA TAGGGAGAGCTCCAAC AGTGGTTCCTTATC |
| | annexin (1) | Ann-R1 | 32 | CTAATAATTCTTTTTT AATGTTCCTGAGG |
| Pair 10 | annexin (1) | Ann-F1 | 33 | GCTCCAACAGTGGTTC CTTATC |
| | annexin (1) | Ann-R1_T7 | 34 | TTAATACGACTCACTA TAGGGAGACTAATAAT TCTTTTTTAATGTTCC TGAGG |
| Pair 11 | annexin (2) | Ann-F2_T7 | 35 | TTAATACGACTCACTA TAGGGAGATTGTTACA AGCTGGAGAACTTCTC |
| | annexin (2) | Ann-R2 | 36 | CTTAACCAACAACGGC TAATAAGG |
| Pair 12 | annexin (2) | Ann-F2 | 37 | TTGTTACAAGCTGGAG AACTTCTC |
| | annexin (2) | Ann-R2T7 | 38 | TTAATACGACTCACTA TAGGGAGACTTAACCA ACAACGGCTAATAAGG |
| Pair 13 | beta-spect2 (1) | Betasp2-F1_T7 | 39 | TTAATACGACTCACTA TAGGGAGAAGATGTTG GCTGCATCTAGAGAA |
| | beta-spect2 (1) | Betasp2-R1 | 40 | GTCCATTCGTCCATCC ACTGCA |
| Pair 14 | beta-spect2 (1) | Betasp2-F1 | 41 | AGATGTTGGCTGCATC TAGAGAA |
| | beta-spect2 (1) | Betasp2-R1_T7 | 42 | TTAATACGACTCACTA TAGGGAGAGTCCATTC GTCCATCCACTGCA |
| Pair 15 | beta-spect2 (2) | Betasp2-F2_T7 | 43 | TTAATACGACTCACTA TAGGGAGAGCAGATGA ACACCAGCGAGAAA |
| | beta-spect2 (2) | Betasp2-R2 | 44 | CTGGGCAGCTTCTTGT TTCCTC |
| Pair 16 | beta-spect2 (2) | Betasp2-F2 | 45 | GCAGATGAACACCAGC GAGAAA |
| | beta-spect2 (2) | Betasp2-R2_T7 | 46 | TTAATACGACTCACTA TAGGGAGACTGGGCAG CTTCTTGTTTCCTC |

TABLE 4-continued

Primers and Primer Pairs used to amplify portions of coding regions of genes.

| | Gene (Region) | Primer_ID | SEQ ID NO: | Sequence |
|---|---|---|---|---|
| Pair 17 | mtRP-L4 (1) | L4-F1_T7 | 47 | TTAATACGACTCACTA TAGGGAGAAGTGAAAT GTTAGCAAATATAACA TCC |
| | mtRP-L4 (1) | L4-R1 | 48 | ACCTCTCACTTCAAAT CTTGACTTTG |
| Pair 18 | mtRP-L4 (1) | L4-F1 | 49 | AGTGAAATGTTAGCAA ATATAACATCC |
| | mtRP-L4 (1) | L4-R1_T7 | 50 | TTAATACGACTCACTA TAGGGAGAACCTCTCA CTTCAAATCTTGACTT TG |
| Pair 19 | mtRP-L4 (2) | L4-F2_T7 | 51 | TTAATACGACTCACTA TAGGGAGACAAAGTCA AGATTTGAAGTGAGAG GT |
| | mtRP-L4 (2) | L4-R2 | 52 | CTACAAATAAAACAAG AAGGACCCC |
| Pair 20 | mtRP-L4 (2) | L4-F2 | 53 | CAAAGTCAAGATTTGA AGTGAGAGGT |
| | mtRP-L4 (2) | L4-R2_T7 | 54 | TTAATACGACTCACTA TAGGGAGACTACAAAT AAAACAAGAAGGACCC C |

TABLE 5

Results of diet feeding assays obtained with western corn rootworm larvae.

| Gene Name | Dose (ng/cm$^2$) | Mean weight per insect (mg) | Mean % Mortality | Mean Growth Inhibition |
|---|---|---|---|---|
| annexin-region 1 | 1000 | 0.545 | 0 | −0.262 |
| annexin-region 2 | 1000 | 0.565 | 0 | −0.301 |
| beta spectrin2 region 1 | 1000 | 0.340 | 12 | −0.014 |
| beta spectrin2 region 2 | 1000 | 0.465 | 18 | −0.367 |
| mtRP-L4 region 1 | 1000 | 0.305 | 4 | −0.168 |
| mtRP-L4 region 2 | 1000 | 0.305 | 7 | −0.180 |
| TE buffer | 0 | 0.430 | 13 | 0.000 |
| Water | 0 | 0.535 | 12 | 0.000 |
| YFP | 1000 | 0.480 | 9 | −0.386 |

The results summarized in Table 5 show that double-stranded RNAs corresponding to annexin region 1 and region 2, beta-spectrin2 region 1 and region 2, and mtRP-L4 region 1 and region 2 do not provide significant control of western corn rootworms.

Example 6

Production of Transgenic Maize Tissues Comprising Insecticidal Hairpin dsRNAs

WHISKERS™-Mediated Transformation

Plants that produce one or more insecticidal dsRNA molecules (for example, at least one dsRNA molecule including a dsRNA molecule targeting a gene comprising SEQ ID NO:1) through expression of a chimeric gene stably-integrated into the plant genome were produced.

Preparations of plant transformation DNA molecules prepared essentially as described in EXAMPLE 4 were delivered into maize Hi-II suspension cell cultures via WHISKERS™-mediated transformation (essentially as described in U.S. Pat. Nos. 5,302,523 and 5,464,765; U.S. Patent Publication No. 2008/0182332; and Petolino and Arnold (2009) Methods Mol. Biol. 526:59-67). Transformed tissues were selected by their ability to grow on BASTA™-containing medium and were screened for YFP production, as appropriate.

Plant Cell Transformation and Selection:

Procedures for WHISKERS™-mediated transformation were performed using standard aseptic techniques, and generally followed the methods described by Petolino and Arnold (2009), supra. *Zea mays* Hill embryogenic cell suspensions (Armstrong et al. (1991) Maize Genet. Coop. Newslett. 65:92-93) were subcultured by transferring 30 mL settled suspension cells, plus 70 mL conditioned medium (i.e., the medium in which the cells had been grown), into 200 mL of fresh H9CP (4.33 gm/L MS Basal Salts (PHYTOTECHNOLOGIES LABORATORIES, Cat # M524); 30.0 gm/L Sucrose; 100.0 mg/L Myo-inositol; 200 mg/L Casein Enzymatic Hydrolysate; 2.0 mg/L 2,4-Dichlorophenoxy acetic acid; 2.0 mg/L Naphthaleneacetic acid; 691 mg/L L-Proline; 2.0 mg/L Glycine; 0.5 mg/L Thiamine HCl; 0.5 mg/L Pyridoxine HCl; 0.05 mg/L Nicotinic acid; at pH6.0) media containing 5% coconut water (SIGMA ALDRICH, St. Louis, Mo.; Catalog No. C5915) into a 175 mL NALGENE™ disposable conical bottom centrifuge tube (THERMO FISHER SCIENTIFIC; Catalog No. 3145-0175). The diluted cells were then incubated in a sterile 1 L disposable cell culture flask in the dark at 28° C. on a gyro-rotary shaker with a one inch (2.54 cm) throw radius at 120 rpm, and the cells were subcultured every 3.5 days as described above.

One day following subculture, and 18 to 24 hr prior to the transfection procedure, 50 mL $H_9CP$ medium containing 30 mL settled cells was added to 150 mL fresh GN6 medium (3.99 gm/L Chu N6 Basal Salts with vitamins (PHYTOTECHNOLOGIES LABORATORIES, Cat # C167); 30 gm/L Sucrose; 100 mg/L Myo-Inositol; 2 mg/L 2,4-Dichlorophenoxy acetic acid; at pH6.0) in a sterile 1 L flask, and the culture was incubated on a gyro-rotary shaker as described above.

Following 18 to 24 hr of incubation in GN6 media, the entire cell suspension was transferred to a sterile 175 mL disposable conical bottom centrifuge tube, and the cells were allowed to settle for 1-3 min, yielding a cell volume of about 40 mL. The spent medium was carefully decanted, and residual liquid was removed by pipette to produce a moist cell mass. Cells were resuspended in about 180 mL of high osmotic medium (GN6-SM; GN6 medium supplemented with 45 gm/L sorbitol and 45 gm/L mannitol) in the centrifuge tube, and the culture was placed on a table top rocker shaker at room temperature (23° C. to 25° C.) for about 30 minutes, but not more than 45 minutes. Following the 30 minute osmotic treatment, the cells were allowed to settle in the centrifuge tube for 3 to 5 minutes. Then, the liquid was carefully removed down to the 50 mL mark of the centrifuge tube via pipette, taking caution not to disturb the cells.

For delivery of plasmid DNA to the maize suspension culture cells, 5 mL of a 5% w/w suspension of BIOGRADE™ SC-9 silicon carbide whiskers (ADVANCED COMPOSITE MATERIALS, Greer, S.C.; lot 981011-101) was prepared by adding an appropriate amount of GN6-SM medium to sterilized (autoclaved), dry whiskers. An appropriate amount of DNA of pDAB109833 (EXAMPLE 4) was added to the centrifuge tube (typically 80 μg/50 mL suspension of 40 mL cells), the cap was sealed tightly, and the tube was gently swirled to mix the contents. The centrifuge tube was fastened securely in a commercial paint mixer (RED DEVIL™ Model 5400; Minneapolis, Minn.) modified to securely hold the tube, and shaken for 10-20 seconds. After dilution to reduce the osmolarity of the medium with about 150 mL fresh medium (GN6-SM:GN6; 2:1 v/v) to a final volume of about 200 mL, the cells were incubated on a table top rocker shaker at room temperature for about 1 hour.

The transfected cells were then transferred by pipette in aliquots of about 8.3 mL onto sterile 70 mm WHATMAN™ #4 filter paper (THERMO FISHER SCIENTIFIC), taking care to evenly distribute the cells on the filter paper. The filters were placed on GN6 agar medium in 100×20 mm plastic plates, and then incubated in plastic boxes in the dark at 28° C. for 7 days.

One week after transformation, the filter papers holding the cells were transferred to fresh plates of GN6-1H (GN6 medium supplemented with 2.5 gm/L GELZAN™) solid agar medium containing 1.0 mg/L BIALAPHOS in 100×20 mm plates, and incubated in the dark at 28° C. BIALAPHOS was provided as HERBIACE® (20% ai) (MEIJI SEIKA KAISHA LTD.; Tokyo, JP).

One week later, the cells were embedded in soft agar by scraping the cell contents of each filter paper into a 50 mL sterile disposable centrifuge tube containing 15 mL of GN6 soft agarose medium (GN6 medium with 7.0 gm/L SEAPLAQUE™ Agarose; LONZA, Rockland, Me.) at 37° C. to 40° C., shaking the capped tube vigorously, and then pouring the contents of the tube evenly onto four 100×25 mm plastic plates containing GN61H solid agar medium. Each plate was agitated to coat the surface with an even layer of the cell suspension, and upon solidification the plates were incubated at 28° C. in the dark.

Following six to 10 weeks of incubation, well-growing emerging colonies were transferred to fresh plates containing GN61H agar medium. These candidate transformed colonies were allowed to grow for 2-4 weeks on the selection medium to establish stable events having a mass of about 50 to 200 mg tissue, which were then subjected to molecular analysis.

Samples of 0.1 mL packed callus cells from candidate events were sampled and placed in 1.2 mL COSTAR™ polypropylene cluster tubes (CORNING, INC.; Corning N.Y.) and frozen at −80° C.

Transgenic Plant Regeneration:

Selected stably-transformed events were regenerated into plants for in-planta insect bioassays.

Following the selection process, callus cultures were transferred to Pre-Regeneration 28 Medium (4.33 gm/L MS Basal Medium with Vitamins; 30.0 gm/L Sucrose; 5 mg/L 6-Benzylaminopurine; 25 μg/L 2,4-Dichlorphenoxyactetic acid; 2.5 gm/L GELZAN™; and 1.0 mg/L BIALAPHOS). Transferred callus cultures were incubated for 7 days at 28° C. under continuous white fluorescent light (approximately 50 $\mu Em^{-2} s^{-1}$).

For regeneration, the cultures were transferred to Regeneration Medium 36 (4.33 gm/L MS Basal Medium with Vitamins; 30 gm/L Sucrose; 2.5 gm/L GELZAN™; and 1.0 mg/L BIALAPHOS), and plantlets were allowed to generate and grow at 28° C. under continuous white fluorescent light for up to 3 weeks. When plantlets reached a suitable growth stage, they were excised with a forceps and scalpel, transferred to a 20×100 mm test tube containing agar, and placed in the light for 2 days.

Transgenic plants were assigned unique identifiers and transferred to a controlled environment chamber (~28° C. daytime temperature; 24° C. nighttime temperature; with a 16:8 supplemental lighting photoperiod). The plants were transplanted from tubes to 3.5 inch (8.89 cm) pots, returned to the controlled environment chamber for 1 to 2 weeks to acclimate, and were then moved to the greenhouse where they were transplanted from the small pots to ROOTRAINERS™ (style TINUS™ 350-4; SPENCER-LEMAIRE INDUSTRIES; Acheson, Alberta, Canada), (one plant per event per ROOTRAINER™) for insect feeding bioassays. Approximately four days after transplanting to ROOTRAINERS™, the $T_0$ plants were ready for the insect feeding bioassay. For each event selected for testing, one to three plants were bioassayed by the methods described in EXAMPLE 8.

Plants of the $T_1$ generation were obtained by pollinating the silks of $T_0$ transgenic plants with pollen collected from plants of non-transgenic elite inbred line 5XH751, and planting the resultant seeds.

*Agrobacterium*-Mediated Transformation

Alternatively, transgenic maize cells, tissues, and plants that produce one or more insecticidal dsRNA molecules (for example, at least one dsRNA molecule including a dsRNA molecule targeting a gene comprising SEQ ID NO:1) through expression of a chimeric gene stably integrated into the plant genome were produced following *Agrobacterium*-mediated transformation. Maize transformation methods employing superbinary or binary transformation vectors are known in the art, as described, for example, in International PCT Publication No. WO2010/120452. Transformed tissues were selected by their ability to grow on haloxyfop-containing medium and were screened for dsRNA production, as appropriate. Portions of such transformed tissue cultures may be presented to neonate corn rootworm larvae for bioassay, essentially as described in EXAMPLE 5.

Ear Sterilization and Embryo Isolation.

Maize immature embryos were obtained from plants of *Zea mays* inbred line B104 grown in the greenhouse and self- or sib-pollinated to produce ears. The ears were harvested approximately 9 to 12 days post-pollination. On the experimental day, de-husked ears were surface-sterilized by immersion in a 20% solution of sodium hypochlorite (6.15%) and shaken for 20 to 30 min, followed by three rinses in sterile water. After sterilization, immature zygotic embryos (1.5 to 2.4 mm) were aseptically dissected from each ear and randomly distributed into microcentrifuge tubes containing liquid Inoculation Medium. Inoculation Medium contained: 2.2 gm/L MS salts (Frame et al., 2011 supra); 1×ISU Modified MS Vitamins (Frame et al. (2011, *Genetic Transformation Using Maize Immature Zygotic Embryos*. IN Plant Embryo Culture Methods and Protocols: Methods in Molecular Biology. T. A. Thorpe and E. C. Yeung, (Eds), SPRINGER SCIENCE AND BUSINESS MEDIA, LLC. pp 327-341)); 68.4 gm/L sucrose; 36 gm/L glucose; 115 mg/L L-proline; 100 mg/L myo-inositol; and 200 µM acetosyringone (prepared in DMSO); at pH 5.4. For a given set of experiments, embryos from pooled ears were used for each transformation.

*Agrobacterium* Culture Initiation.

Glycerol stocks of *Agrobacterium* strain DAt13192 containing a binary transformation vector pDAB109820 as described above (4) were streaked on AB minimal medium plates (Watson, et al., (1975) J. Bacteriol. 123:255-264) containing appropriate antibiotics and were grown at 20° C. for 3 to 4 days. A single colony was picked and streaked onto YEP plates (gm/L: yeast extract, 10; Peptone, 10; NaCl 5) containing the same antibiotics and the plates were incubated at 20° C. for 1-2 days.

*Agrobacterium* Culture and Co-Cultivation.

*Agrobacterium* colonies were taken from a YEP plate, suspended in 10 mL of Inoculation Medium in a 50 mL disposable tube, and the cell density was adjusted to an $OD_{550}$ of 0.2 to 0.4 (Optical Density measured at 550 nm, an indirect measure of cell concentration) using a spectrophotometer. The *Agrobacterium* cultures were incubated on a rotary shaker at 125 rpm (room temperature) while embryo dissection was performed. Immature zygotic embryos (previously isolated from the sterilized maize kernels and placed in 1 mL of Inoculation Medium) were washed once in the same medium. Two mL of the *Agrobacterium* suspension were added to each tube of embryos and the tubes were placed on a shaker platform for 10 to 15 minutes. The embryos were transferred onto Co-cultivation Medium, oriented with the scutellum facing up, and incubated at 25° C., under 24-hour light at 50 $\mu Em^{-2} sec^{-1}$ light intensity for 3 days. Co-cultivation Medium contained 4.33 gm/L MS salts; 1×ISU Modified MS Vitamins; 30 gm/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L $AgNO_3$; 100 µM acetosyringone in DMSO; and 3 gm/L GELZAN™ (SIGMA-ALDRICH); at pH 5.8.

Callus Selection and Regeneration of Putative Events.

Following the co-cultivation period, embryos were transferred to Resting Medium and incubated at 25° C. under 24-hour light at 50 $\mu Em^{-2} sec^{-1}$ light intensity, for 3 days. Resting Medium contained 4.33 gm/L MS salts; 1×ISU Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L $AgNO_3$; 0.5 gm/L MES (2-(N-morpholino)ethanesulfonic acid monohydrate; PHYTOTECHNOLOGIES LABR.; Lenexa, Kans.); 250 mg/L Carbenicillin; and 2.3 gm/L GELZAN™; at pH 5.8. Embryos were transferred onto Selection Medium 1 (which consisted of the Resting Medium (above) with 100 nM R-Haloxyfop acid (0.0362 mg/L)), and incubated in either dark and/or under 24-hour light at 50 $\mu Em^{-2} sec^{-1}$ light intensity for 7 to 14 days at 28° C. Proliferating embryogenic calli were transferred onto Selection Medium 2 (which consisted of Resting Medium (above), with 500 nM R-Haloxyfop acid (0.1810 mg/L)), and were incubated in 24-hour light at 50 $\mu Em^{-2} sec^{-1}$ light intensity for 14 to 21 days at 28° C. This selection step allowed transgenic callus to further proliferate and differentiate.

Proliferating, embryogenic calli were transferred onto PreRegeneration Medium and cultured under 24-hour light at 50 $\mu Em^{-2} sec^{-1}$ light intensity for 7 days at 28° C. PreRegeneration Medium contained 4.33 gm/L MS salts; 1×ISU Modified MS Vitamins; 45 gm/L sucrose; 350 mg/L L-proline; 100 mg/L myo-inositol; 50 mg/L Casein Enzymatic Hydrolysate; 1.0 mg/L $AgNO_3$; 0.25 gm/L MES; 0.5 mg/L naphthaleneacetic acid in NaOH; 2.5 mg/L abscisic acid in ethanol; 1 mg/L 6-benzylaminopurine; 250 mg/L Carbenicillin; 2.5 gm/L GELZAN™; and 500 nM R-Haloxyfop acid; at pH 5.8. Embryogenic calli with shoot-like buds were transferred onto Regeneration Medium and cultured under 24-hour light at 50 $\mu Em^{-2} sec^{-1}$ light intensity for 7 days. Regeneration Medium I contained 4.33 gm/L MS salts; 1×ISU Modified MS Vitamins; 60 gm/L sucrose; 100 mg/L myo-inositol; 125 mg/L Carbenicillin; 3.0 gm/L GELZAN™; and 500 nM R-Haloxyfop acid; at pH 5.8. Small shoots with primary roots were transferred to Shoot/Root medium in PHYTATRAYS (PHYTOTECHNOLOGIES LABR.; Lenexa, Kans.) and were incubated under 16:8 hr. light:dark at 140 to 190 $\mu Em^{-2}$ $sec^{-1}$ light intensity for 7 days at 27° C. Shoot/Root Medium contained 4.33 gm/L MS salts; 1×ISU Modified MS Vitamins; 30 gm/L sucrose; 100 mg/L myo-inositol; 3.5 gm/L GELZAN™; at pH 5.8. Putative transgenic plantlets were analyzed for transgene copy number by quantitative real-time PCR assays using primers designed to detect relative copy numbers of the ZmPer5 3' UTR (used to terminate transcription of the reptin hairpin-RNA expression gene), and were transferred to soil.

Transfer and Establishment of $T_0$ Plants in the Greenhouse for Bioassay and Seed Production.

Transformed plant tissues selected by their ability to grow on medium containing 500 nM R-Haloxyfop acid were transplanted into METRO-MIX 360 soilless growing medium (SUN GRO HORTICULTURE) and hardened-off in a growth room. Plants were then transplanted into SUNSHINE CUSTOM BLEND 160 soil mixture and grown to flowering in the greenhouse.

Plants to be used for insect bioassays were transplanted from small pots to TINUS™ 350-4 ROOTRAINERS® (Spencer-Lemaire Industries, Acheson, Alberta, Canada) (one plant per event per ROOTRAINER®). Approximately four days after transplanting to ROOTRAINERS®, plants were infested for bioassay.

Example 7

Molecular Analyses of Transgenic Maize Tissues

Hairpin RNA Transcript Expression Level: Per 5 3'UTR qPCR.

Callus cell events or transgenic plants were analyzed by real time quantitative PCR (qPCR) of the Per 5 3'UTR sequence to determine the relative expression level of the full length hairpin transcript, as compared to the transcript level of an internal maize gene (SEQ ID NO:75; GENBANK Accession No. BT069734) that encodes a TIP41-like protein (i.e. a maize homolog of GENBANK Accession No. AT4G34270; tBLASTX score of 74% identity). RNA was isolated using the RNAEASY™ 96 kit (QIAGEN, Valencia, Calif.). After the first wash (RW1), the columns were treated with QIAGEN RNase-free DNase in buffer "RDD" (according to the kit's suggested alternate protocol). First strand cDNA was prepared using a HIGH CAPACITY cDNA SYNTHESIS KIT (INVITROGEN) in a 10 µL reaction volume with 5 µL denatured RNA, substantially according to the manufacturer's recommended protocol. The protocol was modified slightly to include the addition of 10 µL 100 µM T20VN oligonucleotide (IDT) into the 1 mL tube of random primer stock mix, in order to prepare a working stock of combined random primers and oligo dT.

Following cDNA synthesis, samples were diluted 1:3 with nuclease-free water, and stored at −20° C. until assayed. Real-time PCR was performed on a LIGHTCYCLER™ 480 (ROCHE DIAGNOSTICS, Indianapolis, Ind.) in 10 µL reaction volume. All assays included negative controls of no-template (mix only). For the standard curves, a blank (water in source well) was also included in the source plate to check for sample cross-contamination. Reactions were run with the ROCHE UNIVERSAL PROBE™ at 0.5 µM and the primers for the target and reference genes at 10 µM. The primer sequences are set forth in Table 6. PCR reactions conditions were as follows: (1) Target activation at 95° C. for 10 min; (2) 43 cycles of (denature at 95° C. for 10 sec and extension at 60° C.); (3) acquire at 72° C. for 1 sec; and (4) cool at 40° C. for 10 sec.

TABLE 6

Primer sequences used for molecular analyses of transcript levels in transgenic maize.

| Target | Primer | SEQ ID NO. | Primer Sequence |
|---|---|---|---|
| TIP41* | MZTIPU67F | 56 | AGCCAAGCCAGTGGT ACTTC |
| TIP41 | MZTIPU67R | 57 | TCGCAGACAAAGTAG CAAATGT |
| Per5 3'UTR | P5U76S (F) | 58 | TTGTGATGTTGGTGG CGTAT |
| Per5 3'UTR | P5U76A (R) | 59 | TGTTAAATAAAACCC CAAAGATCG |

*TIP41-like protein.

Data were analyzed using LIGHTCYCLER™ Software v1.5 by relative quantification using a second derivative max algorithm for calculation of Cq values according to the supplier's recommendations. For expression analyses, expression values were calculated using the ΔCt method (i.e., 2-(Cq TARGET-Cq REF)), which relies on the comparison of differences of Cq values between two targets, with the base value of 2 being selected under the assumption that, for optimized PCR reactions, the product doubles every cycle.

Hairpin Transcript Size and Integrity: Northern Blot Assay.

Additional molecular characterization of some of the transgenic plants was obtained by the use of northern blot (RNA blot) analysis to determine the molecular size of the reptin hairpin RNA in transgenic plants expressing a reptin hairpin dsRNA. A full-length nascent transcript is expected to have a molecular size of about 1000 bp, depending on the amount of polyadenylation of the RNA.

All materials and equipment were treated with RNAZAP (AMBION/INVITROGEN) before use. Tissue samples (100 mg to 500 mg) were collected in 2 mL SAFELOCK EPPENDORF tubes, disrupted with a KLECKO™ tissue pulverizer (Garcia Manufacturing, Visalia, Calif.) with three tungsten beads in 1 mL of TRIZOL (INVITROGEN) for 5 min, then incubated at room temperature (RT) for 10 min. Optionally, the samples were centrifuged for 10 min at 4° C. at 11,000 rpm and the supernatant was transferred into a fresh 2 mL SAFELOCK EPPENDORF tube. After 200 µL of chloroform were added to the homogenate, the tube was mixed by inversion for 2 to 5 min, incubated at RT for 10 minutes, and centrifuged at 12,000×g for 15 min at 4° C. The top phase was transferred into a sterile 1.5 mL EPPENDORF tube, 600 µL of 100% isopropanol were added, followed by incubation at RT for 10 min to 2 hr, then centrifuged at 12,000×g for 10 min at 4° to 25° C. The supernatant was discarded and the RNA pellet was washed twice with 1 mL of 70% ethanol, with centrifugation at 7,500×g for 10 min at 4° to 25° C. between washes. The ethanol was discarded and the pellet was briefly air dried for 3 to 5 min before resuspending in 50 µL of nuclease-free water.

Total RNA was quantified using the NANODROP8000® (Thermo-Fisher) and samples were normalized to 5 µg/10 µL. 10 µL of glyoxal (AMBION/INVITROGEN) were then added to each sample. Five to 14 ng of DIG RNA standard marker mix (Roche Applied Science, Indianapolis, Ind.) were dispensed and added to an equal volume of glyoxal. Samples and marker RNAs were denatured at 50° C. for 45 min and stored on ice until loading on a 1.25% SEAKEM GOLD agarose (Lonza, Allendale, N.J.) gel in NORTHERNMAX 10× glyoxal running buffer (AMBION/INVITROGEN) RNAs were separated by electrophoresis at 65 volts/30 mA for 2 hr and 15 min.

Following electrophoresis, the gel was rinsed in 2×SSC for 5 min and imaged on a GEL DOC station (BioRad, Hercules, Calif.), then the RNA was passively transferred to a nylon membrane (MILLIPORE) overnight at RT, using 10×SSC as the transfer buffer (20×SSC consists of 3 M sodium chloride and 300 mM trisodium citrate, pH 7.0). Following the transfer, the membrane was rinsed in 2×SSC for 5 minutes, the RNA was UV-crosslinked to the membrane (Agilent/Stratagene), and the membrane was allowed to dry at RT for up to 2 days.

The membrane was prehybridized in ULTRAHYB buffer (AMBION/INVITROGEN) for 1 to 2 hr. The probe consisted of a PCR amplified product containing the sequence of interest, (for example, the antisense sequence portion of SEQ ID NO:24) labeled with digoxygenin by means of a Roche Applied Science DIG procedure. Hybridization in recommended buffer was overnight at a temperature of 60° C. in hybridization tubes. Following hybridization, the blot was subjected to DIG washes, wrapped, exposed to film for 1 to 30 minutes, then the film was developed, all by methods recommended by the supplier of the DIG kit.

Hairpin Transcript Size and Integrity: ST-LS1 Intron Hydrolysis Probe Assay.

A hydrolysis probe assay (as described below; "Hydrolysis Probe Assays") targeting the ST-LS1 intron spacer sequence in the hairpin RNA (SEQ ID NO:24 and SEQ ID NO:55) was developed to measure integrity of the dsRNA transcript. The oligonucleotides used are listed in Table 7.

Hydrolysis Probe Assays

Transgene Copy Number.

Tissues of $T_0$ transgenic maize plants were screened via a hydrolysis probe assay to confirm the presence of the PAT coding region (WHISKERS-transformed Hi II events) or the aad-1 coding region (*Agrobacterium*-transformed B104 events). The data were used to estimate the transgene copy number, compared to results obtained in similar assays to detect a two-copy native chromosomal gene (invertase, SEQ ID NO:76). The oligonucleotides used are listed in Table 7.

Tissue samples were macerated with a KLECO™ tissue pulverizer and stainless steel beads (Hoover Precision Products, Cumming, Ga.), in QIAGEN RLT buffer. Genomic DNA was isolated in high-throughput format using a BIOSPRINT 96™ Plant kit (QIAGEN) according to the manufacturer's suggested protocol and quantified by QUANT-IT PICO GREEN DNA ASSAY KIT™ (MOLECULAR PROBES/INVITROGEN). DNA concentration was adjusted to around 2 ng/μL for the hydrolysis probe assay using a BIOROBOT3000™ automated liquid handler (QIAGEN). Transgene copy number determination was performed by real-time PCR using the LIGHTCYCLER®480 system (Roche Applied Science, Indianapolis, Ind.). Assays were designed for aad-1, PAT, and an internal reference gene (invertase; GENBANK Accession No: U16123.1; SEQ ID NO:76) using the LIGHTCYCLER® PROBE DESIGN SOFTWARE v2.0. For amplification, LIGHTCYCLER® 480 Probes Master mix was prepared at 1× final concentration in a 10 μL volume multiplex reaction containing 0.4 μM of each primer for aad-1 or PAT, and 0.2 μM of each probe (Table 7). A two-step amplification reaction was performed with an extension at 60° C. for 40 seconds with fluorescence acquisition. All samples were run and the averaged Cycle threshold (Ct) values were used for analysis of each sample. Analysis of real time PCR data was performed using LIGHTCYCLER® SOFTWARE release 1.5 using the relative quant module, and was based on the ΔΔCt method. Controls included a sample of genomic DNA from a single copy calibrator line and known two copy checks that were included in each run.

Vector Backbone Hydrolysis Probe Assays.

Transgenic tissues were analyzed by means of a hydrolysis probe assay designed to detect the SpnR gene (SEQ ID NO:77; encodes bacterial spectinomycin resistance) harbored on the transforming plasmid to determine if any vector backbone DNA had been integrated into the maize genome. The oligonucleotides used are listed in Table 7.

TABLE 7

Primer and probe sequences used for hydrolysis probe assays.

| Target | Oligonucleotide Name | SEQ ID NO: | Sequence |
|---|---|---|---|
| aad-1 | GAAD1F (forward primer) | 60 | TGTTCGGTTCCCT CTACCAA |
| aad-1 | GAAD1R (reverse primer) | 62 | CAACATCCATCAC CTTGACTGA |
| aad-1 | GAAD1P (probe) | 61 | CACAGAACCGTCG CTTCAGCAACA |
| Invertase | IVF-Taq (forward primer) | 64 | TGGCGGACGACGA CTTGT |
| Invertase | IVR-Taq (reverse primer) | 65 | AAAGTTTGGAGGC TGCCGT |
| Invertase | IV-P (probe) | 63 | CGAGCAGACCGCC GTGTACTTCTACC |
| PAT | PAT-F (forward primer) | 66 | GGAACGCTTACGA TTGGACAGTT |
| PAT | PAT-R (reverse primer) | 67 | AGATCCTAGGCCC AACCTTTGA |
| PAT | PAT-P (probe) | 68 | ATGTGACACGTAA ACAGTACTCTC |
| ST-LS1 Intron | RNAi DNA F (forward primer) | 69 | GTATGTTTCTGCT TCTACCTTTGAT |
| ST-LS1 Intron | RNAi DNA R (reverse primer) | 70 | CCATGTTTTGGTC ATATATTAGAAAA GTT |
| ST-LS1 Intron | RNAi DNA FAM (probe) | 71 | AGTAATATAGTAT TTCAAGTATTTTT TTCAAAAT |
| SpnR | SPC1A (reverse primer) | 72 | CTTAGCTGGATAA CGCCAC |
| SpnR | SPC1S (forward primer) | 73 | GACCGTAAGGCTT GATGAA |
| SpnR | TQSPEC (probe) | 74 | CGAGATTCTCCGC GCTGTAGA |

Example 8

Plant Bioassay of Transgenic Maize

In Vitro Insect Bioassays

Bioactivity of the dsRNA of the subject invention produced in plant cells is demonstrated by bioassay methods. See, e.g., Baum et al. (2007) Nat. Biotechnol. 25(11):1322-6. One is able to demonstrate efficacy, for example, by feeding various plant tissues or tissue pieces derived from a plant producing an insecticidal dsRNA to target insects in a controlled feeding environment. Alternatively, extracts are prepared from various plant tissues derived from a plant producing the insecticidal dsRNA and the extracted nucleic acids are dispensed on top of artificial diets for bioassays as previously described herein. The results of such feeding assays are compared to similarly conducted bioassays that employ appropriate control tissues from host plants that do not produce an insecticidal dsRNA, or to other control samples.

Insect Bioassays in the Greenhouse

Western corn rootworm (WCR, *Diabrotica virgifera virgifera* LeConte) eggs were received in soil from CROP CHARACTERISTICS (Farmington, Minn.). WCR eggs were incubated at 28° C. for 10-11 days. Eggs were washed from the soil, placed into a 0.15% agar solution, and the concentration was adjusted to approximately 75 to 100 eggs per 0.25 mL aliquot. A hatch plate was set up in a Petri dish with an aliquot of egg suspension to monitor hatch rates.

The soil around the maize plants growing in ROOTRAINERS® was infested with 125 to 200 WCR eggs. The insects were allowed to feed for 2 weeks, after which time a "Root Rating" was given to each plant. A Node-Injury Scale was utilized for grading essentially according to Oleson et al. (2005) J. Econ. Entomol. 98(1):1-8. Plants which passed this bioassay were transplanted to 5-gallon pots for seed production. Transplants were treated with insecticide to prevent further rootworm damage and insect release in the greenhouses.

Bioassay of WHISKERS™-Mediated Hi II Transgenic Maize Events.

One to three plants for each of the 5 events selected for testing (109833[3]-001, 109833[3]-006, 109833[3]-008, 109833[2]-017, and 109833[3]-020) by the methods described above were bioassayed for rootworm control. The expression of a transgene producing a reptin hairpin dsRNA results in a reduction in WCR root pruning, as was evident in those plants that exhibit high expression levels of the dsRNA transcript (as measured by relative PCR scoring of the Per5 3'UTR). The results of western corn rootworm bioassays on selected events containing an RNAi hairpin comprising SEQ ID NO:24 are shown in Table 8. The results show that those transgenic RNAi plants that have a relative expression level 16-fold or higher than the internal TIP41-like reference gene, and were Northern blot Positive, demonstrated reduced WCR damage. All of the non-transgenic control plants tested suffered severe rootworm damage. In some instances, the Northern blot assays were unable to detect a reptin hairpin dsRNA transcript, although the more sensitive PCR scoring of the Per5 3'UTR indicated there was expression of the hairpin reptin-encoding transgene. Nevertheless, the "Northern-Negative" plants demonstrated rootworm control in the bioassays. Although the biological response was variable within the $T_0$ transgenic maize plants, appreciable reduction of WCR pruning as compared to the non-transgenic control plants was observed.

TABLE 8

Results of western corn rootworm bioassays of greenhouse-grown Hi II $T_0$ transgenic plants from WHISKERS ™-transformed events expressing a reptin hairpin dsRNA.

| Event | Root Damage Rating | Rel. Expr. Level Per5 3'UTR* | Northern Result |
|---|---|---|---|
| 109833[3]-001.010 | 0.25 | 7.4 | Negative |
| 109833[3]-006.001 | 0.5 | 35.8 | Positive |
| 109833[3]-006.005 | 0.5 | 58.1 | Positive |
| 109833[3]-006.007 | 0.5 | 45.9 | Positive |
| 109833[3]-008.003 | 0.25 | 1.9 | Negative |
| 109833[2]-017.002 | 0.5 | 50.2 | Negative |
| 109833[3]-017.006 | 0.5 | 16.3 | Positive |
| 109833[3]-017.007 | 0.25 | 41.4 | Positive |
| 109833[3]-020.008 | 0.5 | 0 | NT** |
| 109833[3]-020.011 | 0.75 | 0.1 | NT |
| Negative Controls | | | |
| Hi-II | 0.97 | NT | NA*** |
| B104 | 0.96 | NT | NA*** |

*Relative to maize TIP41-like transcript level.
**NT = Not Tested
***NA = Not Applicable Seeds from $T_0$ plants from events 109833-006.001, 109833-006.005, 109833-17.002, 109833-17.006, 109833-17.007, 109833-20.008 and 109833-20.011 were harvested after the plants were fertilized with pollen from nontransgenic plants of maize line 5XH751. Several of these T1 seeds from each plant were planted in the greenhouse and bioassayed as described above for rootworm control. The results are presented in Table 9. The data clearly demonstrate that, in all but two cases, the $T_1$ progeny of $T_0$ transgenics that suffered substantially less rootworm feeding damage than nontransgenic controls, also were substantially resistant to damage by corn rootworms. It is therefore a significant and novel finding that a double-stranded reptin-targeted RNA, produced by expression of a chromosomally integrated transgene encoding a hairpin reptin-targeted dsRNA, can provide useful control of corn rootworms.

TABLE 9

Results of western corn rootworm root feeding bioassays and molecular analyses performed on extracted leaf samples of greenhouse-grown $T_1$ transgenic plants from WHISKERS ™-transformed events expressing a reptin hairpin dsRNA.

| Event or Line Name | Root Damage Rating | PAT Copy No. | Intron Copy No. | qPCR SpecR |
|---|---|---|---|---|
| 109833[3]-006.001R.013 | 0.05 | 2.6 | 0.6 | 4.3 |
| 109833[3]-006.001R.016 | 0.05 | 2.4 | 0.7 | 3.9 |
| 109833[3]-006.001R.019 | 0.05 | 2.4 | 0.6 | 4.1 |
| 109833[3]-006.001R.026 | 0.01 | 1.6 | 0.4 | 3.2 |
| 109833[3]-006.001R.029 | 0.01 | 3.4 | 0.7 | 5.1 |
| 109833[3]-006.005R.001 | 0.05 | 2.9 | 0.7 | 4.4 |
| 109833[3]-006.005R.005 | 0.01 | 2.5 | 0.6 | 4.1 |
| 109833[3]-006.005R.008 | 0.05 | 2.6 | 0.6 | 3.8 |
| 109833[3]-017.002R.001 | 0.01 | 1.6 | 1.3 | 4.4 |
| 109833[3]-017.006R.002 | 0.05 | 1.6 | 1.2 | 4.0 |
| 109833[3]-017.007R.002 | 0.01 | 1.3 | 1.1 | 4.1 |
| 109833[3]-017.007R.003 | 0.01 | 1.9 | 1.2 | 4.6 |
| 109833[3]-017.007R.005 | 0.05 | 1.5 | 1.3 | 4.3 |
| 109833[3]-017.007R.007 | 0.01 | 1.4 | 1.3 | 3.9 |
| 109833[3]-017.007R.014 | 0.05 | 1.3 | 1.2 | 3.9 |
| 109833[3]-020.008R.001 | 0.75 | 1.4 | 0.0 | 0.0 |

TABLE 9-continued

Results of western corn rootworm root feeding bioassays and molecular analyses performed on extracted leaf samples of greenhouse-grown $T_1$ transgenic plants from WHISKERS ™-transformed events expressing a reptin hairpin dsRNA.

| | Root Damage Rating | PAT Copy No. | Intron Copy No. | qPCR SpecR |
|---|---|---|---|---|
| 109833[3]-020.011X.021 | 0.25 | 1.4 | 0.0 | 0.0 |
| 109833[3]-020.011X.025 | 1 | ND* | ND | ND |
| 109833[3]-020.011X.027 | 0.75 | 1.3 | 0.0 | 0.0 |
| 109833[3]-020.011X.029 | 0.75 | ND | ND | ND |
| 109833[3]-020.011X.030 | 1 | ND | ND | ND |
| Negative Controls | | | | |
| 101556[93]*** | 1 | NA** | NA | ND |
| 101556[93] | 1 | NA | NA | ND |
| 101556[93] | 1 | NA | NA | ND |
| 101556[93] | 1 | NA | NA | ND |
| Hi II | 0.94 | NA | NA | NA |
| B104 | 1 | NA | NA | NA |
| B104 | 1 | NA | NA | NA |
| B104 | 1 | NA | NA | NA |
| B104 | 1 | NA | NA | NA |

*ND = Not Done
**NA = Not Applicable
*****101556[93] plants are B104 transgenic events that were obtained following *Agrobacterium*-mediated transformation with a pDAB101556 binary vector by the methods disclosed herein.

Some events that expressed a reptin hairpin dsRNA were selected for additional molecular analyses as summarized in Table 9. In most instances, plants that had a low Root Damage Rating were Northern blot Positive and had high transgene dsRNA expression (compared to the TIP41-like reference transcript levels).

Table 10 presents the results of Analysis of Variance (ANOVA) of the Root Damage Ratings when averaged over the plants derived from three events shown in Table 9. T1 plants derived from events 109833[3]-006 and 109833[3]-017 had statistically significantly lower root feeding damage than other plants in the comparison group.

TABLE 10

ANOVA data of Root Damage Ratings of selected greenhouse-grown Hi II $T_1$ transgenic plants from WHISKERS ™-transformed events expressing a reptin hairpin dsRNA.

| Event Name | Mean Root Damage Rating | Significance Group* |
|---|---|---|
| 109833[3]-020. | 0.75 | B |
| 109833[3]-006 | 0.035 | C |
| 109833[3]-017 | 0.030 | C |
| 101556[93]** | 1.0 | A |
| Negative Controls | | |
| Hi II [F1] | 0.94 | AB |
| B104 | 1.0 | A |

*Letters designate statistical levels as separated by the Tukey-Kramer test on the means. Levels not connected by the same letter are significantly different ($P < 0.05$).
**101556[93] plants are B104 transgenic events that were obtained following *Agrobacterium*-mediated transformation with a pDAB101556 binary vector by the methods disclosed herein.

TABLE 9

Results of additional molecular analyses of selected greenhouse-grown Hi II $T_1$ transgenic plants from WHISKERS ™-transformed events expressing a reptin hairpin dsRNA.

| Event or Line | Root Damage Rating | Tissue | PAT Copy No. | Intron Copy No. | qPCR SpecR | Transcript RTL Per5* | Northern (Full length Trnscrpt) |
|---|---|---|---|---|---|---|---|
| 109833[3]-006.001R.013 | 0.05 | Leaf | 2.6 | 0.6 | 4.3 | 36.8 | Positive |
| | | Root | 2.6 | 0.6 | 1.3 | 71.5 | Positive |
| 109833[3]-006.005R.05 | 0.01 | Leaf | 2.5 | 0.6 | 4.1 | 39.4 | Positive |
| | | Root | 2.5 | 0.6 | 4.1 | 112.2 | Positive |
| 109833[3]-017.002R.01 | 0.01 | Leaf | 1.6 | 1.3 | 4.4 | 39.1 | Positive |
| | | Root | 1.6 | 1.3 | 4.4 | 114.6 | Positive |
| 109833[3]-017.006R.02 | 0.05 | Leaf | 1.6 | 1.2 | 4.0 | 42.8 | Positive |
| | | Root | 1.6 | 1.2 | 4.0 | 84.4 | Positive |
| 109833[3]-017.007R.02 | 0.01 | Leaf | 1.3 | 1.1 | 4.1 | 28.4 | Positive |
| | | Root | 1.3 | 1.1 | 4.1 | 209.4 | Positive |
| 109833[3]-020.008R.01 | 0.75 | Leaf | 1.4 | 0.0 | 0.0 | 0.0 | Negative |
| | | Root | 1.4 | 0.0 | 0.0 | 0.5 | Negative |
| 109833[3]-020.011X.021 | 0.25 | Leaf | 1.4 | 0.0 | 0.0 | 0.0 | Negative |
| | | Root | 1.4 | 0.0 | 0.0 | 0.8 | Negative |
| Negative control | | | | | | | |
| B104 | 1.00 | Leaf | NA** | NA | NA | 0.0 | Negative |
| | | Root | NA | NA | NA | 0.1 | Negative |
| 101556[93]**** | 1.00 | Leaf | NA | NA | ND*** | 0.0 | Negative |
| | | Root | NA | NA | ND*** | 0.1 | Negative |

*Relative to maize TIP41-like transcript level.
**NA = Not Applicable
***ND = Not Done
******101556[93] plants are B104 transgenic events that were obtained following *Agrobacterium*-mediated transformation with a pDAB101556 binary vector by the methods disclosed herein.

Example 9

Bioassay of Agrobacterium-Mediated Transgenic B104 Maize Events

B104 $T_0$ plants from events that comprised a transgene encoding a reptin hairpin dsRNA were bioassayed by the methods described above. The results indicated none of these transgenic RNAi plants demonstrated reduced WCR damage, as compared to the non-transgenic control plants tested (Table 11).

TABLE 11

Results of western corn rootworm bioassays of greenhouse-grown B104 $T_0$ transgenic plants from Agrobacterium-transformed events expressing a reptin hairpin dsRNA.

| Event | AAD1 Copy No. | Intron Copy No. | qPCR SpecR | Transcript RTL Per5 | Root Damage Rating |
|---|---|---|---|---|---|
| 109820[1]-002.001 | 1.4 | 0.0 | 0.0 | 0.0 | ND |
| 109820[1]-003.001 | 2.9 | 0.5 | 0.0 | 4.2 | 1.0 |
| 109820[1]-004.001 | 1.5 | 0.5 | 0.0 | 0.0 | 1.0 |
| 109820[1]-005.001 | 1.6 | 0.5 | 0.0 | 4.7 | 1.0 |
| 109820[1]-006.001 | 1.2 | 0.5 | 0.0 | 10.1 | 1.0 |
| 109820[1]-007.001 | 1.7 | 0.9 | 0.0 | 4.3 | 1.0 |
| 109820[1]-008.001 | 1.2 | 0.6 | 0.0 | 12.0 | 1.0 |
| 109820[1]-009.001 | 1.7 | 0.5 | 0.0 | 5.0 | 1.0 |
| 109820[1]-010.001 | 3.3 | 1.0 | 0.0 | 11.9 | 1.0 |
| 109820[1]-011.001 | 0.8 | 0.5 | 2.1 | 8.1 | 1.0 |
| 109820[1]-012.001 | 1.7 | 0.5 | 1.2 | 3.3 | 1.0 |
| 109820[1]-013.001 | 1.8 | 0.0 | 0.0 | 0.0 | ND |
| 109820[1]-014.001 | 1.5 | 0.6 | 0.0 | 0.1 | 1.0 |
| 109820[1]-015.001 | 0.0 | 0.0 | 0.0 | 0.2 | ND |
| 109820[1]-016.001 | 1.6 | 0.5 | 0.0 | 3.1 | 1.0 |
| 109820[1]-017.001 | 2.3 | 0.5 | 1.8 | 5.8 | 1.0 |
| 109820[1]-018.001 | 1.6 | 1.1 | 2.1 | 6.1 | 1.0 |
| 109820[1]-019.001 | 3.1 | 0.9 | 0.0 | 7.5 | 1.0 |
| 109820[1]-020.001 | 1.2 | 0.5 | 0.0 | 4.2 | 1.0 |
| 109820[1]-021.001 | 1.0 | 0.4 | 1.4 | 7.6 | 1.0 |
| 109820[1]-022.001 | 1.6 | 0.5 | 1.9 | 3.7 | 1.0 |
| 109820[1]-023.001 | 1.4 | 0.5 | 0.0 | 6.1 | 1.0 |
| 109820[1]-024.001 | 1.7 | 0.6 | 2.0 | 4.0 | 1.0 |
| 109820[1]-025.001 | 1.5 | 0.5 | 0.0 | 3.7 | 1.0 |
| 109820[1]-026.001 | 1.5 | 0.6 | 0.0 | 6.0 | 1.0 |
| 109820[1]-027.001 | 1.6 | 0.5 | 0.0 | 4.2 | 1.0 |
| 109820[1]-028.001 | 0.9 | 0.4 | 1.1 | 0.0 | 1.0 |

Example 10

Transgenic Zea mays Comprising Coleopteran Pest Sequences

Ten to 20 transgenic $T_0$ Zea mays plants are generated as described in EXAMPLE 6. A further 10-20 $T_1$ Zea mays independent lines expressing hairpin dsRNA for an RNAi construct comprising SEQ ID NO:1 as set forth, for example, as SEQ ID NO:24, are obtained for corn rootworm challenge. These are confirmed through RT-PCR. Total RNA preparations from selected independent $T_1$ lines are optionally used for RT-PCR with primers designed to bind in the ST-LS1 intron of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic Zea mays plant. Processing of the dsRNA hairpin of the target genes into siRNA is subsequently optionally confirmed in independent transgenic lines using RNA blot hybridizations.

Phenotypic Comparison of Transgenic RNAi Lines and Nontransformed Zea mays.

Target coleopteran pest genes or sequences selected for creating hairpin dsRNA have no similarity to any known plant gene sequence. Hence it is not expected that the production or the activation of (systemic) RNAi by constructs targeting these coleopteran pest genes or sequences will have any deleterious effect on transgenic plants. However, development and morphological characteristics of transgenic lines are compared with wild-type plants, as well as those of transgenic lines transformed with an empty vector having no hairpin-expressing gene. Plant root, shoot, foliage and reproduction characteristics are compared. There is no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 11

Transgenic Zea mays Comprising a Coleopteran Pest Sequence and Additional RNAi Constructs A transgenic Zea mays plant comprising a heterologous coding sequence in its genome that is transcribed into an iRNA molecule that targets an organism other than a coleopteran pest is secondarily transformed via Agrobacterium to produce one or more insecticidal dsRNA molecules (for example, at least one dsRNA molecule including a dsRNA molecule targeting a gene comprising SEQ ID NO:1). Plant transformation plasmid vectors prepared essentially as described in EXAMPLE 4 are delivered via Agrobacterium-mediated transformation into immature maize embryos obtained from a transgenic B104 Zea mays plant comprising a heterologous coding sequence in its genome that is transcribed into an iRNA molecule that targets an organism other than a coleopteran pest.

Example 12

Transgenic Coleopteran Pest-Resistant Plants

In planta delivery of dsRNA, siRNA or miRNA corresponding to target genes and the subsequent uptake by coleopteran pests through feeding results in down-regulation of the target genes through RNA-mediated gene silencing. When the function of a target gene is important at one or more stage(s) of development, the growth, development, and reproduction of the coleopteran pest is affected, and, in the case of at least one of WCR, NCR, SCR, MCR, D. balteata LeConte, D. u. tenella, and D. u. undecimpunctata Mannerheim, leads to failure to successfully infest, feed, develop, and/or reproduce, or leads to death of the coleopteran pest. The choice of target genes and the successful application of RNAi is then used to control coleopteran pests.—Five to ten replicates of 10-20 independent $T_1$ Z. mays transgenic lines for each RNAi construct are challenged with a corn rootworm species as described in EXAMPLE 8. Non-transformed Z. mays seeds are germinated at the same time, and the plants are used as experimental controls for corn rootworm bioassays. The challenge is duplicated for each corn rootworm species. $T_2$ seeds of corn rootworm-resistant, RNAi-producing $T_1$ lines are produced.

There is expected to be significantly more corn rootworm feeding damage on non-transformed control plants than on transgenic Z. mays lines harboring one or more RNAi constructs. iRNA abundance is measured in corn rootworms feeding on roots of non-transformed and RNAi-producing transgenic plants using quantitative real-time RT-PCR. iRNA abundance is further measured in roots of nontransformed and RNAi transgenic plants. There are expected to be significantly more iRNA molecules found in transgenic Z. mays lines harboring one or more RNAi constructs than in control plants. These results indicate that the transgenic lines process siRNAs corresponding to target genes and that these siRNAs are available for uptake by feeding corn rootworms. More importantly, the results indicate that RNAi-mediated inhibition of all the target genes affects growth, development, and viability of the target corn rootworm. Moreover, RNAi molecules having mismatched sequences and having more than 80% sequence identity to target genes affect corn rootworms in a way similar to that seen with RNAi molecules having 100% sequence identity to the target genes The pairing of mismatch sequence with native sequences to form a hairpin dsRNA in the same RNAi construct delivers plant-processed siRNAs capable of affecting the growth, development and viability of feeding coleopteran pests.

What is claimed is:

1. An isolated polynucleotide comprising a heterologous promoter operably linked to a polynucleotide comprising at least one nucleotide sequence(s) selected from the group consisting of:

I) a polynucleotide of SEQ ID NO:1 and the complete complement of SEQ ID NO:1;

II) a polynucleotide of SEQ ID NO:21 and the complete complement of SEQ ID NO:21;

III) a polynucleotide of SEQ ID NO:22 and the complete complement of SEQ ID NO:22; and IV) a polynucleotide of SEQ ID NO:23 and the complete complement of SEQ ID NO:23.

2. An isolated polynucleotide comprising a heterologous promoter operably linked to a polynucleotide comprising SEQ ID NO:24.

3. A plant transformation vector comprising the isolated polynucleotide of claim 1 or 2.

4. The isolated polynucleotide of claim 1 or 2, wherein the polynucleotide is a deoxyribonucleic acid (DNA) molecule.

5. The isolated polynucleotide of claim 1 or 2, further comprising at least one nucleotide sequence encoding a polypeptide from *Bacillus thuringiensis*.

6. The isolated polynucleotide of claim 5, wherein the polypeptide from *B. thuringiensis* is selected from a group comprising Cry3, Cry34, and Cry35.

7. A plant cell transformed with the isolated polynucleotide of claim 1 or 2.

8. A plant transformed with the isolated polynucleotide of claim 1 or 2.

9. A seed of the transformed plant of claim 8, wherein the seed comprises the isolated polynucleotide.

10. The transformed plant of claim 8, wherein the isolated polynucleotide is expressed in the plant as a double-stranded ribonucleic acid molecule.

11. The transformed plant cell of claim 7, wherein the cell is a *Zea mays* cell.

12. The transformed plant of claim 8, wherein the plant is *Zea mays*.

13. A commodity product produced from the transformed plant according to claim 8, wherein the commodity product comprises the isolated polynucleotide.

14. A method for controlling a coleopteran pest population, the method comprising:

providing in a plant transformed with the polynucleotide of claim 1, wherein the polynucleotide is expressed to produce a ribonucleic acid molecule that inhibits the expression of a target sequence within a coleopteran pest in the coleopteran pest population, thereby resulting in decreased growth of the coleopteran pest or coleopteran pest population, relative to a coleopteran pest or pest population infesting a plant of the same species lacking the polynucleotide.

15. The method according to claim 14, wherein the ribonucleic add molecule is a double-stranded ribonucleic add molecule.

16. A method of controlling plant coleopteran pest infestation in a plant, the method comprising providing in the diet of a coleopteran pest the polynucleotide of claim 1 or 2.

17. The method according to claim 16, wherein the diet comprises a plant cell transformed to express the polynucleotide.

* * * * *

SEQUENCE LISTING

```
<160> NUMBER OF SEQ ID NOS: 77

<210> SEQ ID NO 1
<211> LENGTH: 1639
<212> TYPE: DNA
<213> ORGANISM: Diabrotica virgifera

<400> SEQUENCE: 1
cacaatacta attaactata attaaataaa atttttcttt actcgccggg atcgagagta     60
ggtgttttgt caatatttaa aattaacctt aaacgctcca caaacgtttt tcaccgcaaa    120
ttttgtattt tgtggaaaat ctaataaata atggctgcag ctgctgccgc aaaaatagcc    180
gaggtgcgcg aaacaactcg cgttgaaaga attggggccc attctcacat tcgaggtcta    240
ggattagatg atagtcttga agccagacat gtgtctcaag gtatggtcgg ccaagtaaca    300
gctagaagag ctgtaggtat cgttctacaa atggttagag aaggaagaat tgccggcaga    360
gcggtcctct tggctggaca acctggtact ggtaaaacag caatagctac agctttggct    420
catgcacttg gtcaagatac ccctttcaca agtatggcag gttccgaaat atattcttta    480
gaaatgagca agaccgaagc tataactcaa gctattagaa aaagtattgg tgttcgaatt    540
aaagaagaaa gtgaaataat cgaaggtgaa gttgttgaag tgcagattga acgtccagct    600
acaggaattg gtgcaaaagt gggaaaactc atcttgaaaa ccactgatat ggaaactgtt    660
tatgacttgg gaggaaaaat gattgacagt attttgaagg aaaaggtcca gtctggcgat    720
gtgatcacaa ttgacaaagc cacaggtaaa attacgagat taggcagatc ttttgctaga    780
gctagggact acgatgccac tggacagcaa actagatttg tacagtgtcc tgaaggtgaa    840
ttgcagaaac gtaaagaagt agtccacact gtaacattgc acgaaattga tgtcatcaac    900
agcagaacgc atggattttt ggcgttattt tctggagaca ctggcgagat taaaccagag    960
gtgagagagc aaattaatgg caaagtagct gaatggagag aagaaggtaa agcagaaatc   1020
attccaggcg ttctatttat tgatgaagtt cacatgttag atattgaatg tttttcattt   1080
ttgaatagag cattagaaaa cgaaatgtca ccaattgtca ttatggctac taacagaggg   1140
atcaccaaaa ttagaggaac aacatacaag tctccccatg gcattccact agatttatta   1200
gacagaacca taatagtccc cacacaaccc tatgacgaaa aggagttaag agaaatctta   1260
agtatccgat gtgaagaaga agattgtcaa atgtcagata atgcactgac tgtcctcaca   1320
agaaatatgca aggaaacttc tttgcgatat ggtatgcagt tgattatgac atcgagttta   1380
atagcaagaa aacgcaaagc acacgaagtt gatgtcgagg atattaaaag agcttatcaa   1440
ctcttttttg atgaaggaag atctgttcag ttcttgagag agtaccaaca agaatttatg   1500
ttcaatgaaa tagatgataa agatgatatg gaaattgaaa ccatgtaaat gcagcctttt   1560
tgacatatgt gttctatttt tttattttat aagttcgttt ataatattct taataataaa   1620
```
aagattttct attaaaaag                                                1639

<210> SEQ ID NO 2
<211> LENGTH: 465
<212> TYPE: PRT
<213> ORGANISM: Diabrotica virgifera

<400> SEQUENCE: 2

```
Met Ala Ala Ala Ala Ala Lys Ile Ala Glu Val Arg Glu Thr Thr
1               5                   10                  15

Arg Val Glu Arg Ile Gly Ala His Ser His Ile Arg Gly Leu Gly Leu
            20                  25                  30

Asp Asp Ser Leu Glu Ala Arg His Val Ser Gln Gly Met Val Gly Gln
        35                  40                  45

Val Thr Ala Arg Arg Ala Val Gly Ile Val Leu Gln Met Val Arg Glu
    50                  55                  60

Gly Arg Ile Ala Gly Arg Ala Val Leu Leu Ala Gly Gln Pro Gly Thr
65                  70                  75                  80

Gly Lys Thr Ala Ile Ala Thr Ala Leu Ala His Ala Leu Gly Gln Asp
                85                  90                  95

Thr Pro Phe Thr Ser Met Ala Gly Ser Glu Ile Tyr Ser Leu Glu Met
            100                 105                 110

Ser Lys Thr Glu Ala Ile Thr Gln Ala Ile Arg Lys Ser Ile Gly Val
        115                 120                 125

Arg Ile Lys Glu Glu Ser Glu Ile Ile Glu Gly Glu Val Val Glu Val
    130                 135                 140

Gln Ile Glu Arg Pro Ala Thr Gly Ile Gly Ala Lys Val Gly Lys Leu
145                 150                 155                 160

Ile Leu Lys Thr Thr Asp Met Glu Thr Val Tyr Asp Leu Gly Gly Lys
                165                 170                 175

Met Ile Asp Ser Ile Leu Lys Glu Lys Val Gln Ser Gly Asp Val Ile
            180                 185                 190

Thr Ile Asp Lys Ala Thr Gly Lys Ile Thr Arg Leu Gly Arg Ser Phe
        195                 200                 205

Ala Arg Ala Arg Asp Tyr Asp Ala Thr Gly Gln Gln Thr Arg Phe Val
    210                 215                 220

Gln Cys Pro Glu Gly Glu Leu Gln Lys Arg Lys Glu Val Val His Thr
225                 230                 235                 240

Val Thr Leu His Glu Ile Asp Val Ile Asn Ser Arg Thr His Gly Phe
                245                 250                 255

Leu Ala Leu Phe Ser Gly Asp Thr Gly Glu Ile Lys Pro Glu Val Arg
            260                 265                 270

Glu Gln Ile Asn Gly Lys Val Ala Glu Trp Arg Glu Gly Lys Ala
        275                 280                 285

Glu Ile Ile Pro Gly Val Leu Phe Ile Asp Glu Val His Met Leu Asp
    290                 295                 300

Ile Glu Cys Phe Ser Phe Leu Asn Arg Ala Leu Glu Asn Glu Met Ser
305                 310                 315                 320

Pro Ile Val Ile Met Ala Thr Asn Arg Gly Ile Thr Lys Ile Arg Gly
                325                 330                 335

Thr Thr Tyr Lys Ser Pro His Gly Ile Pro Leu Asp Leu Leu Asp Arg
            340                 345                 350

Thr Ile Ile Val Pro Thr Gln Pro Tyr Asp Glu Lys Glu Leu Arg Glu
        355                 360                 365
```

```
Ile Leu Ser Ile Arg Cys Glu Glu Asp Cys Gln Met Ser Asp Asn
    370             375             380
Ala Leu Thr Val Leu Thr Arg Ile Cys Lys Glu Thr Ser Leu Arg Tyr
385                 390                 395                 400
Gly Met Gln Leu Ile Met Thr Ser Ser Leu Ile Ala Arg Lys Arg Lys
            405                 410                 415
Ala His Glu Val Asp Val Glu Asp Ile Lys Arg Ala Tyr Gln Leu Phe
            420                 425                 430
Phe Asp Glu Gly Arg Ser Val Gln Phe Leu Arg Glu Tyr Gln Gln Glu
            435                 440                 445
Phe Met Phe Asn Glu Ile Asp Asp Lys Asp Asp Met Glu Ile Glu Thr
            450                 455                 460
Met
465

<210> SEQ ID NO 3
<211> LENGTH: 24
<212> TYPE: DNA
<213> ORGANISM: Artificial Sequence
<220> FEATURE:
<223> OTHER INFORMATION: synthesized promotor oligonucleotide

<400> SEQUENCE: 3
ttaatacgac tcactatagg gaga                                          24

<210> SEQ ID NO 4
<211> LENGTH: 503
<212> TYPE: DNA
<213> ORGANISM: Artificial Sequence
<220> FEATURE:
<223> OTHER INFORMATION: synthesized partial coding region

<400> SEQUENCE: 4
caccatgggc tccagcggcg ccctgctgtt ccacggcaag atcccctacg tggtggagat     60
ggagggcaat gtggatggcc acaccttcag catccgcggc aagggctacg gcgatgccag    120
cgtgggcaag gtggatgccc agttcatctg caccaccggc gatgtgcccg tgccctggag    180
caccctggtg accaccctga cctacggcgc ccagtgcttc gccaagtacg gccccgagct    240
gaaggatttc tacaagagct gcatgcccga tggctacgtg caggagcgca ccatcacctt    300
cgagggcgat ggcaatttca gacccgcgc cgaggtgacc ttcgagaatg cagcgtgta    360 caatcgcgtg aagctgaatg ccagggcctt caagaaggat ggccacgtgc tgggcaagaa    420
tctggagttc aatttcaccc ccactgcct gtacatctgg ggcgatcagg ccaatcacgg    480
cctgaagagc gccttcaaga tct                                           503

<210> SEQ ID NO 5
<211> LENGTH: 50
<212> TYPE: DNA
<213> ORGANISM: Artificial Sequence
<220> FEATURE:
<223> OTHER INFORMATION: synthesized primer oligonucleotide

<400> SEQUENCE: 5
ttaatacgac tcactatagg gagactaata aataatggct gcagctgctg                50

<210> SEQ ID NO 6
<211> LENGTH: 24
<212> TYPE: DNA
<213> ORGANISM: Artificial Sequence
```

```
<220> FEATURE:
<223> OTHER INFORMATION: synthesized primer oligonucleotide

<400> SEQUENCE: 6
ttttctaata gcttgagtta tagc                                          24

<210> SEQ ID NO 7
<211> LENGTH: 26
<212> TYPE: DNA
<213> ORGANISM: Artificial Sequence
<220> FEATURE:
<223> OTHER INFORMATION: synthesized primer oligonucleotide

<400> SEQUENCE: 7
ctaataaata atggctgcag ctgctg                                        26

<210> SEQ ID NO 8
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 8
ttaatacgac tcactatagg gagatttttct aatagcttga gttatagc               48

<210> SEQ ID NO 9
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 9
ttaatacgac tcactatagg gagaagcaaa ctagatttgt acagtgtcc               49

<210> SEQ ID NO 10
<211> LENGTH: 26
<212> TYPE: DNA
<213> ORGANISM: Artificial Sequence
<220> FEATURE:
<223> OTHER INFORMATION: synthesized primer oligonucleotide

<400> SEQUENCE: 10
ctctaatttt ggtgatccct ctgtta                                        26

<210> SEQ ID NO 11
<211> LENGTH: 25
<212> TYPE: DNA
<213> ORGANISM: Artificial Sequence
<220> FEATURE:
<223> OTHER INFORMATION: synthesized primer oligonucleotide

<400> SEQUENCE: 11
agcaaactag atttgtacag tgtcc                                         25

<210> SEQ ID NO 12
<211> LENGTH: 50
<212> TYPE: DNA
<213> ORGANISM: Artificial Sequence
<220> FEATURE:
<223> OTHER INFORMATION: synthesized primer oligonucleotide

<400> SEQUENCE: 12
ttaatacgac tcactatagg gagactctaa ttttggtgat ccctctgtta              50
```

<210> SEQ ID NO 13
<211> LENGTH: 51
<212> TYPE: DNA
<213> ORGANISM: Artificial Sequence
<220> FEATURE:
<223> OTHER INFORMATION: synthesized primer oligonucleotide

<400> SEQUENCE: 13
ttaatacgac tcactatagg gagacaccaa aattagagga acaacataca a    51

<210> SEQ ID NO 14
<211> LENGTH: 27
<212> TYPE: DNA
<213> ORGANISM: Artificial Sequence
<220> FEATURE:
<223> OTHER INFORMATION: synthesized primer oligonucleotide

<400> SEQUENCE: 14
ttacatggtt tcaatttcca tatcatc    27

<210> SEQ ID NO 15
<211> LENGTH: 27
<212> TYPE: DNA
<213> ORGANISM: Artificial Sequence
<220> FEATURE:
<223> OTHER INFORMATION: synthesized primer oligonucleotide

<400> SEQUENCE: 15
caccaaaatt agaggaacaa catacaa    27

<210> SEQ ID NO 16
<211> LENGTH: 51
<212> TYPE: DNA
<213> ORGANISM: Artificial Sequence
<220> FEATURE:
<223> OTHER INFORMATION: synthesized primer oligonucleotide

<400> SEQUENCE: 16
ttaatacgac tcactatagg gagattacat ggtttcaatt tccatatcat c    51

<210> SEQ ID NO 17
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 17
ttaatacgac tcactatagg gagacaccat gggctccagc ggcgccc    47

<210> SEQ ID NO 18
<211> LENGTH: 23
<212> TYPE: DNA
<213> ORGANISM: Artificial Sequence
<220> FEATURE:
<223> OTHER INFORMATION: synthesized primer oligonucleotide

<400> SEQUENCE: 18
agatcttgaa ggcgctcttc agg    23

<210> SEQ ID NO 19
<211> LENGTH: 23
<212> TYPE: DNA
<213> ORGANISM: Artificial Sequence
<220> FEATURE:
<223> OTHER INFORMATION: synthesized primer oligonucleotide

<400> SEQUENCE: 19
caccatgggc tccagcggcg ccc                                              23

<210> SEQ ID NO 20
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 20
ttaatacgac tcactatagg gagaagatct tgaaggcgct cttcagg                    47

<210> SEQ ID NO 21
<211> LENGTH: 382
<212> TYPE: DNA
<213> ORGANISM: Diabrotica virgifera

<400> SEQUENCE: 21
ctaataaata atggctgcag ctgctgccgc aaaaatagcc gaggtgcgcg aaacaactcg      60
cgttgaaaga attggggccc attctcacat tcgaggtcta ggattagatg atagtcttga    120
agccagacat gtgtctcaag gtatggtcgg ccaagtaaca gctagaagag ctgtaggtat    180
cgttctacaa atggttagag aaggaagaat tgccggcaga gcggtcctct tggctggaca    240
acctggtact ggtaaaacag caatagctac agctttggct catgcacttg gtcaagatac    300
ccctttcaca agtatggcag gttccgaaat atattcttta gaaatgagca agaccgaagc    360
tataactcaa gctattagaa aa                                             382

<210> SEQ ID NO 22
<211> LENGTH: 351
<212> TYPE: DNA
<213> ORGANISM: Diabrotica virgifera

<400> SEQUENCE: 22
agcaaactag atttgtacag tgtcctgaag gtgaattgca gaaacgtaaa gaagtagtcc     60
acactgtaac attgcacgaa attgatgtca tcaacagcag aacgcatgga tttttggcgt   120
tattttctgg agacactggc gagattaaac cagaggtgag agagcaaatt aatggcaaag   180
tagctgaatg gagagaagaa ggtaaagcag aaatcattcc aggcgttcta tttattgatg   240
aagttcacat gttagatatt gaatgttttt cattttgtaa tagagcatta gaaaacgaaa   300
tgtcaccaat tgtcattatg gctactaaca gagggatcac caaaattaga g            351

<210> SEQ ID NO 23
<211> LENGTH: 406
<212> TYPE: DNA
<213> ORGANISM: Diabrotica virgifera

<400> SEQUENCE: 23
caccaaaatt agaggaacaa catacaagtc tccccatggc attccactag atttattaga     60
cagaaccata atagtcccca cacaacccta tgacgaaaag gagttaagag aaatcttaag   120
tatccgatgt gaagaagaag attgtcaaat gtcagataat gcactgactg tcctcacaag   180
aatatgcaag gaaacttctt tgcgatatgg tatgcagttg attatgacat cgagtttaat   240
agcaagaaaa cgcaaagcac acgaagttga tgtcgaggat attaaagag cttatcaact    300 cttttttgat gaaggaagat ctgttcagtt cttgagagag taccaacaag aatttatgtt   360
caatgaaata gatgataaag atgatatgga aattgaaacc atgtaa 406

<210> SEQ ID NO 24
<211> LENGTH: 819
<212> TYPE: DNA
<213> ORGANISM: Artificial Sequence
<220> FEATURE:
<223> OTHER INFORMATION: synthesized artificial sequence

<400> SEQUENCE: 24
aaatagccga ggtgcgcgaa acaactcgcg ttgaaagaat tggggcccat tctcacattc 60
gaggtctagg attagatgat agtcttgaag ccagacatgt gtctcaaggt atggtcggcc 120
aagtaacagc tagaagagct gtaggtatcg ttctacaaat ggttagagaa ggaagaattg 180
ccggcagagc ggtcctcttg gctggacaac ctggtactgg taaaacagca atagctacag 240
ctttggctca tgcacttggt caagataccc ctttcacaag tatggcaggt tccgaaagac 300
tagtaccggt tgggaaaggt atgtttctgc ttctaccttt gatatatata taataattat 360
cactaattag tagtaatata gtatttcaag tattttttc aaaataaaag aatgtagtat 420
atagctattg cttttctgta gtttataagt gtgtatattt taatttataa cttttctaat 480
atatgaccaa acatggtga tgtgcaggtt gatccgcggt tatttcggaa cctgccatac 540
ttgtgaaagg ggtatcttga ccaagtgcat gagccaaagc tgtagctatt gctgttttac 600
cagtaccagg ttgtccagcc aagaggaccg ctctgccggc aattcttcct tctctaacca 660
tttgtagaac gatacctaca gctcttctag ctgttacttg gccgaccata ccttgagaca 720
catgtctggc ttcaagacta tcatctaatc ctagacctcg aatgtgagaa tgggccccaa 780
ttctttcaac gcgagttgtt tcgcgcacct cggctatt 819

<210> SEQ ID NO 25
<211> LENGTH: 218
<212> TYPE: DNA
<213> ORGANISM: Diabrotica virgifera

<400> SEQUENCE: 25
tagctctgat gacagagccc atcgagtttc aagccaaaca gttgcataaa gctatcagcg 60
gattgggaac tgatgaaagt acaatagtag aaattttaag tgtccacaac aacgatgaga 120
ttataagaat ttcccaggcc tatgaaggat tgtaccaacg ctcattggaa tctgatatca 180
aaggagatac ctcaggaaca ttaaaaaaga attattag 218

<210> SEQ ID NO 26
<211> LENGTH: 424
<212> TYPE: DNA
<213> ORGANISM: Diabrotica virgifera

<400> SEQUENCE: 26
ttgttacaag ctggagaact tctctttgct ggaaccgaag agtcagtatt taatgctgta 60
ttctgtcaaa gaaataaacc acaattgaat ttgatattcg acaaatatga agaaattgtt 120
gggcatccca ttgaaaaagc cattgaaaac gagttttcag gaaatgctaa acaagccatg 180
ttacacctta tccagagcgt aagagatcaa gttgcatatt tggtaaccag gctgcatgat 240
tcaatggcag gcgtcggtac tgacgataga actttaatca gaattgttgt ttcgagatct 300
gaaatcgatc tagaggaaat caaacaatgc tatgaagaaa tctacagtaa aaccttggct 360
gataggatag cggatgacac atctggcgac tacaaaaag ccttattagc cgttgttggt 420
taag 424

<210> SEQ ID NO 27
<211> LENGTH: 397
<212> TYPE: DNA
<213> ORGANISM: Diabrotica virgifera

<400> SEQUENCE: 27

```
agatgttggc tgcatctaga gaattacaca agttcttcca tgattgcaag gatgtactga      60
gcagaatagt ggaaaaacag gtatccatgt ctgatgaatt gggaagggac gcaggagctg     120
tcaatgccct tcaacgcaaa caccagaact tcctccaaga cctacaaaca ctccaatcga     180
acgtccaaca aatccaagaa gaatcagcta aacttcaagc tagctatgcc ggtgatagag     240
ctaaagaaat caccaacagg gagcaggaag tggtagcagc ctgggcagcc ttgcagatcg     300
cttgcgatca gagacacgga aaattgagcg atactggtga tctattcaaa ttctttaact     360
tggtacgaac gttgatgcag tggatggacg aatggac                              397
```

<210> SEQ ID NO 28
<211> LENGTH: 490
<212> TYPE: DNA
<213> ORGANISM: Diabrotica virgifera

<400> SEQUENCE: 28

```
gcagatgaac accagcgaga aaccaagaga tgttagtggt gttgaattgt tgatgaacaa      60
ccatcagaca ctcaaggctg agatcgaagc cagagaagac aactttacgg cttgtatttc     120
tttaggaaag gaattgttga gccgtaatca ctatgctagt gctgatatta aggataaatt     180
ggtcgcgttg acgaatcaaa ggaatgctgt actacagagg tgggaagaaa gatgggagaa     240
cttgcaactc atcctcgagg tataccaatt cgccagagat gcggccgtcg ccgaagcatg     300
gttgatcgca caagaacctt acttgatgag ccaagaacta ggacacacca ttgacgacgt     360
tgaaaacttg ataaagaaac acgaagcgtt cgaaaaatcg gcagcggcgc aagaagagag     420
attcagtgct ttggagagac tgacgacgtt cgaattgaga gaaataaaga ggaaacaaga     480
agctgcccag                                                            490
```

<210> SEQ ID NO 29
<211> LENGTH: 330
<212> TYPE: DNA
<213> ORGANISM: Diabrotica virgifera

<400> SEQUENCE: 29

```
agtgaaatgt tagcaaatat aacatccaag tttcgtaatt gtacttgctc agttagaaaa      60
tattctgtag tttcactatc ttcaaccgaa aatagaataa atgtagaacc tcgcgaactt     120
gcctttcctc caaatatca agaacctcga caagtttggt tggagagttt agatacgata     180
gacgacaaaa aattgggtat tcttgagctg catcctgatg ttttttgctac taatccaaga     240
atagatatta tacatcaaaa tgttagatgg caaagtttat atagatatgt aagctatgct     300
catacaaagt caagatttga agtgagaggt                                      330
```

<210> SEQ ID NO 30
<211> LENGTH: 320
<212> TYPE: DNA
<213> ORGANISM: Diabrotica virgifera

<400> SEQUENCE: 30

```
caaagtcaag atttgaagtg agaggtggag gtcgaaaacc gtggccgcaa aagggattgg      60
```

```
gacgtgctcg acatggttca attagaagtc cactttggag aggtggagga gttgttcatg    120
gaccaaaatc tccaacccct catttttaca tgattccatt ctacacccgt ttgctgggtt    180
tgactagcgc actttcagta aaatttgccc aagatgactt gcacgttgtg gatagtctag    240
atctgccaac tgacgaacaa agttatatag aagagctggt caaaagccgc ttttgggggt    300
ccttcttgtt ttatttgtag                                                320
```

<210> SEQ ID NO 31
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 31

```
ttaatacgac tcactatagg gagagctcca acagtggttc cttatc              46
```

<210> SEQ ID NO 32
<211> LENGTH: 29
<212> TYPE: DNA
<213> ORGANISM: Artificial Sequence
<220> FEATURE:
<223> OTHER INFORMATION: synthesized primer oligonucleotide

<400> SEQUENCE: 32

```
ctaataattc tttttaatg ttcctgagg                                  29
```

<210> SEQ ID NO 33
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 33

```
gctccaacag tggttcctta tc                                        22
```

<210> SEQ ID NO 34
<211> LENGTH: 53
<212> TYPE: DNA
<213> ORGANISM: Artificial Sequence
<220> FEATURE:
<223> OTHER INFORMATION: synthesized primer oligonucleotide

<400> SEQUENCE: 34

```
ttaatacgac tcactatagg gagactaata attcttttttt aatgttcctg agg     53
```

<210> SEQ ID NO 35
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 35

```
ttaatacgac tcactatagg gagattgtta caagctggag aacttctc            48
```

<210> SEQ ID NO 36
<211> LENGTH: 24
<212> TYPE: DNA
<213> ORGANISM: Artificial Sequence
<220> FEATURE:
<223> OTHER INFORMATION: synthesized primer oligonucleotide

<400> SEQUENCE: 36
cttaaccaac aacggctaat aagg                                          24

<210> SEQ ID NO 37
<211> LENGTH: 24
<212> TYPE: DNA
<213> ORGANISM: Artificial Sequence
<220> FEATURE:
<223> OTHER INFORMATION: synthesized primer oligonucleotide

<400> SEQUENCE: 37
ttgttacaag ctggagaact tctc                                          24

<210> SEQ ID NO 38
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 38
ttaatacgac tcactatagg gagacttaac caacaacggc taataagg                48

<210> SEQ ID NO 39
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 39
ttaatacgac tcactatagg gagaagatgt tggctgcatc tagagaa                 47

<210> SEQ ID NO 40
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 40
gtccattcgt ccatccactg ca                                            22

<210> SEQ ID NO 41
<211> LENGTH: 23
<212> TYPE: DNA
<213> ORGANISM: Artificial Sequence
<220> FEATURE:
<223> OTHER INFORMATION: synthesized primer oligonucleotide

<400> SEQUENCE: 41
agatgttggc tgcatctaga gaa                                           23

<210> SEQ ID NO 42
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 42
ttaatacgac tcactatagg gagagtccat tcgtccatcc actgca                  46

<210> SEQ ID NO 43
<211> LENGTH: 46
<212> TYPE: DNA

<213> ORGANISM: Artificial Sequence
<220> FEATURE:
<223> OTHER INFORMATION: synthesized primer oligonucleotide

<400> SEQUENCE: 43
ttaatacgac tcactatagg gagagcagat gaacaccagc gagaaa         46

<210> SEQ ID NO 44
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 44
ctgggcagct tcttgtttcc tc                                   22

<210> SEQ ID NO 45
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 45
gcagatgaac accagcgaga aa                                   22

<210> SEQ ID NO 46
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 46
ttaatacgac tcactatagg gagactgggc agcttcttgt ttcctc         46

<210> SEQ ID NO 47
<211> LENGTH: 51
<212> TYPE: DNA
<213> ORGANISM: Artificial Sequence
<220> FEATURE:
<223> OTHER INFORMATION: synthesized primer oligonucleotide

<400> SEQUENCE: 47
ttaatacgac tcactatagg gagaagtgaa atgttagcaa atataacatc c   51

<210> SEQ ID NO 48
<211> LENGTH: 26
<212> TYPE: DNA
<213> ORGANISM: Artificial Sequence
<220> FEATURE:
<223> OTHER INFORMATION: synthesized primer oligonucleotide

<400> SEQUENCE: 48
acctctcact tcaaatcttg actttg                               26

<210> SEQ ID NO 49
<211> LENGTH: 27
<212> TYPE: DNA
<213> ORGANISM: Artificial Sequence
<220> FEATURE:
<223> OTHER INFORMATION: synthesized primer oligonucleotide

<400> SEQUENCE: 49
agtgaaatgt tagcaaatat aacatcc                              27

<210> SEQ ID NO 50
<211> LENGTH: 50
<212> TYPE: DNA
<213> ORGANISM: Artificial Sequence
<220> FEATURE:
<223> OTHER INFORMATION: synthesized primer oligonucleotide

<400> SEQUENCE: 50
ttaatacgac tcactatagg gagaacctct cacttcaaat cttgactttg    50

<210> SEQ ID NO 51
<211> LENGTH: 50
<212> TYPE: DNA
<213> ORGANISM: Artificial Sequence
<220> FEATURE:
<223> OTHER INFORMATION: synthesized primer oligonucleotide

<400> SEQUENCE: 51
ttaatacgac tcactatagg gagacaaagt caagatttga agtgagaggt    50

<210> SEQ ID NO 52
<211> LENGTH: 25
<212> TYPE: DNA
<213> ORGANISM: Artificial Sequence
<220> FEATURE:
<223> OTHER INFORMATION: synthesized primer oligonucleotide

<400> SEQUENCE: 52
ctacaaataa aacaagaagg acccc    25

<210> SEQ ID NO 53
<211> LENGTH: 26
<212> TYPE: DNA
<213> ORGANISM: Artificial Sequence
<220> FEATURE:
<223> OTHER INFORMATION: synthesized primer oligonucleotide

<400> SEQUENCE: 53
caaagtcaag atttgaagtg agaggt    26

<210> SEQ ID NO 54
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 54
ttaatacgac tcactatagg gagactacaa ataaacaag aaggacccc    49

<210> SEQ ID NO 55
<211> LENGTH: 225
<212> TYPE: DNA
<213> ORGANISM: Solanum tuberosum

<400> SEQUENCE: 55
gactagtacc ggttgggaaa ggtatgtttc tgcttctacc tttgatatat atataataat    60
tatcactaat tagtagtaat atagtatttc aagtattttt ttcaaaataa aagaatgtag   120
tatatagcta ttgcttttct gtagtttata agtgtgtata ttttaattta taactttttct  180 aatatatgac caaacatgg tgatgtgcag gttgatccgc ggtta                    225

<210> SEQ ID NO 56

```
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 56
agccaagcca gtggtacttc                                                     20

<210> SEQ ID NO 57
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 57
tcgcagacaa agtagcaaat gt                                                  22

<210> SEQ ID NO 58
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 58
ttgtgatgtt ggtggcgtat                                                     20

<210> SEQ ID NO 59
<211> LENGTH: 24
<212> TYPE: DNA
<213> ORGANISM: Artificial Sequence
<220> FEATURE:
<223> OTHER INFORMATION: synthesized primer oligonucleotide

<400> SEQUENCE: 59
tgttaaataa aaccccaaag atcg                                                24

<210> SEQ ID NO 60
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 60
tgttcggttc cctctaccaa                                                     20

<210> SEQ ID NO 61
<211> LENGTH: 24
<212> TYPE: DNA
<213> ORGANISM: Artificial Sequence
<220> FEATURE:
<223> OTHER INFORMATION: synthesized probe oligonucleotide

<400> SEQUENCE: 61
cacagaaccg tcgcttcagc aaca                                                24

<210> SEQ ID NO 62
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 62
```
caacatccat caccttgact ga                                     22

<210> SEQ ID NO 63
<211> LENGTH: 26
<212> TYPE: DNA
<213> ORGANISM: Artificial Sequence
<220> FEATURE:
<223> OTHER INFORMATION: synthesized probe oligonucleotide

<400> SEQUENCE: 63
cgagcagacc gccgtgtact tctacc                                 26

<210> SEQ ID NO 64
<211> LENGTH: 18
<212> TYPE: DNA
<213> ORGANISM: Artificial Sequence
<220> FEATURE:
<223> OTHER INFORMATION: synthesized primer oligonucleotide

<400> SEQUENCE: 64
tggcggacga cgacttgt                                          18

<210> SEQ ID NO 65
<211> LENGTH: 19
<212> TYPE: DNA
<213> ORGANISM: Artificial Sequence
<220> FEATURE:
<223> OTHER INFORMATION: synthesized primer oligonucleotide

<400> SEQUENCE: 65
aaagtttgga ggctgccgt                                         19

<210> SEQ ID NO 66
<211> LENGTH: 23
<212> TYPE: DNA
<213> ORGANISM: Artificial Sequence
<220> FEATURE:
<223> OTHER INFORMATION: synthesized primer oligonucleotide

<400> SEQUENCE: 66
ggaacgctta cgattggaca gtt                                    23

<210> SEQ ID NO 67
<211> LENGTH: 23
<212> TYPE: DNA
<213> ORGANISM: Artificial Sequence
<220> FEATURE:
<223> OTHER INFORMATION: synthesized primer oligonucleotide

<400> SEQUENCE: 67
ggaacgctta cgattggaca gtt                                    23

<210> SEQ ID NO 68
<211> LENGTH: 24
<212> TYPE: DNA
<213> ORGANISM: Artificial Sequence
<220> FEATURE:
<223> OTHER INFORMATION: synthesized probe oligonucleotide

<400> SEQUENCE: 68
atgtgacacg taaacagtac tctc                                   24

<210> SEQ ID NO 69
<211> LENGTH: 25
<212> TYPE: DNA

```
<213> ORGANISM: Artificial Sequence
<220> FEATURE:
<223> OTHER INFORMATION: synthesized primer oligonucleotide

<400> SEQUENCE: 69
gtatgtttct gcttctacct ttgat                                           25

<210> SEQ ID NO 70
<211> LENGTH: 29
<212> TYPE: DNA
<213> ORGANISM: Artificial Sequence
<220> FEATURE:
<223> OTHER INFORMATION: synthesized primer oligonucleotide

<400> SEQUENCE: 70
ccatgttttg gtcatatatt agaaaagtt                                       29

<210> SEQ ID NO 71
<211> LENGTH: 34
<212> TYPE: DNA
<213> ORGANISM: Artificial Sequence
<220> FEATURE:
<223> OTHER INFORMATION: synthesized probe oligonucleotide

<400> SEQUENCE: 71
agtaatatag tatttcaagt attttttca aaat                                  34

<210> SEQ ID NO 72
<211> LENGTH: 19
<212> TYPE: DNA
<213> ORGANISM: Artificial Sequence
<220> FEATURE:
<223> OTHER INFORMATION: synthesized primer oligonucleotide

<400> SEQUENCE: 72
cttagctgga taacgccac                                                  19

<210> SEQ ID NO 73
<211> LENGTH: 19
<212> TYPE: DNA
<213> ORGANISM: Artificial Sequence
<220> FEATURE:
<223> OTHER INFORMATION: synthesized primer oligonucleotide

<400> SEQUENCE: 73
gaccgtaagg cttgatgaa                                                  19

<210> SEQ ID NO 74
<211> LENGTH: 21
<212> TYPE: DNA
<213> ORGANISM: Artificial Sequence
<220> FEATURE:
<223> OTHER INFORMATION: synthesized probe oligonucleotide

<400> SEQUENCE: 74
cgagattctc cgcgctgtag a                                               21

<210> SEQ ID NO 75
<211> LENGTH: 1150
<212> TYPE: DNA
<213> ORGANISM: Zea mays

<400> SEQUENCE: 75
caacggggca gcactgcact gcactgcaac tgcgaatttc cgtcagcttg gagcggtcca     60
agcgccctgc gaagcaaact acgccgatgg cttcggcggc ggcgtgggag ggtccgacgg    120
```

```
ccgcggagct gaagacagcg ggggcggagg tgattcccgg cggcgtgcga gtgaaggggt    180
gggtcatcca gtcccacaaa ggccctatcc tcaacgccgc ctctctgcaa cgctttgaag    240
atgaacttca aacaacacat ttacctgaga tggttttggg agagagtttc ttgtcacttc    300
aacatacaca aactggcatc aaatttcatt ttaatgcgct tgatgcactc aaggcatgga    360
agaaagaggc actgccacct gttgaggttc ctgctgcagc aaaatggaag ttcagaagta    420
agccttctga ccaggttata cttgactacg actatacatt tacgcaccca tattgtggga    480
gtgatgctgt ggttgtgaac tctggcactc cacaaacaag tttagatgga tgcggcactt    540
tgtgttggga ggatactaat gatcggattg acattgttgc cctttcagca aaagaaccca    600
ttcttttcta cgacgaggtt atcttgtatg aagatgagtt agctgacaat ggtatctcat    660
ttcttactgt gcgagtgagg gtaatgccaa ctggttggtt tctgcttttg cgttttggc     720
ttagagttga tggtgtactg atgaggttga gagacactcg gttacattgc ctgtttggaa    780
acggcgacgg agccaagcca gtggtacttc gtgagtgctg ctggagggaa gcaacatttg    840
ctactttgtc tgcgaaagga tatccttcgg actctgcagc gtacgcggac ccgaaccttt    900
ttgcccataa gcttcctatt gtgacgcaga agacccaaaa gctgaaaaat cctacctgac    960
tgacacaaag gcgccctacc gcgtgtacat catgactgtc ctgtcctatc gttgcctttt    1020
gtgtttgcca catgttgtgg atgtacgttt ctatgacgaa acaccatagt ccatttcgcc    1080
tgggccgaac agagatagct gattgtcatg tcacgtttga attagaccat tccttagccc    1140
ttttttccccc                                                          1150
```

<210> SEQ ID NO 76
<211> LENGTH: 2013
<212> TYPE: DNA
<213> ORGANISM: Zea mays

<400> SEQUENCE: 76

```
atgatccctg ccgttgctga tccgacgacg ctggacggcg ggggcgcgcg caggccgttg     60
ctcccggaga cggaccctcg ggggcgtgct gccgccggcg ccgagcagaa gcggccgccg    120
gctacgccga ccgttctcac cgccgtcgtc tccgccgtgc tcctgctcgt cctcgtggcg    180
gtcacagtcc tcgcgtcgca gcacgtcgac gggcaggctg ggggcgttcc cgcgggcgaa    240
gatgccgtcg tcgtcgaggt ggccgcctcc cgtggcgtgg ctgagggcgt gtcggagaag    300
tccacggccc cgctcctcgg ctccggcgcg ctccaggact tctcctggac caacgcgatg    360
ctggcgtggc agcgcacggc gttccacttc cagccccca agaactggat gaacgatccg    420
aacggtccgc tgtatcacaa gggctggtac cacctcttct accagtggaa cccggactcc    480
gcggtatggg gcaacatcac ctggggccac gccgtctcgc gcgacctcct ccactggctg    540
cacctaccgc tggccatggt gcccgatcac ccgtacgacg ccaacggcgt ctggtccggg    600
tcggcgacgc gcctgcccga cggcggatc gtcatgctct acacgggctc cacggcggag    660
tcgtcggcgc aggtgcagaa cctcgcggag ccggccgacg cgtccgaccc gctgctgcgg    720
gagtgggtca gtcggacgc caacccggtg ctggtgccgc cgccgggcat cgggccgacg    780
gacttccgcg acccgacgac ggcgtgtcgg acgccggccg gcaacgacac ggcgtggcgg    840
gtcgccatcg gtccaagga ccgggaccac gcggggctgg cgctggtgta ccggacggag    900
gacttcgtgc ggtacgaccc ggcgccggcg ctgatgcacg ccgtgccggg caccggcatg    960
tgggagtgcg tggacttcta cccggtggcc gcgggatcag gcgccgcggc gggcagcggg   1020
```

```
gacgggctgg agacgtccgc ggcgccggga cccggggtga agcacgtgct caaggctagc    1080
ctcgacgacg acaagcacga ctactacgcg atcggcacct acgacccggc gacggacacc    1140 tggaccccg  acagcgcgga ggacgacgtc gggatcggcc tccggtacga ctatggcaag    1200
tactacgcgt cgaagacctt ctacgacccc gtccttcgcc ggcgggtgct ctggggggtgg   1260 gtcggcgaga ccgacagcga gcgcgcggac atcctcaagg gctgggcatc cgtgcagtca    1320
atccccagga cggtcctcct ggacacgaag acgggcagca acctgctcca gtggccggtg    1380
gtggaggtgg agaacctccg gatgagcggc aagagcttcg acggcgtcgc gctggaccgc    1440
ggatccgtcg tgcccctcga cgtcggcaag gcgacgcagt tggacatcga ggctgtgttc    1500
gaggtggacg cgtcggacgc ggcgggcgtc acggaggccg acgtgacgtt caactgcagc    1560
accagcgcag gcgcggcggg ccggggcctg ctcggcccgt tcggccttct cgtgctggcg    1620
gacgacgact tgtccgagca gaccgccgtg tacttctacc tgctcaaggg cacggacggc    1680
agcctccaaa ctttcttctg ccaagacgag ctcagggcat ccaaggcgaa cgatctggtt    1740
aagagagtat acgggagctt ggtccctgtg ctagatgggg agaatctctc ggtcagaata    1800
ctggttgacc actccatcgt ggagagcttt gctcaaggcg ggaggacgtg catcacgtcg    1860
cgagtgtacc ccacacgagc catctacgac tccgcccgcg tcttcctctt caacaacgcc    1920
acacatgctc acgtcaaagc aaaatccgtc aagatctggc agctcaactc cgcctacatc    1980
cggccatatc cggcaacgac gacttctcta tga                                 2013

<210> SEQ ID NO 77
<211> LENGTH: 786
<212> TYPE: DNA
<213> ORGANISM: Escherichia coli

<400> SEQUENCE: 77
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc cacacagtga tattgatttg ctggttacgg tgaccgtaag gcttgatgaa     180
acaacgcggc gagctttgat caacgacctt ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct ttgatccggt tcctgaacag     480
gatctatttg aggcgctaaa tgaaaacctta acgctatgga actcgccgcc cgactgggct     540
ggcgatgagc gaaatgtagt gcttacgttg tcccgcattt ggtacagcgc agtaaccggc     600
aaaatcgcgc cgaaggatgt cgctgccgac tgggcaatgg agcgcctgcc ggcccagtat     660
cagcccgtca tacttgaagc taggcaggct tatcttggac aagaagatcg cttggcctcg     720
cgcgcagatc agttggaaga atttgttcac tacgtgaaag gcgagatcac caaggtagtc     780
ggcaaa                                                              786
```